US011638745B2

(12) United States Patent
Jackson et al.

(10) Patent No.: US 11,638,745 B2
(45) Date of Patent: May 2, 2023

(54) METHOD TO IMPROVE NEUROLOGIC OUTCOMES IN TEMPERATURE MANAGED PATIENTS

(71) Applicant: University of Pittsburgh—Of the Commonwealth System of Higher Education, Pittsburgh, PA (US)

(72) Inventors: Travis C. Jackson, Pittsburgh, PA (US); Patrick M. Kochanek, Pittsburgh, PA (US)

(73) Assignee: University of Pittsburgh—Of the Commonwealth Cvctom of Hierher Education, Pittsburgh, PA (US)

( * ) Notice: Subject to any disclaimer, the term of this patent is extended or adjusted under 35 U.S.C. 154(b) by 609 days.

(21) Appl. No.: 15/573,006

(22) PCT Filed: May 20, 2016

(86) PCT No.: PCT/US2016/033563
§ 371 (c)(1),
(2) Date: Nov. 9, 2017

(87) PCT Pub. No.: WO2016/187558
PCT Pub. Date: Nov. 24, 2016

(65) Prior Publication Data
US 2018/0117120 A1 May 3, 2018

Related U.S. Application Data

(60) Provisional application No. 62/164,205, filed on May 20, 2015.

(51) Int. Cl.
| | |
|---|---|
| A61K 38/18 | (2006.01) |
| A61P 25/00 | (2006.01) |
| A61K 47/68 | (2017.01) |
| A61P 9/10 | (2006.01) |
| A61P 25/28 | (2006.01) |
| A61P 9/00 | (2006.01) |
| A61P 9/04 | (2006.01) |
| A01N 1/02 | (2006.01) |
| A61F 7/00 | (2006.01) |
| A61F 7/02 | (2006.01) |
| A61F 7/10 | (2006.01) |
| A61F 7/12 | (2006.01) |
| A61K 9/00 | (2006.01) |

(52) U.S. Cl.
CPC ........ *A61K 38/1825* (2013.01); *A01N 1/0226* (2013.01); *A01N 1/0284* (2013.01); *A61F 7/0097* (2013.01); *A61F 7/02* (2013.01); *A61F 7/10* (2013.01); *A61F 7/12* (2013.01); *A61K 9/0019* (2013.01); *A61K 9/0043* (2013.01); *A61K 9/0053* (2013.01); *A61K 9/0085* (2013.01); *A61K 47/6811* (2017.08); *A61P 9/00* (2018.01); *A61P 9/04* (2018.01); *A61P 9/10* (2018.01); *A61P 25/00* (2018.01); *A61P 25/28* (2018.01); *A61F 2007/0002* (2013.01)

(58) Field of Classification Search
None
See application file for complete search history.

(56) References Cited

U.S. PATENT DOCUMENTS

| | | | |
|---|---|---|---|
| 6,156,057 A | 12/2000 | Fox | |
| 7,582,607 B2 | 9/2009 | Frye et al. | |
| 8,628,512 B2 | 1/2014 | Kochanek et al. | |
| 8,722,622 B2 | 5/2014 | Das et al. | |
| 2002/0091431 A1* | 7/2002 | Gunn | A61F 7/02 607/110 |
| 2007/0082918 A1* | 4/2007 | Naftchi | A61K 31/522 514/263.35 |
| 2009/0305986 A1 | 12/2009 | Belouski et al. | |
| 2010/0204634 A1* | 8/2010 | Baxter | A61M 25/007 604/6.13 |

(Continued)

FOREIGN PATENT DOCUMENTS

| | | |
|---|---|---|
| WO | 2010042747 A2 | 4/2010 |
| WO | 2012151349 A1 | 11/2012 |

OTHER PUBLICATIONS

Kim, Kook & Lee, Myung-Shik. (2014). FGF21 as a Stress Hormone: The Roles of FGF21 in Stress Adaptation and the Treatment of Metabolic Diseases. Diabetes & metabolism journal. 38. 245-51. (Year: 2014).*

Chip, Sophorn & Zelmer, Andrea & Ogunshola, Omolara & Felderhoff-Mueser, Ursula & Nitsch, Cordula & Bührer, Christoph & Wellmann, Sven. (2011). The RNA-binding protein RBM3 is involved in hypothermia induced neuroprotection. Neurobiology of disease. 43. 388-96. (Year: 2011).*

(Continued)

*Primary Examiner* — Joseph A Stoklosa
*Assistant Examiner* — Adam J Avigan
(74) *Attorney, Agent, or Firm* — The Webb Law Firm

(57) ABSTRACT

A method of improving brain function in a hypothermic patient is provided. The method comprises administering to the patient an amount of a fibroblast growth factor 21 (FGF21) effective to increase RNA binding motif 3 (RBM3) production in nerve cells of the patient. The method is useful, for example, where the patient is or will be undergoing cardiac surgery or spinal surgery, such as requiring deep hypothermia circulatory arrest (DHCA), or is subject to an emergency preservation and resuscitation (EPR) method, or where a patient suffers from mild/moderate/severe traumatic brain injury (TBI), ventricular fibrillation cardiac arrest (VFCA), subarachnoid hemorrhage (SAH), subdural hematoma (SH), cerebral vasospasm, neonatal abusive head trauma (a.k.a. shaken baby syndrome), neonatal hypoxic ischemic encephalopathy (HIE), asphyxia cardiac arrest (ACA), treatment of spinal injury, prophylaxis in spinal surgery, stroke, and drug overdose.

18 Claims, 23 Drawing Sheets
Specification includes a Sequence Listing.

(56) References Cited

U.S. PATENT DOCUMENTS

| | | | | |
|---|---|---|---|---|
| 2011/0318431 | A1* | 12/2011 | Gulati | A61P 1/16 |
| | | | | 424/681 |
| 2012/0282279 | A1 | 11/2012 | Das et al. | |
| 2014/0228282 | A1 | 8/2014 | Darling et al. | |
| 2014/0287996 | A1* | 9/2014 | Liu | A61K 38/1833 |
| | | | | 514/9.1 |
| 2014/0323396 | A1 | 10/2014 | Belouski et al. | |
| 2015/0133419 | A1* | 5/2015 | Foidart | A61P 25/28 |
| | | | | 514/182 |

OTHER PUBLICATIONS

Leng, Y., Wang, Z., Tsai, L. K., Leeds, P., Fessler, E. B., Wang, J., & Chuang, D. M. (2015). FGF-21, a novel metabolic regulator, has a robust neuroprotective role and is markedly elevated in neurons by mood stabilizers. Molecular psychiatry, 20(2), 215-223. (Year: 2015).*
Niemann CU, Malinoski D. Therapeutic Hypothermia in Deceased Organ Donors and Kidney-Graft Function. N Engl J Med. Dec. 2015;373(27) 2687. (Year: 2015).*
Kharitonenkov et al. (2013) Rational Design of a Fibroblast Growth Factor 21-Based Clinical Candidate, LY2405319. Plos One 8(3): e58575 (Year: 2013).*
Dostalova et al. Fibroblast Growth Factor 21: A Novel Metabolic Regulator With Potential Therapeutic Properties in Obesity/Type 2 Diabetes Mellitus. (2009) Physiol. Res. 58: 1-7 (Year: 2009).*
Yu et al. Fibroblast growth factor (FGF21) protects mouse liver against D-galactose-induced oxidative stress and apoptosis via activating Nrf2 and PI3K/Akt pathways. (2015) Mol Cell Biochem 403:287-299 (Year: 2015).*
Kharitonenkov et al. FGF-21 as a novel metabolic regulator. (2005) J Clin Invest. X 115(6):1627-1635 (Year: 2005).*
Adams et al.; "Fibroblast growth factor 21 is not required for the antidiabetic actions of the thiazoladinediones"; Molecular Metabolism; 2013; pp. 205-214; vol. 2:3.
Adams et al.; "LY2405319, an Engineered FGF21 Variant, Improves the Metabolic Status of Diabetic Monkeys"; PLoS ONE; Jun. 18, 2013; pp. e65763; vol. 8:6.
Adelson et al.; "Histopathologic Response of the Immature Rat to Diffuse Traumatic Brain Injury"; Journal of Neurotrauma; 2001; pp. 967-976; vol. 18:10.
Adelson et al.; "Morris water maze function and histologic characterization of two age-at-injury experimental models of controlled cortical impact in the immature rat"; Childs Nerv Syst; 2013; pp. 43-53; vol. 29.
Adelson et al.; "Comparison of hypothermia and normothermia after severe traumatic brain injury in children (Cool Kids): a phase 3, randomised controlled trial"; Lancet Neurol; 2013; pp. 546-553; vol. 12.
Ahlemeyer et al.; "Cytosine arabinofuranoside-induced activation of astrocytes increases the susceptibility of neurons to glutamate due to the release of soluble factors"; NEUROCHEMISTRY International; 2003; pp. 567-581; vol. 42.
Atkins et al.; "Hypothermia treatment potentiates ERK 1/2 activation after traumatic brain injury"; European Journal of Neuroscience; 2007; pp. 810-819; vol. 26.
Baker et al.; "Intraischemic Hypothermia Decreases the Release of Glutamate in the Cores of Permanent Focal Cerebral Infarcts"; Neurosurgery; May 1995; pp. 994-1002; vol. 36:5.
Barnes; "Freeze Avoidance in a Mammal: Body Temperatures below 0° C in an Arctic Hibernator"; Science; Jun. 30, 1989; pp. 1593-1595; vol. 244:4912.
Belinsky et al.; "Mild Hypothermia Inhibits Differentiation of Human Embryonic and Induced Pluripotent Stem Cells"; BioTechniques; 2013; pp. 79-82; vol. 55:2.
Bernardo et al.; "FGF21 does not require interscapular brown adipose tissue and improves liver metabolic profile in animal models of obesity and insulin-resistance"; Scientific Reports; 2015; pp. 1-13; vol. 5:11382.

Berntman et al.; "Cerebral Protective Effect of Low-Grade Hypothermia"; Anesthesiology; 1981; pp. 495-498; vol. 55:5.
Bilotta et al.; "Intensive Insulin Therapy After Severe Traumatic Brain Injury: A Randomized Clinical Trial"; Neurocrit Care; 2008; pp. 159-166; vol. 9.
Bohman et al.; "Fever and therapeutic normothermia in severe brain injury: an update"; Curr Opin Crit Care; Apr. 2014; pp. 182-188; vol. 20:2.
Bookout et al.; "FGF21 regulates metabolism and circadian behavior by acting on the nervous system"; nature medicine; Sep. 2013; pp. 1147-1152; vol. 19:9.
Busto et al.; "Small Differences in Intraischemic Brain Temperature Critically Determine the Extent of Ischemic Neuronal Injury"; Journal of Cerebral Blood Flow and Metabolism; 1987; pp. 729-738; vol. 7.
Busto et al.; "Effect of Mild Hypothermia on Ischemia-Induced Release of Neurotransmitters and Free Fatty Acids in Rat Brain"; Stroke; 1989; pp. 904-910; vol. 20.
Cairns et al.; "Management of hypothermia in traumatic brain injury"; Current Opinion in Critical Care; 2002; pp. 106-110; vol. 8.
Castelo-Branco et al.; "GSK-3β inhibition/β-catenin stabilization in ventral midbrain precursors increases differentiation into dopamine neurons"; Journal of Cell Science; 2004; pp. 5731-5737; vol. 117:24.
Childs et al.; "Hypothermia Reduces Microvascular Permeability and Reactive Oxygen Species Expression after Hemorrhagic Shock"; J Trauma; 2005; pp. 271-277; vol. 58:2.
Chip et al.; "The RNA-binding protein RBM3 is involved in hypothermia induced neuroprotection"; Neurobiology of Disease; 2011; pp. 388-396; vol. 43.
Clark et al.; "Mild Posttraumatic Hypothermia Reduces Mortality After Severe Controlled Cortical Impact in Rats"; Journal of Cerebral Blood Flow and Metabolism; 1996; pp. 253-261; vol. 16.
Clark et al.; "Apoptosis-Suppressor Gene bcl-2 Expression after Traumatic Brain Injury in Rats"; The Journal of Neuroscience; Dec. 1, 1997; pp. 9172-9182; vol. 17:23.
Clark et al.; "A simple method to induce focal brain hypothermia in rats"; Journal of Cerebral Blood Flow & Metabolism; 2007; pp. 115-122; vol. 27.
Clemens; "Initiation Factor elF2α Phosphorylation in Stress Responses and Apoptosis"; Progress in Molecular and Subcellular Biology; 2001; pp. 57-89; vol. 27.
Corbett et al.; "Persistent Neuroprotection with Prolonged Postischemic Hypothermia in Adult Rats Subjected to Transient Middle Cerebral Artery Occlusion"; Experimental Neurology; 2000; pp. 200-206; vol. 163.
Corton et al.; "Mimetics of Caloric Restriction Include Agonists of Lipid-activated Nuclear Receptors"; The Journal of Biological Chemistry; 2004; pp. 46204-46212; vol. 279:44.
Crunkhorn; "FGF21 analogue shows promise in the clinic"; Nature Reviews Drug Discovery; Nov. 2013; pp. 825; vol. 12.
Dietrich; "The Importance of Brain Temperature in Cerebral Injury"; Journal of Neurotrauma; 1992; pp. S475-S485; vol. 9 Suppl 2.
Dietrich et al.; "The Evidence for Hypothermia as a Neuroprotectant in Traumatic Brain Injury"; Neurotherapeutics: The Journal of the American Society for Experimental NeuroTherapeutics; Jan. 2010; pp. 43-50; vol. 7:1.
Dixon et al.; "Amantadine improves water maze performance without affecting motor behavior following traumatic brain injury in rats"; Restorative Neurology and Neuroscience; 1999; pp. 285-294; vol. 14.
Doppalapudi et al.; "Chemical generation of bispecific antibodies"; PNAS; Dec. 28, 2010; pp. 22611-22616; vol. 107:52.
Douris et al.; "Central Fibroblast Growth Factor 21 Browns White Fat via Sympathetic Action in Male Mice" Endocrinology; 2015; pp. 2470-2481.
Dresios et al.; "Cold stress-induced protein Rbm3 binds 60S ribosomal subunits, alters microRNA levels, and enhances global protein synthesis"; PNAS; Feb. 8, 2005; pp. 1865-1870; vol. 102:6.
Duran et al.; "Impairment in long-term memory formation and learning-dependent synaptic plasticity in mice lacking glycogen

(56) References Cited

OTHER PUBLICATIONS synthase in the brain"; Journal of Cerebral Blood Flow and Metabolism; 2013; pp. 550-556; vol. 33.
Faul et al.; "Traumatic Brain Injury in the United States: Emergency Department Visits, Hospitalizations and Deaths 2002-2006"; U.S. Department of Health and Human Services: Centers for Disease Control and Prevention, National Center for Injury Prevention and Control; Mar. 2010; Atlanta, GA.
Fedorov et al.; "Elevated expression of protein biosynthesis genes in liver and muscle of hibernating black bears (Ursus americanus)"; Physiol Genomics; 2009; pp. 108-118; vol. 37.
Fedorov et al.; "Modulation of gene expression in heart and liver of hibernating black bears (Ursus americanus)"; BMC Genomics; 2011; 15 Pages; vol. 12:171.
Fink et al.; "Brief Induced Hypothermia Improves Outcome in a Pediatric Model of Asphyxial Cardiopulmonary Arrest in Rats"; Crit Care Med; 2003; pp. A9; vol. 31:12 (Suppl).
Fink et al.; "Brief Induced Hypothermia Improves Outcome after Asphyxial Cardiopulmonary Arrest in Juvenile Rats" Developmental Neuroscience; 2005; pp. 191-199; vol. 27.
Fisher et al.; "FGF21 regulates PGC-1α and browning of white adipose tissues in adaptive thermogenesis"; Genes and Development; 2012; pp. 271-281; vol. 26.
Fukuda et al.; "Post-ischemic hypothermia blocks caspase-3 activation in the newborn rat brain after hypoxia-ischemia"; Brain Research; 2001; pp. 187-191; vol. 910.
Fukuoka et al.; "Biphasic concentration change during continuous midazolam administration in brain-injured patients undergoing therapeutic moderate hypothermia"; Resuscitation; 2004; pp. 225-230; vol. 60.
Gaich et al.; "The Effects of LY2405319, an FGF21 Analog, in Obese Human Subjects with Type 2 Diabetes"; Cell Metabolism; Sep. 3, 2013; pp. 333-340; vol. 18.
Georgievska et al.; "AZD1080, a novel GSK3 inhibitor, rescues synaptic plasticity deficits in rodent brain and exhibits peripheral target engagement in humans"; Journal of Neurochemistry; 2013; pp. 446-456; vol. 125.
Globus et al.; "Glutamate Release and Free Radical Production Following Brain Injury: Effects of Posttraumatic Hypothermia"; Journal of Neurochemistry; 1995; pp. 1704-1711; vol. 65.
Greer et al.; "Impact of Fever on Outcome in Patients With Stroke and Neurologic Injury: A Comprehensive Meta-Analysis"; Stroke; 2008; pp. 3029-3035; vol. 39.
Hemerka et al.; "Severe Brief Pressure-Controlled Hemorrhagic Shock after Traumatic Brain Injury Exacerbates Functional Deficits and Long-Term Neuropathological Damage in Mice"; Journal of Neurotrauma; Aug. 10, 2012; pp. 2192-2208; vol. 29.
Holzinger et al.; "Resting energy expenditure and substrate oxidation rates correlate to temperature and outcome after cardiac arrest—a prospective observational cohort study"; Critical Care; 2015; 9 Pages; vol. 19:128.
Hondares et al.; "Thermogenic Activation Induces FGF21 Expression and Release in Brown Adipose Tissue"; Journal of Biological Chemistry; Apr. 15, 2011; pp. 12983-12990; vol. 286:15.
Puccio et al.; "Induced Normothermia Attenuates Intracranial Hypertension and Reduces Fever Burden after Severe Traumatic Brain Injury"; Neurocritic Care; 2009; pp. 82-87; vol. 11.
Qiang et al.; "Cold-inducible RNA-binding protein (CIRP) triggers inflammatory responses in hemorrhagic shock and sepsis"; Nature Medicine; Nov. 2013; pp. 1489-1495; vol. 19:11.
Robertson et al.; "Melatonin augments hypothermic neuroprotection in a perinatal asphyxia model"; Brain; 2013; pp. 90-105; vol. 136.
Rosomoff et al.; "Cerebral Blood Flow and Cerebral Oxygen Consumption During Hypothermia"; American Journal of Physiology; Oct. 1954; pp. 85-88; vol. 179.
Samms et al.; "Discrete Aspects of FGF21 In Vivo Pharmacology Do Not Require UCP1"; Cell Reports; May 19, 2015; pp. 991-999; vol. 11.
Sandestig et al.; "Therapeutic Hypothermia in Children and Adults with Severe Traumatic Brain Injury"; Therapeutic Hypothermia and Temperature Management; 2014; pp. 10-20; vol. 4:1.
Schmidt et al.; "SUnSET, a nonradioactive method to monitor protein sythesis"; Nature Methods; Apr. 2009; pp. 275-277; vol. 6:4.
Schreckinger et al.; "Contemporary Management of Traumatic Intracranial Hypertension: Is There a Role for Therapeutic Hypothermia?"; Neurocritic Care; 2009; pp. 427-436; vol. 11.
Schwartz et al.; "Seasonal and Regional Differences in Gene Expression in the Brain of a Hibernating Mammal"; Plos One; Mar. 20, 2013; p. e58427; vol. 8:3.
Shankaran et al.; "Whole-Body Hypothermia for Neonates with Hypoxic-Ischemic Encephalopathy"; The New England Journal of Medicine; Oct. 13, 2005; pp. 1574-1584; vol. 353:15.
Siebke et al.; "Survival After 40 Minutes' Submersion Without Cerebral Sequelae"; Lancet; Jun. 7, 1975; pp. 1275-1277; vol. 1.
Smart et al.; "Two isoforms of the cold-inducible mRNA-binding protein RBM3 localize to dendrites and promote translation"; Journal of Neurochemistry; 2007; pp. 1367-1379; vol. 101.
Smith et al.; "Small molecule activators of SIRT I replicate signaling pathways triggered by calorie restriction in vivo"; BMC Systems Biology; 2009; 14 Pages; vol. 3:31.
Tagin et al.; "Hypothermia for Neonatal Hypoxic Ischemic Encephalopathy: An Updated Systematic Review and Meta-analysis"; Arch Pediatr Adolesc Med; Jun. 2012; pp. 558-566; vol. 166:6.
Tam et al.; "Occipital Lobe Injury and Cortical Visual Outcomes After Neonatal Hypoglycemia"; Pediatrics; Sep. 2008; pp. 507-512; vol. 122:3.
Thermo Scientific; Crosslinking Technical Handbook; "easy molecular bonding: crosslinking technology: Reactivity chemistries, applications and structure references"; 2012; 54 Pages.
Tian et al.; "A meta-analysis of deep hypothermic circulatory arrest alone versus with adjunctive selective antegrade cerebral perfusion"; Ann Cardiothorac Surg; 2013; pp. 261-270; vol. 2:3.
Titus et al.; "Emergence of Cognitive Deficits after Mild Traumatic Brain Injury due to Hypothermia"; Exp Neurol; Jan. 2015; pp. 254-262; vol. 263.
Toien et al.; "Hibernation in Black Bears: Independence of Metabolic Suppression from Body Temperature"; Science; Feb. 18, 2011; pp. 906-909; vol. 331.
Tomura et al.; "Effects of therapeutic hypothermia on inflammasome signaling after traumatic brain injury"; Journal of Cerebral Blood Flow and Metabolism; 2012; pp. 1939-1947; vol. 32.
Tong et al.; "Effects of moderate and deep hypothermia on RNA-binding proteins RBM3 and CIRP expressions in murine hippocampal brain slices"; Brain Research; 2013; pp. 74-84; vol. 1504.
Vosler et al.; "Ischemia-induced calpain activation causes eukaryotic (translation) initiation factor 4G1 (eIF4GI) degradation, protein synthesis inhibition, and neuronal death"; PNAS; Nov. 1, 2011; pp. 18102-18107; vol. 108:44.
Wass et al.; "Temperature Changes of greater than or equal to 1DegreeC Alter Functional Neurologic Outcome and Histopathology in a Canine Model of Complete Cerebral Ischemia"; Anesthesiology; 1995; pp. 325-335; vol. 83.
Wei et al.; "Neuroprotection of Selective Brain Cooling After Penetrating Ballistic-like Brain Injury in Rats"; Therapeutic Hypothermia and Temperature Management; 2011; pp. 33-42; vol. 1:1.
Weinrauch et al.; "Beneficial Effect of Mild Hypothermia and Detrimental Effect of Deep Hypothermia After Cardiac Arrest in Dogs"; Stroke; 1992; pp. 1454-1462; vol. 23.
Wellmann et al.; "The RNA-Binding Protein RBM3 Is Required for Cell Proliferation and Protects Against Serum Deprivation-Induced Cell Death"; Pediatric Research; 2010; pp. 35-41; vol. 67:1.
Welsh et al.; "Mild Hypothermia Prevents Ischemic Injury in Gerbil Hippocampus"; Journal of Cerebral Blood Flow and Metabolism; 1990; pp. 557-563; vol. 10.
Weng et al.; "Pharmacokinetics (PK), Pharmacodynamics (PD) and Integrated PK/PD Modeling of a Novel Long Acting FGF21 Clinical Candidate PF-05231023 in Diet-Induced Obese and Leptin-Deficient Obese Mice"; Plos One; Mar. 19, 2015; p. e0119104; vol. 10:3.
Widmann et al.; "Protective Effect of Hypothermia on Hippocampal Injury After 30 Minutes of Forebrain Ischemia in Rats Is Mediated

(56) References Cited

OTHER PUBLICATIONS by Postischemic Recovery of Protein Synthesis"; Journal of Neurochemistry; 1993; pp. 200-209; vol. 61:1.
Williams et al.; "Seasonally hibernating phenotype assessed through transcript screening"; Physiol Genomics; 2005; pp. 13-22; vol. 24.
Wong; "Physiology and Pharmacology of Hypothermia (Medical Progress)"; The West J Med; Feb. 1983; pp. 227-232; vol. 138.
Xu et al.; "Fibroblast Growth Factor 21 Reverses Hepatic Steatosis, Increases Energy Expenditure, and Improves Insulin Sensitivity in Diet-Induced Obese Mice"; Diabetes; Jan. 2009; pp. 250-259; vol. 58.
Yamashita et al.; "Mild Hypothermia Ameliorates Ubiquitin Synthesis and Prevents Delayed Neuronal Death in the Gerbil Hippocampus"; Stroke; Dec. 1991; pp. 1574-1581; vol. 22.
Yang et al.; "Hypothermia attenuates ischemia/reperfusion-induced endothelial cell apoptosis via alterations in apoptotic pathways and JNK signaling"; FEBS Letters; 2009; pp. 2500-2506; vol. 583.
Yie et al.; "FGF21 N-and C-termini play different roles in receptor interaction and activation"; FEBS Letters; 2009; pp. 19-24; vol. 583.
Yu et al.; "Fibroblast growth factor (FGF21) protects mouse liver against D-galactose-induced oxidative stress and apoptosis via activating Nrf2 and PI3K/Akt pathways"; Mol Cell Biochem; 2015; pp. 287-299; vol. 403.
Zhang et al.; "Klotho is a target gene of PPAR-γ"; Kidney International; 2008; pp. 732-739; vol. 74.
Zhang et al.; "When hypothermia meets hypotension and hyperglycemia: the diverse effects of adenosine 5'-monophosphate on cerebral ischemia in rats"; Journal of Cerebral Blood Flow and Metabolism; 2009; pp. 1022-1034; Vol. 29.
Zhou et al.; "Cold-inducible RNA-binding protein mediates neuroinflammation in cerebral ischemia"; Biochimica et Biophysica Acta; 2014; pp. 2253-2261; vol. 1840.
Ziganshin et al.; "Deep hypothermic circulatory arrest"; Ann Cardiothorac Surg; 2013; pp. 303-315; vol. 2:3.
Zona et al.; "Age-Dependent Appearance of Synaptic Currents in Rat Neocortical Neurons in Culture"; Synapse; 1994; pp. 1-6; vol. 18.
Hsuchou et al.; "The fasting polypeptide FGF21 can enter brain from blood"; Peptides; 2007; pp. 2382-2386; vol. 28.
Huang et al.; "Development of a Novel Long-Acting Antidiabetic FGF21 Mimetic by Targeted Conjugation to a Scaffold Antibody"; The Journal of Pharmacology and Experimental Therapeutics; Aug. 2013; pp. 270-280; vol. 346.
Inagaki et al.; "Endocrine Regulation of the Fasting Response by PPARα-Mediated Induction of Fibroblast Growth Factor 21"; Cell Metabolism; Jun. 2007; pp. 415-425; vol. 5.
Ivanov et al.; "Pathogen signatures activate a ubiquitination pathway that modulates the function of the metabolic checkpoint kinase mTOR"; Nature Immunology; Dec. 2013; pp. 1219-1231; vol. 14:12.
Jackson et al.; "Regional hippocampal differences in AKT survival signaling across the lifespan: implications for CA1 vulnerability with aging"; Cell Death and Differentiation; 2009; pp. 439-448; vol. 16.
Jackson et al.; "PHLPP1 splice variants differentially regulate AKT and PKCα signaling in hippocampal neurons: characterization of PHLPP proteins in the adult hippocampus"; Journal of Neurochemistry; 2010; pp. 941-955; vol. 115.
Jackson et al.; "Anthraquinone-2-sulfonic acid (AQ2S) is A Novel Neurotherapeutic Agent"; Cell Death and Disease; 2013; p. e451; vol. 4.
Jackson et al.; "Pharmacological Inhibition of Pleckstrin Homology Domain Leucine-Rich Repeat Protein Phosphatase in Neuroprotective: Differential Effects on Astrocytes"; The Journal of Pharmacology and Experimental Therapeutics; Nov. 2013; pp. 516-528; vol. 347.
Jackson et al.; "Effect of TBI on RNA Binding Motif 5 (RBM5) and 3 (RBM3) Protein Expression in the Developing Rat Brain"; [Abstract] National Neurotrauma Society; 2014; p. A-61.
Jackson et al.; "Cold Stress Protein RBM3 Responds to Temperature Change in an Ultra-Sensitive Manner in Young Neurons"; Neuroscience; 2015; pp. 268-278; vol. 305.
Jackson et al.; "Detection of PHLPP1 α/β in Human and Mouse Brain by Different Anti-PHLPP1 Antibodies"; Scientific Reports; Apr. 1, 2015; 8 Pages; vol. 5:9377.
Jenkins et al.; "Conventional and Functional Proteomics Using Large Format Two-Dimensional Gel Electrophoresis 24 Hours after Controlled Cortical Impact in Postnatal Day 17 Rats"; Journal of Neurotrauma; 2002; pp. 715-740; vol. 19:6.
Ji et al.; "Lipidomics identifies cardiolipin oxidation as a mitochondrial target for redox therapy of brain injury"; Nature Neuroscience; Oct. 2012; pp. 1407-1413; vol. 15:10.
Kern et al.; "The Effects of Temperature and Seasons on Subcutaneous White Adipose Tissue in Humans: Evidence for Thermogenic Gene Induction"; J Clin Endocrinol Metab; Dec. 2014; pp. E2772-E2779; vol. 99:12.
Kharitonenkov et al.; "FGF-21 as a novel metabolic regulator"; The Journal of Clinical Investigation; Jun. 2005; pp. 1627-1635; vol. 115:6.
Kharitonenkov et al.; "The Metabolic State of Diabetic Monkeys Is Regulated by Fibroblast Growth Factor-21"; Endocrinology; 2007; pp. 774-781; vol. 148:2.
Kharitonenkov et al.; "Rational Design of a Fibroblast Growth Factor 21-Based Clinical Candidate, LY2405319"; Plos One; Mar. 11, 2013; p. e58575; vol. 8:3.
Kim et al.; "Acute Exercise Induces FGF21 Expression in Mice and in Healthy Humans"; Plos One; May 7, 2013; p. e63517; vol. 8:5.
Kochanek et al.; "Gel-Based Hippocampal Proteomic Analysis 2 Weeks following Traumatic Brain Injury to Immature Rats Using Controlled Cortical Impact"; Developmental Neuroscience; 2006; pp. 410-419; vol. 28.
Kushimoto et al.; "The impact of body temperature abnormalities on the disease severity and outcome in patients with severe sepsis: an analysis from a multicenter, prospective survey of severe sepsis"; Critical Care; 2013; p. R271; vol. 17.
Laptook et al.; "Elevated Temperature After Hypoxic-Ischemic Encephalopathy: Risk Factor for Adverse Outcomes"; Pediatrics; Sep. 2008; pp. 491-499; vol. 122:3.
Leng et al.; "FGF-21, a novel metabolic regulator, has a robust neuroprotective role and is markedly elevated in neurons by mood stabilizers"; Molecular Psychiatry; 2015; pp. 215-223; vol. 20.
Lesuisse et al.; "Long-Term Culture of Mouse Cortical Neurons as a Model for Neuronal Development, Aging, and Death"; Journal of Neurobiology; 2002; pp. 9-23; vol. 51.
Lin et al.; "Development of Excitatory Synapses in Cultured Neurons Dissociated From the Cortices of Rat Embryos and Rat Pups at Birth"; Journal of Neuroscience Research; 2002; pp. 484-493; vol. 67.
Liu et al.; "Cold-induced RNA-binding proteins regulate circadian gene expression by controlling alternative polyadenylation"; Scientific Reports; Jun. 24, 2013; 11 Pages; vol. 3:2054.
Liu et al.; "Endocrine Protection of Ischemic Myocardium by FGF21 from the Liver and Adipose Tissue"; Scientific Reports; Sep. 26, 2013; 11 Pages; vol. 3:2767.
Lucas et al.; "Adverse neurodevelopmental outcome of moderate neonatal hypoglycaemia"; British Medical Journal; Nov. 19, 1988; pp. 1304-1308; vol. 297.
Lyden et al.; "Therapeutic hypothermia for acute stroke"; International Journal of Stroke; Feb. 2006; pp. 9-19; vol. 1.
Maas et al.; "Moderate and severe traumatic brain injury in adults"; Lancet Neurol; 2008; pp. 728-741; vol. 7.
Maekawa et al.; "Prolonged Mild Therapeutic Hypothermia versus Fever Control with Tight Hemodynamic Monitoring and Slow Rewarming in Patients with Severe Traumatic Brain Injury: A Randomized Controlled Trial"; Journal of Neurotrauma; Apr. 1, 2015; pp. 422-429; vol. 32.
Makela et al.; "Fibroblast growth factor-21 enhances mitochondrial functions and increases the activity of PGC-1α in human dopaminergic neurons via Sirtuin-1"; SpringerPlus; 2014; p. 2; vol. 3:2.
Marion; "Optimum serum glucose levels for patients with severe traumatic brain injury"; Medicine Reports; 2009; 4 Pages; vol. 1:42.

(56) References Cited

OTHER PUBLICATIONS

Matsuda et al.; "Generation of mice deficient in RNA-binding motif protein 3 (RBM3) and characterization of its role in innate immune responses and cell growth"; Biochemical and Biophysical Research Communications; 2011; pp. 7-13; vol. 411.

Melhuish; "Linking hypothermia and hyperglycemia"; Nursing Management; Dec. 2009; pp. 42-45.

Minamisawa et al.; "The Influence of Mild Body and Brain Hypothermia on Ischemic Brain Damage"; Journal of Cerebral Blood Flow and Metabolism; 1990; pp. 365-374; vol. 10.

Moler et al.; "Therapeutic Hypothermia after Out-of-Hospital Cardiac Arrest in Children"; The New England Journal of Medicine; May 14, 2015; pp. 1898-1908; vol. 372:20.

Nelson et al.; "Metabolic Hormone FGF21 Is Induced in Ground Squirrels during Hibernation but Its Overexpression Is Not Sufficient to Cause Torpor"; Plos One; Jan. 2, 2013; p. e53574; vol. 8:1.

Newman et al.; "Lactate Produced by Glycogenolysis in Astrocytes Regulates Memory Processing"; Plos One; Dec. 13, 2011; p. e28427; vol. 6:12.

Nielsen et al.; "Targeted Temperature Management at 33DegreeC versus 36DegreeC after Cardiac Arrest"; The New England Journal of Medicine; 2013; pp. 2197-2206; vol. 369:23.

Niemann et al.; "Therapeutic Hypothermia in Deceased Organ Donors and Kidney-Graft Function"; The New England Journal of Medicine; Jul. 30, 2015; pp. 405-414; vol. 373:5.

Noor et al.; "Effects of hyperthermia on infarct volume in focal embolic model of cerebral ischemia in rats"; Neuroscience Letters; 2003; pp. 130-132; vol. 349.

Onesti et al.; "Transient Hypothermia Reduces Focal Ischemic Brain Injury in the Rat"; Neurosurgery; 1991; pp. 369-373; vol. 29:3.

Peberdy et al.; "Part 9: Post-Cardiac Arrest Care: 2010 American Heart Association Guidelines for Cardiopulmonary Resuscitation and Emergency Cardiovascular Care"; Circulation; 2010; pp. S768-S786; vol. 122.

Peretti et al.; "RBM3 mediates structural plasticity and protective effects of cooling in neurodegeneration"; Nature; Feb. 12, 2015; pp. 236-239; vol. 518.

Pierre et al.; "Loss of translation: a stealth weapon against pathogens?"; Nature Immunology; Dec. 2013; pp. 1203-1205; vol. 14:12.

Pilotte et al.; "Developmentally regulated expression of the cold-inducible RNA-binding motif protein 3 in euthermic rat brain"; Brain Research; 2009; pp. 12-24; vol. 1258.

Pilotte et al.; "Widespread Regulation of miRNA Biogenesis at the Dicer Step by the Cold-Inducible RNA-Binding Protein, RBM3"; Plos One; Dec. 1, 2011; p. e28446; vol. 6:12.

Planavila et al.; "Fibroblast growth factor 21 protects against cardiac hypertrophy in mice"; Nature Communications; Jun. 17, 2013; 12 Pages; vol. 4:2019.

Potthoff et al.; "FGF21 induces PGC-1α and regulates carbohydrate and fatty acid metabolism during the adaptive starvation response"; PNAS; Jun. 30, 2009; pp. 10853-10858; vol. 106:26.

Povlishock et al.; "Posthypothermic Rewarming Considerations following Traumatic Brain Injury"; Journal of Neurotrauma; Mar. 2009; pp. 333-340; vol. 26.

\* cited by examiner

MSSEEGKLFV GGLNFNTDEQ ALEDHFSSFG PISEVVVVKD RETQRSRGFG FITFTNPEHA
SVAMRAMNGE SLDGRQIRVD HAGKSARGTR GGGFGAHGRG RSYSRGGGDQ GYGSGRYYDS
RPGGYGYGYG RSRDYNGRNQ GGYDRYSGGN YRDNYDN (SEQ ID NO: 1)

Fig. 1A

```
   1 gaacactgct cccttcgctt tgctgtccct tcctctcccc accactccgc tcctgctggc
  61 ctcagccaat cagcacgcac gccgggacgc gcaaggggaa cgttccggga cgttctcgct
 121 acgtactctt tatcaatcgt cttccggcgc agcccgtcc ctgttttttg tgctcctccg
 181 agctcgctgt tcgtccgggt tttttacgtt ttaatttcca ggacttgaac tgccatgtcc
 241 tctgaagaag gaaagctctt cgtgggaggg ctcaacttta acaccgacga gcaggcactg
 301 gaagaccact tcagcagttt cggacctatc tctgaggtgg tcgttgtcaa ggaccgggag
 361 actcagcggt ccaggggttt tggtttcatc accttcacca acccagagca tgcttcagtt
 421 gccatgagag ccatgaacgg agagtctctg atggtcgtc agatccgtgt ggatcatgca
 481 ggcaagtctg ctcggggaac cagaggaggt ggctttgggg cccatgggcg tggtcgcagc
 541 tactctagag gtggtgggga ccagggctat gggagtggca ggtattatga cagtcgacct
 601 ggagggtatg gatatggata tggacgttcc agagactata atggcagaaa ccagggtggt
 661 tatgaccgct actcaggagg aaattacaga gacaattatg acaactgaaa tgagacatgc
 721 acataatata gatacacaag gaataatttc tgatccagga tcgtccttcc aaatgctgt
 781 atttataaag gtttttggag ctgcaccgaa gcatcttatt ttatagtata tcaaccttt
 841 gttttaaat tgacctgcca aggtagctga agacctttta gacagttcca tcttttttt
 901 taaattttt ctgcctattt aaagacaaat tatgggacgt tgtagaacc tgagtatttt
 961 tcttttacc agttttttag tttgagctct taggtttatt ggagctagca ataattggtt
1021 ctggcaagtt tggccagact gacttcaaaa aattaatgtg tatccaggga catttttaaaa
1081 acctgtacac agtgtttatt gtggttagga agcaatttcc caatgtacct ataagaaatg
1141 tgcatcaagc cagcctgacc aacatggtga acccatct gtactaaaca taaaaaatt
1201 agcctggcat ggtggtgtac gcctgtaatc ccagtgactt gggaggctga ggcaggagaa
1261 tcgcttgaac ccgggaggcg gaggttgcag tgagctaaga tcgcgccact gtactccagc
1321 ctgggcaaca gcgagactcc atctcaaaaa aaaggaaat gtgtatcaag aacatgatta
1381 tccagcggta ttttctaatt cagatcatca aactgattat atagaagagt tggctttaaa
1441 atgtttgcaa atgtctttt tttttaata ctggaagaaa aaatattctg ttgtgtctca
1501 tacagtgctt aggatgtctt tcacagagct tattaaaaag atgaaacctg agaacaaact
1561 gctttattct tactcagccc attttgcaaa ttaaagtgg gggcagaggt gggcggatca
1621 cctgaggtca ggagttcgag accagcctgg ccaacaggc aaaacccat ctctactaaa
1681 aatacaaaag ttagcggggc gtggtggcgg gtgcatgtaa tcccagctac tcgggaggct
1741 gaggcaggag aattgcttga acccaggagg cggaagttgc agtgagctga gattgtgcca
1801 ctgcactcca gcctaggtga cagcaagact ctgtctcaaa aaaaaaaaa tggcacatca
1861 acgagaggga ggcttggaga atatttggtt ggtggtggg caggactgc cagagggtta
1921 ggtgtacatt gaggcctgag gcctgctgga attgggtttc cttaactggt ctcttatctt
1981 agtcccattg ttctgagaac ataagcacct aatctcatgg cgtgagctaa tccctatcat
2041 aaatagtggt accagttcat tccttcccct gaaatgatgg gggttgggca gagatgcact
2101 gaactcatct ttgtgtatga gggccatgag agaggcctgg tttgaaaaca atgctaagag
2161 ctcagattcc aggatttatg tagggctct tctacttccc aggtatttga cctcaggtga
2221 gtcatttaat ttcagcctta tgccattta catttctgt ggagggttag gttaattggc
2281 atataaagcc actgagaaga gttggcaaag ctctcagtca cggggatttg atcttttttg
2341 gtgtgtgtgt gtcttgggtg gtaaagtggg aattttgtaa ttctagctgg cttagttcc
2401 tcagttctgc tcccttagt catggttctt tctagtggct gtattgaggc cccatgggtg
2461 ttatccctcc attggttcta gtttggaaca gaaaaatctg ttgtattcat ggctttcacc
```

Fig. 1B-1

```
2521 tggctaatac tgagctaagt taccaccagg ttgcaaactc caggacatta ttgtcctgag
2581 ctgcctattc ccttgctggt gcgttgtgga accctgtatt attagttcca gtcctggagg
2641 cctgcctcct gagtttccca gctagttggg acaggcccca atatcccttc ttcctgtaac
2701 ccaaacagtc atgaatttgc tttggcaggt ggatggagac ttgggaactt ccacctcacc
2761 cactaagcca ggcccaggct atggggcatt gtgctaacc ccaccaggtg gatacttggt
2821 ctgaggacgc atcttattct gggcctttag ggagctaagg cagtgagaat tggcaggagg
2881 actgctgtga atgccttgta ggtcggggga ttgaggggg tcctctgctc cctgtctctc
2941 aggatggcaa tgtacctctc accccagtg tcagctgagg taggatccat aatcagtaat
3001 attcctgcaa caaatgttc ctaagtggaa tcaatgaaga ccaaaattta tttgtataac
3061 aactctaaac ctgctctgct ctgctgtgtt tacaatgtgc tttgtgatca tccagcccag
3121 ggagtcccag tctctggctg tctatctgct ctaaggaaga gagcccacag ttctctatag
3181 tgccatagtc tgtgatgaat aaagttccag atttgaggtc aaccccgac caccccttaaa
3241 gtgcttgttg gtctcctact ttggtttgtc ttcagcatcc aactgatgca catttgtcaa
3301 gaacccactg aggctagaaa cccccaaac actcaaggta ccttgagaac atgtatccca
3361 agacctgcaa agaccaaaca catggcctgt aactacttt cactttcaag ccctggaact
3421 tgtctgtacc aaaaatcttt ctgaaccatt caccaaatct cttgtcaagg gccagaataa
3481 attaagagat tggcttttgg ttttcaatta ggctttcaag tcctaagccc aacccctcct
3541 atcccaccta ggcagaaatc acttcagatc cttgcttcct agtttaattt cttctctgcc
3601 tcagttataa catccataaa atggaaataa taatacccac ctcacacagg ggttaggagt
3661 gtttttttgt tggttttttt ccagacaggg tctcactctg tctcccaggc tggagtgcag
3721 tggcacaatc tcggctcact gtaccctccg cctcccaggt tcaagcagtt ctcatgcctc
3781 agcctcccaa gtagctggga ttacaggtgc ctgccaccac gcccggctaa ttttgtatt
3841 aatagagaca gggtttcacc gtgttggca ggctggtcct gaactcctga cctcaagtga
3901 tccacccgcc tcggcctccc aaagtgctgg gattacaggc gtgagccacc acacctggcc
3961 taggagttaa gagtattaaa tgttaagaac agaccaagtc catcaaacag ctccacaccc
4021 ttgttccatg ttctggattg gggagttgtg ggggtggagg tgtagaactt taaaaagct
4081 tcttaaaata agttgctgtg aatacttcag gtatataaaa aaacattggt tgacaataag
4141 ccagtgttct gccattctta cctgcttatc aagacaaaac ctgctcaagt ccctgcccag
4201 ctgcattcca agtgttttca agtttggtgg taagacctga cctgaggctt cttataacct
4261 ttactcagtg ggaatatgca tacagttcac tacagaaata tttgtattta cttagaggaa
4321 gtgccctgga tctggggcg gggggggcg ggggaatgg gtcttttcta aattgttaaa
4381 agcagttcat gccattattc ttaataaaca tttctaatat gctgtgaaag ag
```
(SEQ ID NO: 2)

*Fig. 1B-2*

```
hpipdsspll qfggqvrqry lytddaqqte ahleiredgt vggaadqspe
sllqlkalkp gviqilgvkt srflcqrpdg alygslhfdp eacsfrelll
edgynvyqse ahglplhlpg nksphrdpap rgparflplp glppalpepp
gilapqppdv gssdplsmvg psqgrspsya s (SEQ ID NO: 3)
```

*Fig. 2A*

```
hpipdsspll qfggqvrqry lytddaqqte ahleiredgt vggaadqspe
sllqlkalkp gviqilgvkt srflcqrpdg alygslhfdp eacsfrelll
edgynvyqse ahglplhlpg nksphrdpap rgparflplp glppappepp
gilapqppdv gssdplsmvg psqgrspsya s (SEQ ID NO: 4)
```

*Fig. 2B*

```
mdsdetgfeh sglwvsvlag lllgacqahp ipdsspllqf ggqvrqryly
tddaqqteah leiredgtvg gaadqspesl lqlkalkpgv iqilgvktsr
flcqrpdgal ygslhfdpea csfrellled gynvyqseah glplhlpgnk
sphrdpaprg parflplpgl ppalpeppgi lapqppdvgs sdplsmvgps
qgrspsyas  (SEQ ID NO: 5).
```

*Fig. 2C*

```
   dsspll qfggqvrqry lytddaqqte ahleiredgt vggaadqspe
sllqlkalkp gviqilgvkt srflcqrpdg alygslhfdp eacsfrelll
edgynvyqse ahglplhcpg nksphrdpap rgpcrflplp glppappepp
gilapqppdv gssdplamvg psqgrspsya s (SEQ ID NO: 6)
```

*Fig. 2D*

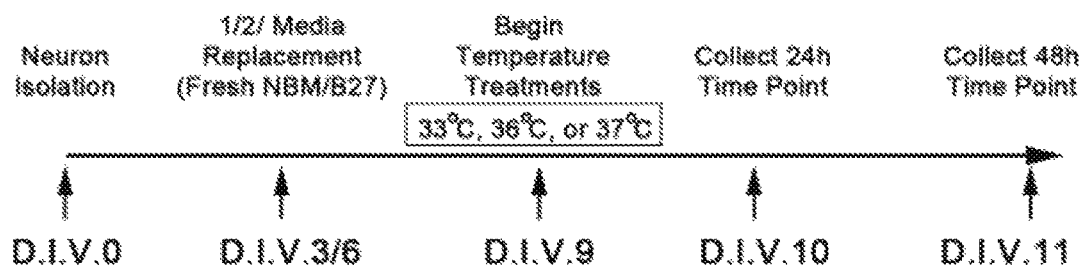
*Fig. 3A*
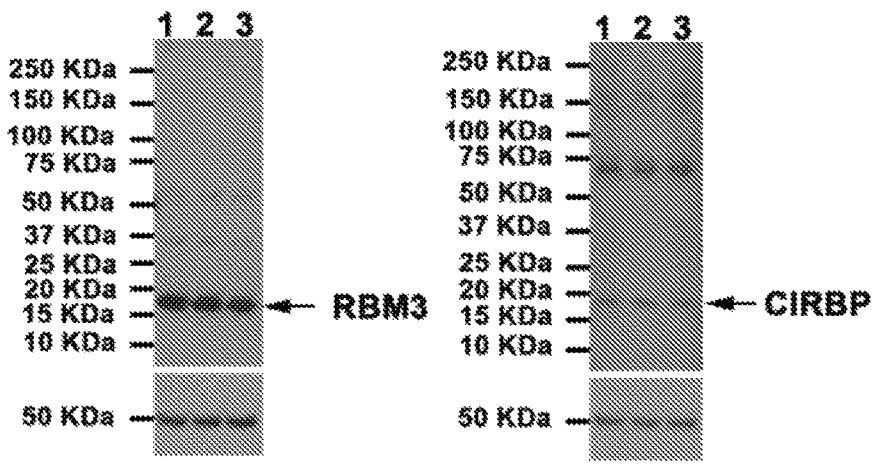
*Fig. 3B*  *Fig. 3C*
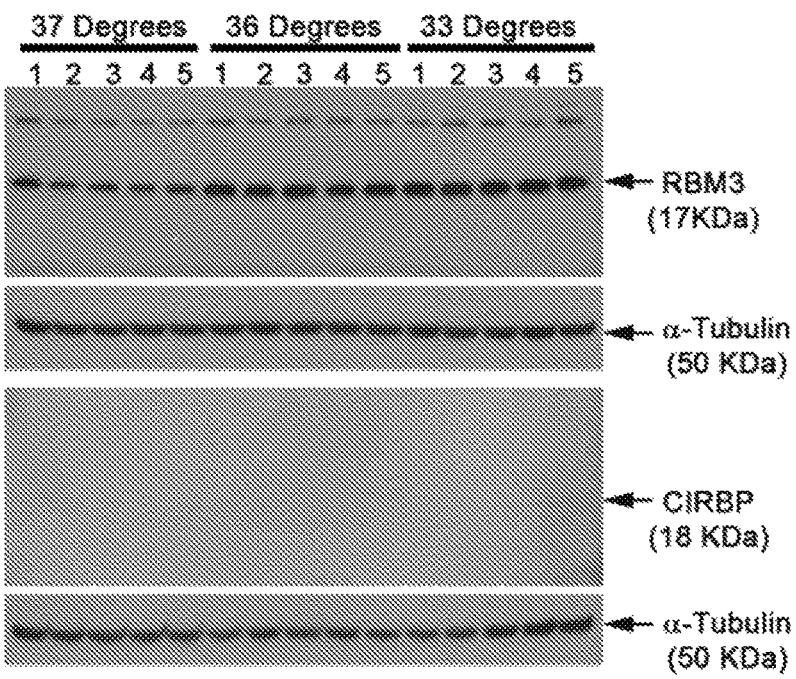
*Fig. 3D*

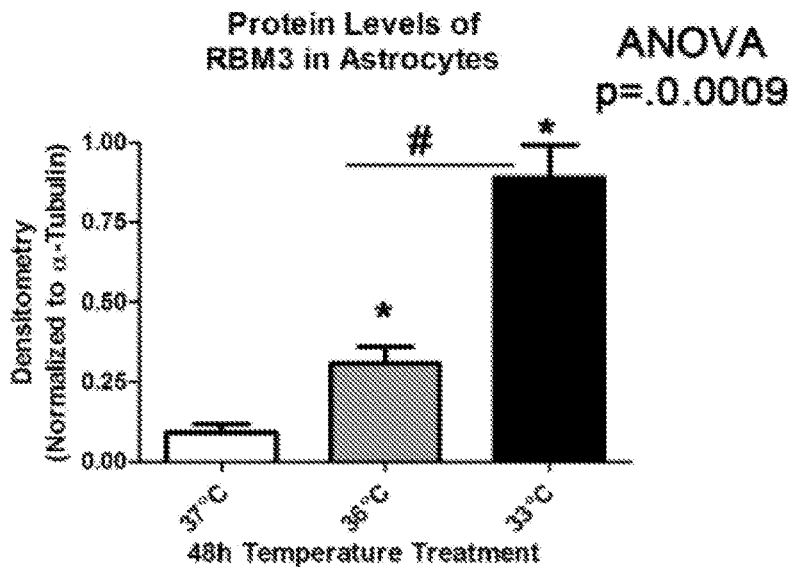
Fig. 5D
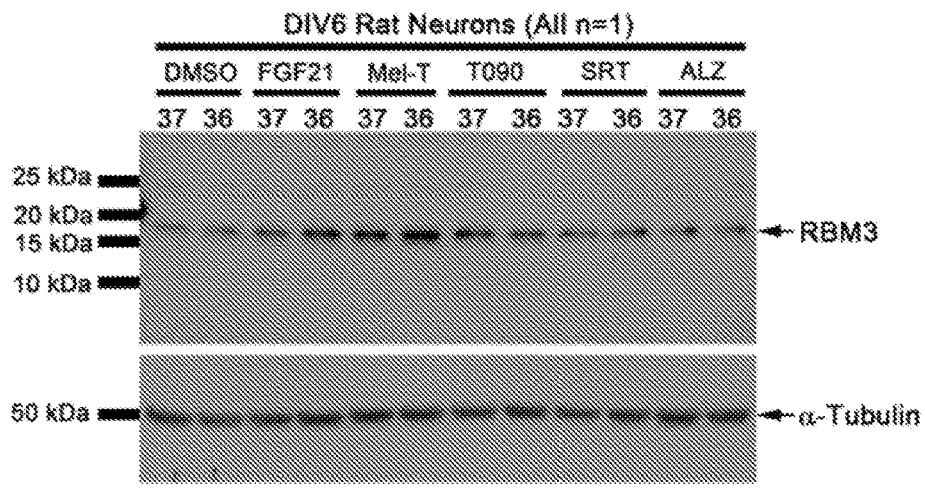
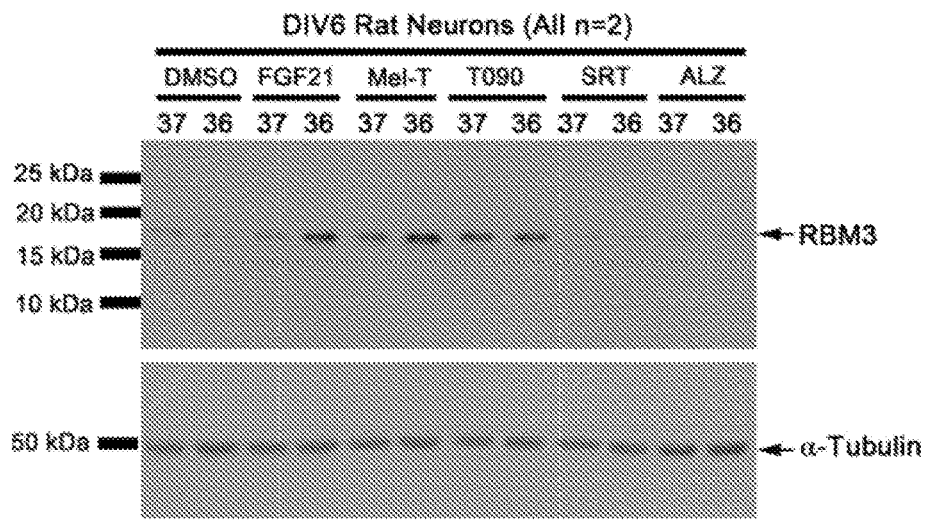
Fig. 6A

Ipsilateral Hippocampal Homogenates

Ipsilateral Hippocampal/Cortical Homogenates

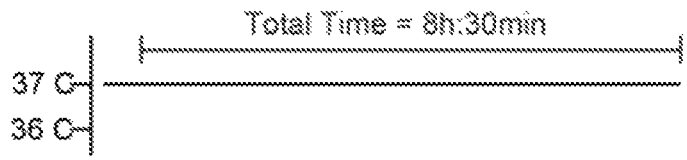
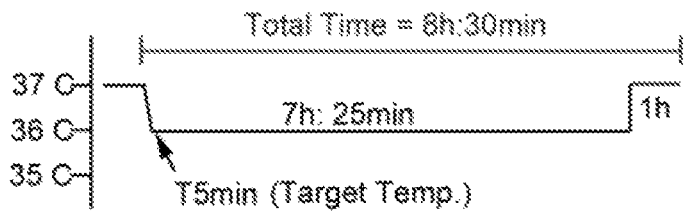
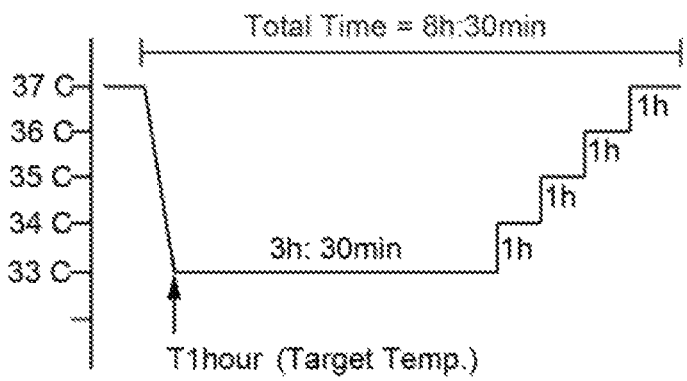
Fig 11A
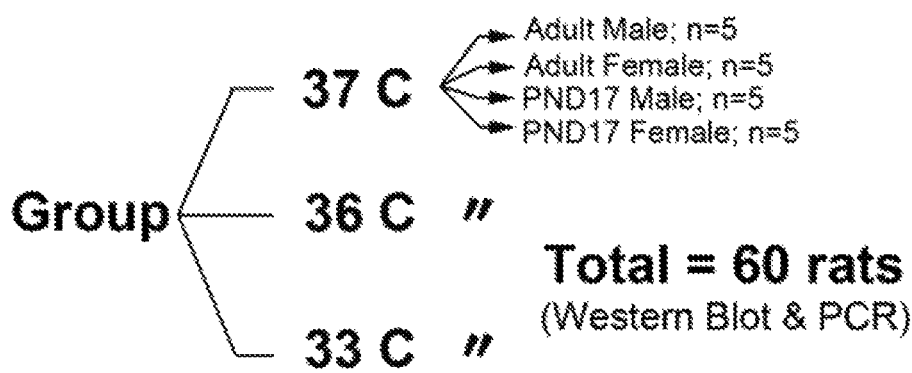
Fig. 11B

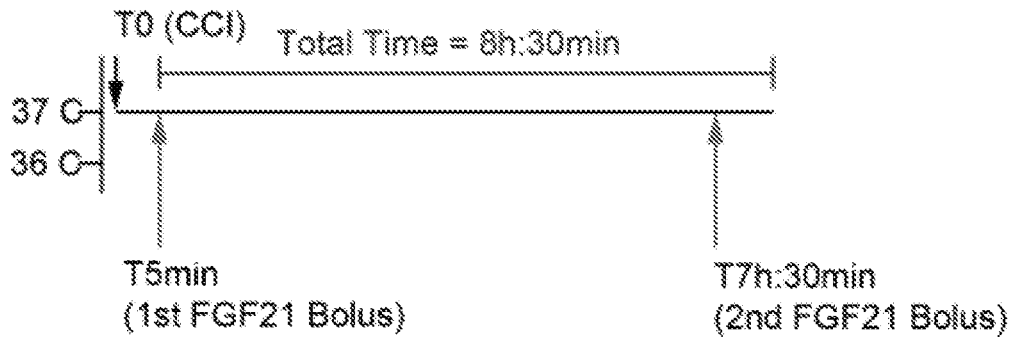
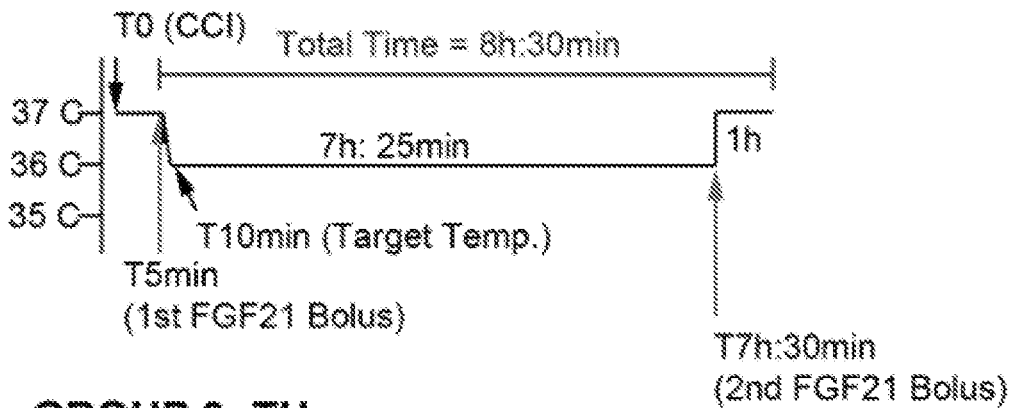
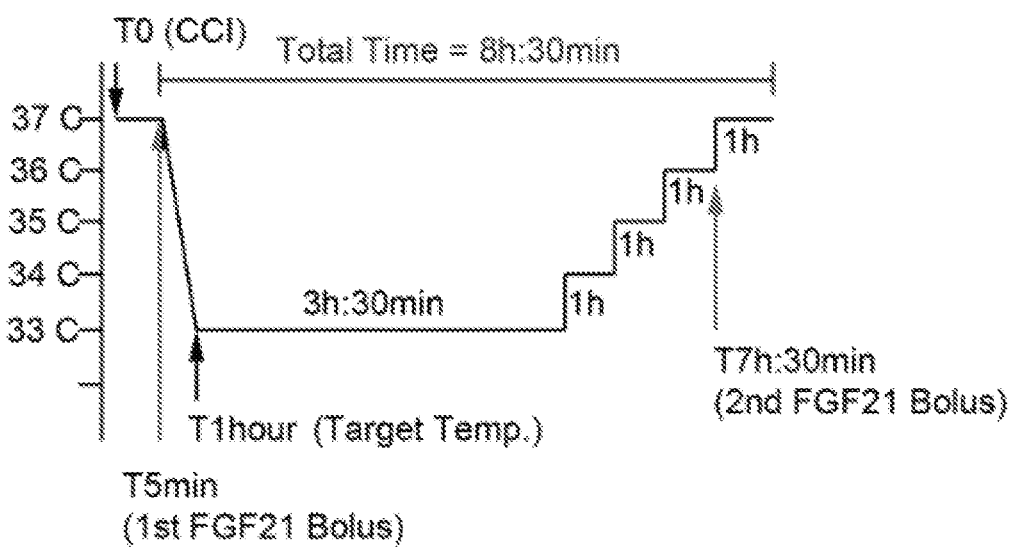
*Fig 12A*

METHOD TO IMPROVE NEUROLOGIC OUTCOMES IN TEMPERATURE MANAGED PATIENTS

CROSS REFERENCE TO RELATED APPLICATIONS

This application is a national stage of International Patent Application No. PCT/US2016/033563, filed May 20, 2016, which claims the benefit of U.S. Provisional Patent Application No. 62/164,205, filed May 20, 2015, each of which is incorporated herein by reference in its entirety.

STATEMENT REGARDING FEDERAL FUNDING

This invention was made with government support under Grant No. 1R21NS088145 awarded by the National Institutes of Health, and Grant No. W81XWH-10-1-0623 awarded by the U.S. Army. The government has certain rights in the invention.

Hypothermia has long been known to have protective and detrimental effects depending on depth and duration. For CNS injury, therapeutic hypothermia (TH) is one of the most successful therapies to treat neurological impairment. The optimal target temperature and rate of rewarming to maximize neuroprotection remains a matter of debate. Each 1° C. reduction in body temperature decreases cerebral metabolism and blood flow by ~6%. Cooling at or below 35.5° C. (but above deep hypothermia) inversely correlates with greater neuroprotection. In contrast, extremely mild hypothermia to 36° C. is not thought to appreciably affect neuroprotection or activate hypothermia-regulated mechanisms. It has also been used as normothermic control in a number of brain injury studies.

Traumatic brain injury (TBI) is a leading cause of death and disability worldwide. Therapies to reduce CNS impairment in surviving patients are severely lacking. Fever is common after TBI, and is strongly associated with unfavorable outcomes. Elevation in temperature by 1° C. worsens neurologic recovery after injury. Also, induced hyperthermia to 39° C. unmasks latent cognitive deficits after mild TBI. Fever prevention (TTM) is recommended for acute brain injury and standard of care in severe TBI. Goal temperatures vary across studies (37-35.5° C.). TTM is typically achieved by antipyretics/icepacks or intravascular cooling devices. TBI patients may also benefit from TTM by reduction in intracranial pressure (ICP). A key limitation of TTM is that it lacks direct neuroprotective effects occasionally seen by deeper levels of cooling in some patients or age groups (e.g. neonates).

Mild therapeutic hypothermia (TH) ranges from 32-35° C. Until recently, it was the putative therapy for comatose out-of-hospital cardiac arrest (OOHCA) in adults. Use of TH for brain ischemia has a long history traced back to early case reports of drowning victims in ice cold water having miraculous neurologic recovery. A surge of pre-clinical studies later identified numerous mechanisms mediating protection by hypothermia including: decreased glutamate, decreased metabolism/ATP consumption, decreased oxygen radicals, inhibition cell death mediators, activation of beneficial proteins, decreased neuroinflammation, and reduced ICP (in TBI). Despite these benefits, hypothermia has largely failed to translate in adult/pediatric severe TBI. Furthermore, recent clinical trials are challenging the notion TH to 33° C. is better than fever control to ~36° C. in adults/children with OOHCA (a cohort believed to benefit most from TH). There are many explanations why TH is not as efficacious in humans vs. other animals. Species differences, varied levels of experience administering TH across clinics, trial design limitations, duration of cooling, time to target temperature, rate of re-warming, and inherent heterogeneity of human populations are but a few of the potential confounders. Also, TH can produce side effects like infection and requires careful management of altered physiology like hyperglycemia (usually treated with insulin), ion disturbances (e.g. hyperkalemia), shivering (controlled with sedatives and/or neuromuscular blockers), and acid-base changes. These are a few of the risks. Nevertheless, TH is felt to have potential benefits on neurological outcome which may outweigh the risks, particularly in neonatal brain injury.

Therapeutic Hypothermia (TH) and Targeted Temperature Management (TTM) are clinically used therapies for managing patients who may be exposed, or were exposed to a brain injury. Adults and children treated with "fever prevention" using targeted temperature management (TTM) to ~36° C. have similar neurologic outcomes vs. patients treated with therapeutic hypothermia (TH) to 33° C. after cardiac arrest or traumatic brain injury (TBI). Trials broadly support the use of rigorous fever control rather than TH for acute brain injury (except in neonates where TH is highly neuroprotective). An advantage of TTM vs. TH is less adverse side effects. A disadvantage is that TTM fails to activate neuroprotective mechanisms induced by cooler temperatures. A major unmet medical need is to develop therapies that make TTM directly neuroprotective, or that make TH in adults/children consistently neuroprotective as in neonates with hypoxic ischemic encephalopathy, while minimizing side effects.

Cold shock proteins are up-regulated by cold stress. They include RNA binding motif 3 (RBM3) and cold-inducible response binding protein (CIRBP). CIRBP is a novel damage associated molecular pattern (DAMP) and induces a pro-inflammatory response in mice. Also, CIRBP knockouts (Kos) are protected from ischemic brain injury. In contrast RBM3 is protective.

Hibernating animals endure enormous levels of cold stress. Arctic ground squirrels tolerate periods of core body temperature as low as minus 2.0° C. during hibernation. Larger mammals like bears tolerate sustained periods of 30.0° C. A key feature both species share in common is hibernation induces RBM3—a central effector of the adaptive cold-stress response. RBM3 expression increases in brain, heart, liver, and muscle in hibernating adults. RBM3 modifies energy homeostasis helping the body adapt to cold stress. Possibly one of its most important (known) functions is to potently stimulate cellular global protein synthesis (GPS). It is believed that the RBM3-GPS axis evolved to counteract profound decreases in protein translation caused by hypothermia. Germane to these effects, RBM3 is also robustly neuroprotective. In mice, brief exposures to deep hypothermia cause sustained increases in brain levels of RBM3 which in turn prevents neurodegeneration caused by prion or Alzheimer's pathology (Peretti D, et al. RBM3 mediates structural plasticity and protective effects of cooling in neurodegeneration. *Nature*. Feb. 12, 2015; 518(7538): 236-239). RBM3 has major protective CNS effects in non-hibernating species like mice (Peretti et al.). Deep cooling to 16° C. for 45 minutes caused sustained increases in brain RBM3 levels days after a single exposure. Mice infected with prions (to induce neurodegeneration) or having Alzheimer's disease (AD) were profoundly protected by this transient deep hypothermia exposure which prevented neuronal death, increased synaptic number and function, improved learning and memory, and reduced mortality (in prion disease). All benefits (even on mortality) were blocked by lentivirus mediated RBM3 RNAi. Furthermore, RBM3 overexpression in normothermic mice mimicked the benefits of deep cooling.

Furthermore, RBM3 RNA interference (RNAi) prevents neuroprotection by mild TH (32° C.) in vitro (Chip S, et al. (2011) The RNA-binding protein RBM3 is involved in hypothermia induced neuroprotection (*Neurobiol Dis* 43:388-396). Levels also increase in organotypic hippocampal slices cooled to 33.5° C. (Tong G, et al. (2013) Effects of moderate and deep hypothermia on RNA-binding proteins RBM3 and CIRP expressions in murine hippocampal brain slices (*Brain Res* 1504:74-84).

As indicated above, RBM3 is a powerful inducer of global protein synthesis (GPS) in vitro and this was recently confirmed in vivo (Peretti D, et al. *Nature*. Feb. 12 2015; 518(7538):236-239). Thus it can cause widespread biochemical changes that alter cell functions. One study investigated if very mild hypothermia upregulates cold stress proteins; long-term maintenance of embryonic stem cells to 35° C. failed to increase RBM3/CIRBP mRNA (Belinsky G S, et al. (2013) Mild hypothermia inhibits differentiation of human embryonic and induced pluripotent stem cells (*Biotechniques* 55:79-82).

There is a need for effective treatments in chronic neurodegenerative diseases like dementia, Alzheimer's disease, and prion disease, as well as in acute brain injury (e.g. such as ischemic pathologies or TBI). In the setting of acute neurocritical care, there is a major need to improve clinical outcomes by increasing the neuroprotective efficacy and safety of body/organ cooling (aka therapeutic hypothermia) in temperature-managed patients kept below 37° C. There also is a need for methods of preventing delayed graft function, for example in kidney patients.

SUMMARY

Described herein is the administration of certain compositions to hypothermic patients, e.g. patients having a temperature ranging from 5° C. to less than 36.5° C., or patients under very mild hypothermia, above 33° C. and below 37° C., for example from 34° C. to 36.5° C., or from 35.5° C. to 36.5° C., e.g., 36° C., results in enhanced production of RBM3 in the brains and body of those patients, resulting in protective effects, including a neuroprotective effects. RBM3 is produced under sufficiently hypothermic conditions, but not typically under very mild hypothermia. These compositions, include, for example, a fibroblast growth factor 21.

Therefore in one aspect a method of improving brain function in a hypothermic patient is provided. The method comprises administering to the patient an amount of a fibroblast growth factor 21 (FGF21) protein effective to increase RNA binding motif 3 (RBM3) production in nerve cells of the patient. According to one aspect, the method further comprises inducing hypothermia in the patient prior to, during or after administration of the FGF21 protein to the patient, and optionally the FGF21 protein is administered up to 48 h before hypothermia is induced, at the induction of hypothermia, or up to 48 h after hypothermia is concluded. In various aspects, the FGF21 protein is human FGF21 or a functional FGF21 mutant protein, such as LY2405319, or PF-05231023, which is an example of a functional FGF21 mutant protein comprising an FGF21 protein or mutant protein conjugated to an antibody or a fragment thereof, and optionally the antibody or fragment thereof lacks an antigen-binding site or it lacks an antigen binding site that binds a native human epitope. In one aspect, the patient is a neonate (within 28 days of birth) or a pediatric patient (less than 18 years of age), in another, the patient suffers from mild/moderate/severe traumatic brain injury (TBI), ventricular fibrillation cardiac arrest (VFCA), subarachnoid hemorrhage (SAH), subdural hematoma (SH), cerebral vasospasm, neonatal abusive head trauma (a.k.a. shaken baby syndrome), neonatal hypoxic ischemic encephalopathy (HIE), asphyxia cardiac arrest (ACA), treatment of spinal injury, prophylaxis in spinal surgery, stroke, and drug overdose, and in yet another, the patient is or will be undergoing cardiac surgery, spinal surgery, deep hypothermia circulatory arrest (DHCA), transplantation, or is subject to an emergency preservation and resuscitation (EPR) method. The hypothermic patient's body temperature is maintained at a temperature ranging from 5° C. to 36.5° C., from 5° C. to 10° C., from 11° C. to 29° C., from 28° C. to 32° C., from 33° C. to 35.5° C., from above 33° C. and below 37° C., from 34° C. to 36.5° C., from 35.5° C. to 36.5° C., or 36° C. Hypothermia may be induced and maintained by any useful method, for example by mechanical or pharmacological cooling, for example, in one aspect, the patient's body temperature is reduced and/or maintained at least in part by one or more mechanical cooling devices, such as an ice pack, a fan, a circulating water blanket, a circulating cold air blanket, hydrogel-coated pads, a cooling helmet, a heat-exchange catheter, an extracorporeal heat exchange, intravenous/intravascular infusion of cooled normal saline or lactated Ringers solution, and heat-exchange by percutaneous indwelling lines, and in another aspect, patient's hypothermic body temperature is initiated or maintained at least in part by administering a pharmacologic agent effective to lower a patient's body temperature, such as but not limited to anesthetics like isoflurane, sevoflurane, desflurane, halothane, propofol, fentanyl, morphine, opioids, and adenosine monophosphate, such as 5-AMP, 3-AMP, or 2-AMP, N-(2-aminoethyl)-N-(4-(benzyloxy)-3-methoxybenzyl)thio-phene-2-carboxamide hydrochloride (M8-B), or melatonin. The FGF21 protein is administered in any useful manner, for example and without limitation, the FGF21 protein is delivered by intravenous, oral, intranasal, inhalation, intrathecal, or intracerebroventricular route. The FGF21 is maintained in the hypothermic patient's body in an effective amount to increase RNA binding motif 3 (RBM3) production in nerve cells of the patient for at least 0.5, at least 1, at least 12, or at least 24 hours. In one aspect, the amount of FGF21 protein effective to increase RNA binding motif 3 (RBM3) production in nerve cells of the patient ranges from 1 pg/kg to 500 mg/kg, or 5-300 nanomolar. In one aspect the FGF21 protein is administered as a bolus, at multiple time points, or as a continuous infusion/release, and optionally is provided in a composition used to infuse a patient to establish and/or maintain hypothermia.

In another aspect, a method of inducing RBM3 in a nerve cell is provided. The method comprises contacting the nerve cell with an amount of an FGF21 protein effective to increase RNA binding motif 3 (RBM3) production in a nerve cell under a hypothermic condition. In various aspects, the FGF21 protein is human FGF21 or a functional FGF21 mutant protein, such as LY2405319, or PF-05231023, which is an example of a functional FGF21 mutant protein comprising an FGF21 protein or mutant protein conjugated to an antibody or a fragment thereof, and optionally the antibody or fragment thereof lacks an antigen-binding site or it lacks an antigen binding site that binds a native human epitope.

The hypothermic condition is maintained at a temperature ranging from 5° C. to 36.5° C., from 5° C. to 10° C., from 11° C. to 29° C., from 28° C. to 32° C., from 33° C. to 35.5° C., from above 33° C. and below 37° C., from 34° C. to 36.5° C., from 35.5° C. to 36.5° C., or 36° C. Hypothermia may be induced and maintained by any useful method, for example by mechanical or pharmacological cooling, for example, in one aspect, for a nerve cell of a patient, the patient's body temperature is reduced and/or maintained at least in part by one or more mechanical cooling devices, such as an ice pack, a fan, a circulating water blanket, a circulating cold air blanket, hydrogel-coated pads, a cooling helmet, a heat-exchange catheter, an extracorporeal heat exchange, intravenous/intravascular infusion of cooled normal saline or lactated Ringers solution, and heat-exchange by percutaneous indwelling lines, and in another aspect, patient's hypothermic body temperature is initiated or maintained at least in part by administering a pharmacologic agent effective to lower the patient's body temperature, such as but not limited to anesthetics like isoflurane, sevoflurane, desflurane, halothane, propofol, fentanyl, morphine, opioids, and adenosine monophosphate, such as 5-AMP, 3-AMP, or 2-AMP, N-(2-aminoethyl)-N-(4-(benzyloxy)-3-methoxybenzyl)thiophene-2-carboxamide hydrochloride (M8-B), or melatonin. When provided to a patient, the FGF21 protein is administered in any useful manner, for example and without limitation, the FGF21 protein is delivered by intravenous, oral, intranasal, inhalation, intrathecal, or intracerebroventricular route. The FGF21 is maintained in a hypothermic patient's body in an effective amount to increase RNA binding motif 3 (RBM3) production in nerve cells of the patient for at least 0.5, at least 1, at least 12, or at least 24 hours. In one aspect, the amount of FGF21 protein effective to increase RNA binding motif 3 (RBM3) production in nerve cells from 1 pg/kg to 500 mg/kg in a patient, or 5-300 nanomolar in a patient or in vitro. In one aspect the FGF21 protein is administered to a patient as a bolus, at multiple time points, or as a continuous infusion/release, and optionally is provided in a composition used to infuse a patient to establish and/or maintain hypothermia.

In another aspect, an FGF21 protein for use in treatment of mild/moderate/severe traumatic brain injury (TBI), ventricular fibrillation cardiac arrest (VFCA), subarachnoid hemorrhage (SAH), subdural hematoma (SH), cerebral vasospasm, neonatal abusive head trauma (a.k.a. shaken baby syndrome), neonatal hypoxic ischemic encephalopathy (HIE), asphyxia cardiac arrest (ACA), treatment of spinal injury, prophylaxis in spinal surgery, stroke, and drug overdose, or where a patient is or will be undergoing cardiac surgery, spinal surgery, deep hypothermia circulatory arrest (DHCA), transplantation, or is subject to an emergency preservation and resuscitation (EPR) method, wherein the patient is hypothermic. In various aspects, the FGF21 protein is human FGF21 or a functional FGF21 mutant protein, such as LY2405319, or PF-05231023, which is an example of a functional FGF21 mutant protein comprising an FGF21 protein or mutant protein conjugated to an antibody or a fragment thereof, and optionally the antibody or fragment thereof lacks an antigen-binding site or it lacks an antigen binding site that binds a native human epitope. In one aspect, the patient is a neonate (within 28 days of birth) or a pediatric patient (less than 18 years of age). The hypothermic patient's body temperature is maintained at a temperature ranging from 5° C. to 36.5° C., from 5° C. to 10° C., from 11° C. to 29° C., from 28° C. to 32° C., from 33° C. to 35.5° C., from above 33° C. and below 37° C., from 34° C. to 36.5° C., from 35.5° C. to 36.5° C., or 36° C. Hypothermia may be induced and maintained by any useful method, for example by mechanical or pharmacological cooling, for example, in one aspect, the patient's body temperature is reduced and/or maintained at least in part by one or more mechanical cooling devices, such as an ice pack, a fan, a circulating water blanket, a circulating cold air blanket, hydrogel-coated pads, a cooling helmet, a heat-exchange catheter, an extracorporeal heat exchange, intravenous/intravascular infusion of cooled normal saline or lactated Ringers solution, and heat-exchange by percutaneous indwelling lines, and in another aspect, patient's hypothermic body temperature is initiated or maintained at least in part by administering a pharmacologic agent effective to lower a patient's body temperature, such as but not limited to anesthetics like isoflurane, sevoflurane, desflurane, halothane, propofol, fentanyl, morphine, opioids, and adenosine monophosphate, such as 5-AMP, 3-AMP, or 2-AMP, N-(2-aminoethyl)-N-(4-(benzyloxy)-3-methoxybenzyl)thiophene-2-carboxamide hydrochloride (M8-B), or melatonin. The FGF21 protein is administered in any useful manner, for example and without limitation, the FGF21 protein is delivered by intravenous, oral, intranasal, inhalation, intrathecal, or intracerebroventricular route. The FGF21 is maintained in the hypothermic patient's body in an effective amount to increase RNA binding motif 3 (RBM3) production in nerve cells of the patient for at least 0.5, at least 1, at least 12, or at least 24 hours. In one aspect, the amount of FGF21 protein effective to increase RNA binding motif 3 (RBM3) production in nerve cells of the patient ranges from 1 pg/kg to 500 mg/kg, or 5-300 nanomolar. In one aspect the FGF21 protein is administered as a bolus, at multiple time points, or as a continuous infusion/release, and optionally is provided in a composition used to infuse a patient to establish and/or maintain hypothermia.

BRIEF DESCRIPTION OF THE DRAWINGS

FIGS. 1A and 1B provide exemplary amino acid and nucleotide (cDNA) sequences for human RBM3 (SEQ ID NOS: 1 and 2, respectively).

FIGS. 2A-2D provide amino acid sequences for FGF21 proteins (SEQ ID NOS: 3-6).

FIGS. 3A-3G: Mild Hypothermia Increases RBM3 in DIV10-11 Neurons. (FIG. 3A) Timeline of experimental procedures. (FIG. 3B) Western blot showing specificity of antibodies to detect RBM3 and (FIG. 3C) CIRBP in neurons given 33° C. hypothermia for 48 h. (FIG. 3D) Western blot show increased RBM3 but not CIRBP in primary cortical neurons treated 24 h or (FIG. 3E) 48 h with hypothermia. (FIG. 3F) Densitometry of protein changes for RBM3 (n=5/group) at 24 h and (FIG. 3G) 48 h (n=5/group). Multiple comparisons were analyzed by one-way-ANOVA and Newman-Keuls post-hoc. Data were significant at $p<.05$. (*) indicates post-hoc significant difference compared to 37° C. normothermia (#) indicates post-hoc significant difference comparing UMH to mild hypothermia. Graphs show mean+SEM.

(FIG. 4A) Timeline of experimental procedures. (FIG. 4B) 20 µg protein was loaded onto gels. Western blot show increased RBM3 in primary cortical neurons treated 48 h with hypothermia and subjected to 1 h re-warm in conditioned media (C.M.) or (FIG. 4C) fresh neurobasal B27 supplement (NBM/B27). (FIG. 4D) Densitometry of RBM3 protein changes in neurons treated with hypothermia for 48 h (n=3/group) and then re-warmed in C.M. or (FIG. 4E) Fresh NBM/B27. Multiple comparisons were analyzed by one-way-ANOVA and Newman-Keuls post-hoc. (FIG. 4F) Western blot shows validation of SUnSET and effect of fresh media exchange on protein translation at 37° C. Negative control (no puromycin; NP) are ARA-C treated DIV6 neuron homogenates. Neuron homogenates incubated with puromycin for 30 min stain positive with anti-puromycin antibody indicating level of de novo protein synthesis. (FIG. 4G) Level of puromycin staining in neurons treated with hypothermia and rewarmed 1 h in C.M. or (FIG. 4H) NBM/B27. (FIG. 4I) Western blot show increased phosphorylation of eIF2α in neurons treated with hypothermia. (FIG. 4J) Densitometry of phosphorylation of eIF2α levels, normalized to eIF2α total, in hypothermia treated neurons (n=3/group). Data were significant at p<.05. (*) indicates post-hoc significant difference compared to 37° C. normothermia (#) indicates post-hoc significant difference comparing UMH to mild hypothermia. Graphs show mean+SEM.

FIGS. 5A-5D: Mild Hypothermia Increases RBM3 in Rat Astrocytes. (FIG. 5A) Timeline of experimental procedures. Western blots (20 μg/well) showing eIF2α and RBM3 changes in astrocytes given 37° C., 36° C., or 33° C. for hypothermia for (FIG. 5B) 24 h and (FIG. 5C) 48 h. (FIG. 5D) Densitometry of protein changes for RBM3 (n=3/group) at 48 h. Data were transformed to log(Y) for analysis. Multiple comparisons were analyzed by one-way-ANOVA and Newman-Keuls post-hoc. Data were significant at p<.05. (*) indicates post-hoc significant difference compared to 37° C. normothermia (#) indicates post-hoc significant difference comparing UMH to mild hypothermia. Graphs show mean+SEM.

FIGS. 6A-6F: FGF21 and Melatonin augment RBM3 induction in young neurons. (FIG. 6A) Western blots (n=2) show effect of 24 h treatment of DIV6 neurons with 5 nM FGF21, 100 μM melatonin, 1 μM T090, 5 μM SRT1720, or 1 μM AZD1080. (FIG. 6B) Western blots show dose effect of 24 h FGF21, melatonin, or T090 at 37° C. on RBM3 levels in DIV7 neurons. (FIG. 6C) Western blot shows dose effect of 24 h FGF21 at 36° C. on RBM3 levels in DIV7 neurons. (FIG. 6D) Western blots show the effect of FGF21 on AKT and ERK activation. (FIG. 6E) Western blots show effect of 24 h treatment combinations (n=3/group) to induce RBM3 in DIV7 neurons cooled to 36 C. FGF21 was applied at 50 nM, melatonin 100 μM, and T090 at 1 μM. (FIG. 6F) Western blots show effect of 48 h treatment combinations to induce RBM3 in DIV26 neurons cooled to 36° C. or 33° C. FGF21 was applied at 50 μM, melatonin 100 μM, and T090 at 1 μM (n=3/group).

FIGS. 11A and 11B illustrate exemplary protocols for groups according to Example 4.

DETAILED DESCRIPTION

Figure 3E:
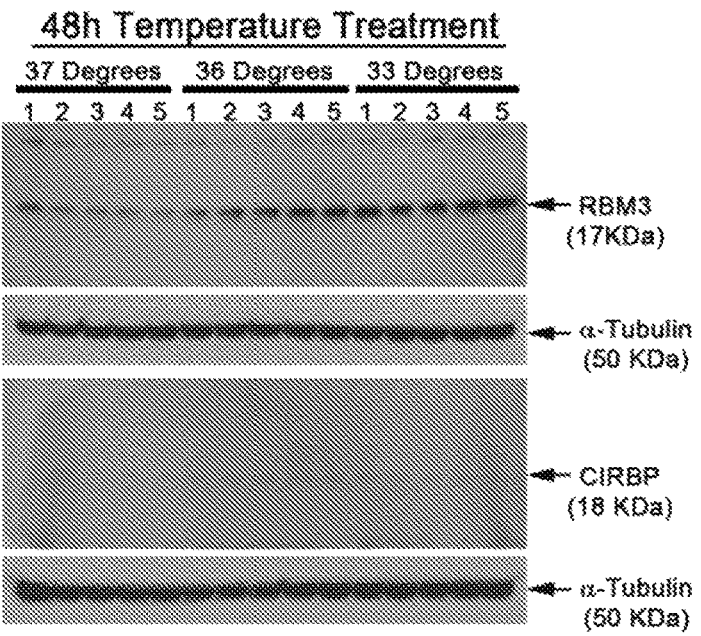

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts. "A" or "an" refers to one or more.

RBM3-inducing compounds are described herein, which induce RBM3 at hypothermic temperatures (i.e. temperatures less than 37° C. (degrees Celsius). These agents are useful for neurological protection during clinical temperature management. RBM3 inducers have not been previously identified. Fibroblast growth factor 21 (FGF21) induces RBM3 in young neurons, when cooled below 37° C. These findings suggests that FGF21 has superior protective actions in cooled patients. This has broad implications for use of FGF21 in the setting of therapeutic hypothermia/targeted temperature management in critically ill patients, for example in neonates and pediatric patients.

Therefore, provided herein according to one aspect of the invention is a method of improving brain function in a hypothermic patient. The method comprises administering to the patient an amount of a fibroblast growth factor 21 (FGF21) effective to increase RNA binding motif 3 (RBM3) production in nerve cells of the patient. In one aspect, the hypothermic patient is a neonate (age up to 28 days full term, including premature infants), a pediatric patient, a patient undergoing nerve regeneration, a transplant recipient, a pregnant patient or any patient with nascent nerve growth, the method comprising up-regulating RBM3 in the hypothermic patient. Likewise a method of protecting nerve cells under hypothermic conditions (e.g., less than 37° C. or standard culture conditions for the cells/tissue) is provided.

Hypothermic means below normal physiological temperature, e.g., 37° C., for example, ranging from 32° C. to less than 37° C., including patients under very mild hypothermia, that is, above 33° C. and below 37° C., for example from 34° C. to 36.5° C., or from 35.5° C. to 36.5° C., e.g., 36° C.

In further aspects, the hypothermic patient is a patient suffering from (that is, experiencing): mild/moderate/severe traumatic brain injury (TBI), ventricular fibrillation cardiac arrest (VFCA), subarachnoid hemorrhage (SAH), subdural hematoma (SH), cerebral vasospasm, neonatal abusive head trauma (a.k.a. shaken baby syndrome), neonatal hypoxic ischemic encephalopathy (HIE), asphyxia cardiac arrest (ACA), treatment of spinal injury, prophylaxis in spinal surgery, stroke, and drug overdose. In additional aspects, the hypothermic patient is or will be undergoing a medical procedure, such as cardiac surgery or spinal surgery, or is subject to an emergency preservation and resuscitation (EPR) method, for example, as is disclosed in U.S. Pat. No. 8,628,512. EPR methods include the therapeutic induction of a state of tolerance to temporary, complete systemic ischemia (deficiency of blood supply) and are interventional preservation measures for patients/victims who cannot be immediately resuscitated, for example and without limitation, in pre-hospital, hospital and field scenarios. These patients may be prevented from dying by inducing such preservative measures until evacuated to a medical center for emergency medical/surgical intervention and delayed resuscitation can be completed. Another example of a medical procedure which utilizes cooling is deep hypothermia circulatory arrest (DHCA) for surgical correction of congenital defects (e.g. heart abnormalities) in newborns (Ziganshin BA et al., Ann Cardiothorac Surg. 2013 May; 2(3): 303-315.).

By "improving brain function," it is meant improvement in one or more tests to evaluate brain function including, but not limited to: mortality/disability (e.g. Glasgow Coma Scale, Glasgow Outcome Score, Extended-Glasgow Outcome Scale, Modified Rankin Scale), intellect (e.g. Stanford Binet Intelligence Scale, Wechsler Adult Intelligence Scale, Woodcock-Johnson III), motor function (e.g. grip strength, balance, timed walk test), memory (e.g. Wechsler Memory Scale), attention (Test Of Variables of Attention, Conners' Continues Performance Test-II), vision (e.g. Beery-Buktenica Developmental Test of Visual-Motor Integration, Bender Visual-Motor Gestalt Test), emotional status/social skills (e.g. Vineland Adaptive Behavior Scale, Hamilton Rating Scale for Depression), executive function (e.g. Delis-Kaplan Executive function System), brain imaging and monitoring (e.g. Electroencephalography, Head Computed Tomography, Magnetic Resonance Imaging, Positron Emission Tomography, Neurosonography, X-Rays, Intracranial Pressure Monitoring), serum and cerebral spinal fluid biomarkers (e.g. proteins such as GFAP, S-100B, NSE, HMGB1), quality of life, (e.g. Quality of Life after Brain Injury Score), cellular homeostasis (e.g. Increased Global Protein Synthesis).

Hypothermia is induced (started) and maintained. Hypothermia may be induced and maintained by the same or different methods or by use of more than one method simultaneously for either or both induction and maintenance. Non-limiting examples of methods useful in inducing and/or maintaining hypothermia include: mechanical cooling devices, such as an ice pack, a fan, a circulating water blanket, a circulating cold air blanket, hydrogel-coated pads (e.g., the Artic Sun® Cooling Blanket/Artic Sun® Temperature Management System, from Medviance®, of Louisville, Colo.), a cooling helmet, a heat-exchange catheter, an extracorporeal heat exchange, intravenous/intravascular infusion of cooled saline or lactated Ringers solution, and/or heat-exchange by percutaneous indwelling lines.

A "nerve cell," includes any cell of the Central Nervous System and Peripheral Nervous System, including, without limitation, neurons and glial cells, such as neurons, motorneurons, afferent neurons, efferent neurons, interneurons, microglia, and macroglia, and more specifically, pyramidal neurons, Purkinje cells, Dogiel cells, Basket cells, Betz cells, Lugaro cells, Medium spiny neurons, Renshaw cells, unipolar Brush Cells, Granule cells, Anterior Horn cells, spindle cells, astrocytes, protoplasmic astrocytes, fibrous astrocytes, oligodendrocytes, interfascicular oligodendrocytes, ependymal cells, radial glia, Schwann cells, Satellite glial cells, enteric glial cells, ependymal cells, pituicytes, tanycytes, neuronal stem cells, and neuronal precursor cells.

In a further aspect, a method of preparing a kidney for transplantation, to reduce delayed graft function, is provided. The method comprises administering to a kidney donor prior to removal of a kidney an amount of an FGF21 protein, as described in any aspect herein effective to reduce delayed graft function, and subjecting the donor to hypothermic conditions, for example, ranging from 32° C. to less than 37° C., including patients under very mild hypothermia, that is, above 33° C. and below 37° C., for example from 34° C. to 36.5° C., or from 35.5° C. to 36.5° C., e.g., 36° C. It has previously been shown that induction of hypothermia in kidney donors significantly, though not completely, reduced the prevalence of delayed graft function in donated kidneys (Niemann, CU, et al., Therapeutic Hypothermia in Deceased Organ Donors and Kidney-Graft Function (2015) *N Engl J Med* 373:405-14), and it is expected that the benefits of FGF21 augmentation of RMB3 activation as described herein for neurological protection and therapies will be equally effective in kidney transplant cases.

RNA Binding Motif Protein 3 (RBM3, e.g., as disclosed in OMIM 300027; NCBI Gene, Gene ID: 5935; UniProtKB-P98179; and NCBI Reference Sequences: NM_006743 and NP_006734.1 (GenBank)) is a member of the glycine-rich RNA-binding protein family and encodes a protein with one RNA recognition motif (RRM) domain. An exemplary amino acid sequence and cDNA sequence of a human RMB3 is provided in FIGS. 1A and 1B, respectively (SEQ ID NOS: 1 and 2, respectively).

"A fibroblast growth factor 21" or "an FGF21" or "an FGF21 protein" refers to human FGF21 (e.g., as disclosed in OMIM 609436; NCBI Gene, Gene ID: 26291; and NCBI Reference Sequences: NM_019113.2 and NP_061986.1 (GenBank)), as well as "functional FGF21 mutant proteins," referred to herein as FGF21 mutant proteins, which are functional derivatives or analogs of human FGF21 protein that are neuroprotective, for example, which perform essentially as, or better than, the FGF21 protein tested in the examples below in the same assays. Functional FGF21 mutant proteins are broadly-known to those of ordinary skill, for example and without limitation, as disclosed in International Patent Publication No. WO 2010042747, U.S. Pat. Nos. 7,582,607, 8,722,622, each of which is incorporated herein by reference for their technical disclosure, and in United States Patent Publication Nos. 20090305986, 20140228282, and 20140323396, each of which is incorporated herein by reference in its entirety for its disclosure of FGF21 proteins. FGF21 proteins, and FGF21 mutant proteins include FGF21 and mutant FGF21 protein sequences conjugated to another composition, peptide or protein, examples of which include, as are known in the art: polymer-conjugated FGF21 and mutant FGF21 protein sequences, and protein-conjugated FGF21 and mutant FGF21 protein sequences. Polymer-conjugated FGF21 and mutant FGF21 protein sequences include, for example poly(ethylene glycol)-ylated (PEGylated) conjugates and conjugates with other pharmaceutically-acceptable polymers. Peptide-conjugated or protein-conjugated FGF21 and mutant FGF21 protein sequences include both chimeric proteins that contain a second protein, such as an scFv fragment, or other peptide sequences attached in-frame to the N-terminal or C-terminal end of the FGF21 and mutant FGF21 protein sequences, and which are translated together as a chimeric gene as are broadly-known in the art using any of the many art-recognized gene cloning and expression methods.

Peptide-conjugated or protein-conjugated FGF21 protein and mutant FGF21 protein sequences also includes FGF21 and mutant FGF21 proteins linked by any useful linking technology to another protein, such as maleimide or succinimide linking of antibodies, e.g. humanized antibodies, antibody scaffolds, or antibody fragments. A large number of FGF21 and mutant FGF21 proteins, as well as examples of FGF21 proteins and mutant FGF21 proteins conjugated to other proteins or peptides are described in the references cited below. By "conjugated" in reference to proteins, it is meant that two proteins are covalently linked together. For instance, proteins can be linked via sulfhydryl (thiol), amine, carboxyl, aldehyde, hydroxy or azide groups either native to a protein, inserted into a protein as an amino acid insertion or substitution, or produced in a protein by a chemical reaction. In one example, one or both conjugated proteins are linked to the other by their N-terminus or C-terminus. A large variety of protein conjugation methods are known and useful linkers are broadly-available (see, e.g., Thermo Scientific Crosslinking Technical Handbook (2012) Thermo Scientific).

"Antibodies" include polyclonal antibodies, monoclonal antibodies, and derivatives or analogs of antibodies, including without limitation: Fv fragments; single chain Fv (scFv) fragments; Fab' fragments; F(ab')2 fragments; humanized antibodies and antibody fragments; camelized antibodies and antibody fragments; multivalent versions of the foregoing, such as bispecific antibodies, including disulfide stabilized Fv fragments, scFv tandems ((scFv)fragments), diabodies, tribodies, tetrabodies, which typically are covalently linked or otherwise stabilized (i.e., leucine zipper or helix stabilized) scFv fragments, and CovX-bodies (Doppalapudi et al. Chemical Generation of Bispecific Antibodies, *Proc. Natl. Acad. Sci. USA*. 2010 Dec. 28; 107(52):22611-6). In one aspect, the antibody is a CovX-body scaffold, e.g., CVX-2000 (Doppalapudi et al. *Proc. Natl. Acad. Sci. USA*. 2010 Dec. 28; 107(52):22611-6). For use in humans, the antibody is preferably humanized or otherwise non-antigenic, and in one aspect lacks an antigen-binding site or it lacks an antigen binding site that binds a native human epitope. In its use conjugated to an FGF21 protein for the sole purpose of lengthening in vivo bioavailability, the affinity of the antibody, that is, the antigen to which the antibody binds, is not material, and, as with the CovX-body scaffold, CVX-2000 (humanized IgG1κ), lacks an antigen-binding site (e.g., paratope).

Molecular cloning techniques for production of FGF21 and mutant FGF21 protein, chimeric proteins, and other proteins, as well as methods of selecting and producing suitable antibodies (including antibody fragments, antibody scaffolds, or chimeric antibodies, such as humanized antibodies), or other proteins to conjugate with the FGF21 protein or mutant FGF21 protein are broadly-known, e.g. in Huang, J. et al. (Development of a Novel Long-Acting Antidiabetic FGF21 Mimetic by Targeted Conjugation to a Scaffold Antibody, *JPET* August 2013 vol. 346(2):270-280), and/or in the patent documents cited herein, and need not be described herein in further detail.

One example of a potent form of FGF21 is identified as LY2405319, an investigational variant (that is a functional FGF21 mutant protein) suitable for early-phase clinical development. Another example of a long-acting FGF21 mutant protein is PF-05231023 disclosed in Huang, J. et al. (*JPET* August 2013 vol. 346(2):270-280). A person of ordinary skill can produce or otherwise obtain, and test the functionality or efficacy of any FGF21 protein in its neuro-protective capacity without undue experimentation, according to the teachings herein and the general knowledge of that person.

Exemplary FGF21 proteins include, without limitation, Human FGF21 protein (mature) according to U.S. Pat. No. 7,582,607 (FIG. 2A); mature human FGF21 sequence according to Yie, J. et al. (N- and C-termini play different roles in receptor interaction and activation", *FEBS Letters*, 2009 583(1):19-24, FIG. 2B); and human FGF21 precursor from GenBank Accession No. NP_061986.1 (including the signal peptide, FIG. 2C).

Modifications of native FGF21 sequences to product FGF21 mutant proteins are described in the art. One example of an FGF21 mutant protein is LY2405319 according to (Kharitonenkov A, et al., (2013) Rational Design of a Fibroblast Growth Factor 21-Based Clinical Candidate, LY2405319. *PLoS ONE* 8(3):e58575. doi:10.1371/journal.pone.0058575): Modification #1=Leu118Cys; Modification #2=Ala134Cys; Modification #3=Ser167Ala; and Modification #4=deletion of first four n-terminal residues, HPIP, yielding the sequence shown in FIG. 2D (Amino Acid alterations as compared to SEQ ID NO: 4 are highlighted in bold and underlined).

Another example of a FGF21 mutant protein is a Δ(His1Pro2Ile3Pro4)-Leu118Cys-Ala134Cys-Ser167Ala FGF21 mutant protein consisting of native human FGF21 (e.g., SEQ ID NOS: 3 or 4) containing an engineered disulfide bond and a substitution of Ser167 with Ala.

Huang, J. et al. (*JPET* August 2013 vol. 346(2):270-280) describe FGF21 mutant proteins having residues that permit conjugation to an antibody, including (e.g., with respect to SEQ ID NO: 3 or 4), mutation of three or four native Lys residues to Arg, leaving a single Lys residue available for linkage with a succinimide linker, mutating all native Lys residues to Arg, combined with H1K or S181K for C-terminal or N-terminal linkage via a succinimide chemistry, or addition of a free Cys reside for conjugation with a maleimide linker (for example and without limitation 3-(2,5-dioxo-2,5-dihydro-1H-pyrrol-1-yl)-N-[2-(2-(3-oxo-3-((4-(3-oxo-3-(2-oxoazetidin-yl)propyl)phenyl)amino)propoxy)ethoxy)ethyl]propanamide), including D79C, H125C, or A129C, optionally with a ΔH1 mutation, such as a ΔH1-A129C FGF21 mutant protein. The FGF21 mutant proteins were conjugated to a scaffold antibody CVX-2000 (See, also, Doppalapudi et al. *Proc. Natl. Acad. Sci. USA*. 2010 Dec. 28; 107(52):22611-6, U.S. Patent Publication No. 20120282279 A1, and U.S. Pat. No. 8,722,622, incorporated herein by reference for their technical disclosure of FGF21 and FGF21 mutant proteins conjugated to an antibody or an antigen-binding portion thereof).

As indicated in U.S. Pat. No. 7,582,607, additional modifications in reference to FGF21 (SEQ ID NOS: 3 or 4), as indicated above, to produce functional FGF21 mutant proteins (muteins), include:

a. substitution of any amino acid except Ser or Thr for Ser 167, wherein said mutein has reduced capacity for 0-glycosylation when expressed in yeast compared to wild-type human FGF-21;

b. substitution of any amino acid except Ser or Thr for Ser 167, in combination with the substitution of a cysteine for two or more of the following in any combination disclosed: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO: 1 and wherein said mutein has reduced capacity for O-glycosylation when expressed in yeast compared to wild-type human FGF-21; and c. substitution of any amino acid except Ser or Thr for Ser 167, in combination with the substitution of a charged (Lys, Arg, His, Asp, Glu) and/or polar but uncharged (e.g., Ser, Thr, Asn, or Gln) amino acid for one or more of the amino acids at positions: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152; alanine 154; glutamine 156, glycine 161, serine 163, glycine 170, or serine 172, wherein said mutein has reduced capacity for O-glycosylation when expressed in yeast compared to wild-type human FGF-21.

All permutations of (a), (b), and (c) are provided herein.

The FGF21 is compounded or otherwise manufactured into a suitable composition for use, such as a pharmaceutical dosage form or drug product in which the compound or compounds are an active ingredient. Compositions may comprise a pharmaceutically acceptable excipient (e.g. carrier). An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts. For example for an intravenous drug product, the FGF21 is provided in a water, saline (e.g. normal saline), lactated Ringers, or phosphate-buffered saline (PBS) solution.

In one aspect, the FGF21 is provided in a composition that is used to induce and/or maintain hypothermia, and includes active or inactive compositions. Non-limiting examples of compositions used to induce or maintain hypothermia include normal saline or lactated Ringer's.

An "effective amount" of FGF21 is an amount that causes increased expression of RBM3 in a nerve cell at hypothermic temperatures, e.g. at a temperature ranging from 5° C. to 36.5° C., from above 33° C. and below 37° C., from 34° C. to 36.5° C., from 35.5° C. to 36.5° C., or 36° C., and/or is an amount effective to improve brain function in a patient as indicated above. An amount of FGF21 effective to increase RNA binding motif 3 (RBM3) production in nerve cells of the patient ranges from 1 pg/kg to 500 mg/kg, or a loading and/or maintenance dose (mg/kg) sufficient to target FGF21 CSF or plasma level in the range of 5-300 nanomolar. Effective amounts of any FGF21 protein can be determined empirically, using, e.g., methods described herein. For example, mutated FGF21 proteins (e.g. such as LY2405319) may have lower or higher affinity or activity (e.g. specific activity) to activate the FGF21/β-klotho receptor, and therefore the effective amount of the mutated FGF21 protein would likely be different than that of native FGF21.

In any aspect of the methods provided herein, hypothermia, and treatment with the FGF21 protein overlap (that is, the FGF21 protein is administered to and is maintained in the hypothermic patient in an effective amount to increase RNA binding motif 3 (RBM3) production in nerve cells of the patient), and the overlap is at least one half hour, for example, 0.5, 1, 2, 3, 4, 6, 10, 12, 18, 24, 30, 36, 48, 60, or 72 hours, one or more days, or one or more weeks.

EXAMPLES

Extremely mild hypothermia to 36.0° C. is not thought to appreciably differ clinically from 37.0° C. Here we show that cold stress protein RNA Binding motif 3 (RBM3) increases in neuron cultures maintained at 33° C. or 36° C. for 24 or 48h, compared to 37° C. controls. Neurons cultured at 36° C. also had increased global protein synthesis (GPS). Our novel findings show that a 1° C. reduction in temperature can induce pleiotropic biochemical changes by upregulating GPS in neurons which may be mediated by RBM3.

The Examples below support the following points. First, neuroprotection can be augmented in mild-moderate cooling independent of patient age. RBM3 is a highly protective protein in vitro & in vivo. It helps organisms and cells adapt to cold stress. The only therapy previously known to increase RBM3 in vivo is <deep hypothermia (DH). Temperatures<DH are dangerous and ineffective in treating acute brain injury (Wienrauch, V, et al. Beneficial Effect of Mild Hypothermia and Detrimental Effect of Deep Hypothermia After Cardiac Arrest in Dogs 1992 *Stroke* 23:1454-1462) likely due to mechanisms independent of RBM3 (e.g. coagulopathy). DH may also increase the risk of stroke in the setting of deep hypothermia circulatory arrest (DHCA) for elective or corrective surgery (Tian, D H, et al. A Meta-Analysis of Deep Hypothermic Circulatory Arrest Alone Versus with Adjunctive Selective Antegrade Cerebral Perfusion (May 2013) *Ann Cardiothorac Surg.* 2(3):261-270). Mild-moderate hypothermia is reasonably safe and clinically beneficial in the treatment of acute brain injury. Clinically applied mild-moderate hypothermia previously has not been shown to induce protective RBM3 protein in vivo. As such, there is an unmet need for methods to increase RBM3 levels for greater cellular protection during mild-moderate hypothermia. As shown in the Examples below, FGF21 augments RBM3 in neurons cooled to 36° C. (ultra-mild hypothermia). Further, Mild-hypothermia to 33° C. increases β-klotho in neurons (i.e. cooling upregulates the rate-limiting protein β-klotho, which is a protein necessary to biochemically communicate FGF21's biological effects). Based on the Examples, it is theorized that mild, moderate, deep, or profound hypothermia increases β-klotho which allows FGF21 ligand to bind its receptors and increase neuroprotective RBM3.

Second, riskier TH can be substituted with safer UMH in neonates. Mild-moderate hypothermia is an effective CNS protective therapy in neonates. Mild-moderate hypothermia (e.g. <33° C.) is generally well-tolerated and relatively safe but can increase complications, which may adversely impact patient outcomes. This includes altered metabolism of neuroactive drugs commonly used in neurocritical care such as the benzodiazepine midazolam (Fukuoka, N, et al. Biphasic Concentration Change During Continuous Midazolam Administration in Brain-Injured Patients Undergoing Therapeutic Moderate Hypothermia (February 2004) *Resuscitation.* 60(2):225-30). There is an unmet need for methods to make ultra-mild hypothermia (UMH—35.5° C. to 36.5° C.) a neuroprotective proxy for standard of care mild-moderate TH in neonates; UHM has the advantage that near-normal temperatures have a reduced risk of interfering with other complex/changing components involved in neurocritical care to optimize patient management. As shown in the Examples below, FGF21 augments RBM3 in neurons cooled to 36° C. (ultra-mild hypothermia); Baseline levels of brain β-klotho are high in normothermic (37° C.) neonates vs. adults; in vivo brain injury increases baseline RBM3 levels in neonates but not in adults; and human pediatric patients have elevated RBM3 in CSF. Based on the Examples, it is believed that because β-klotho/RBM3 signaling is high in neonates at normal baseline temperature (37° C.), and RBM3 signaling is more sensitive to changes such as by injury, neonates (e.g. newborn, e.g. infants) will robustly respond to FGF21 therapy (that is, FGF21 will potently augment RBM3 at ultra-mild temperatures in this age group, and induce a degree of neuroprotection similar to mild-TH alone.

Third, the side-effects of hypothermia can be mitigated by the methods described herein. RBM3 is believed to mediate adaptive cellular responses which help mammalian cells tolerate cold stress. Hypothermia for treatment of brain injury unavoidably leads to cooling of non-CNS organs. There is an unmet need for methods that increase the safety of mild, moderate, deep, and profound hypothermia, when used for treatment of brain injury but independent of direct neuroprotection. FGF21 therapy is a novel method to improve outcomes in hypothermia-treatment patients: FGF21 augments RBM3 in neurons cooled to 36° C. (ultra-mild hypothermia); and Mild-H to 33° C. increases β-klotho in neurons (i.e. cooling upregulates the rate-limiting protein β-klotho, which is a protein necessary to biochemically communicate FGF21's biological effects). Based on the Examples, it is believed that neurons are an example of a cell type in which FGF21+hypothermia induces RBM3. This mechanism may broadly exist across the body in other cell types. Increased RBM3 across the body may generally help brain injured patients tolerate hypothermia and also reduce its side effects when used for neuroprotection.

Example 1: Cold Stress Protein RBM3 Responds to Temperature Change in an Ultra-Sensitive Manner in Young Neurons Extremely mild hypothermia to 36.0° C. is not thought to appreciably differ clinically from 37.0° C. Here, RBM3 and/or CIRBP were tested to determine if they are increased in primary cortical neuron and/or astrocyte cultures cooled to 36° C. versus conventional hypothermia to 33° C., as compared with normothermia to 37° C. Surprisingly, 36° C. upregulated RBM3 in young 6 d primary neuron cultures, but failed to do so in mature 26 d old neurons. Also, 36° C. for 48 h mildly increased RBM3 in astrocytes. RBM3 upregulation in young neurons cooled to 36° C. was also associated with elevated GPS. Finally, we found that fibroblast growth factor 21 (FGF21), melatonin, and liver X receptor (LXR) agonist T0901317 augmented RBM3 upregulation in young neurons cooled to 36° C. Our results show that a 1° C. reduction in temperature can induce pleiotropic biochemical changes by upregulating GPS in neurons which is thought to be mediated by RBM3, and that this process can be pharmacologically mimicked and enhanced with melatonin or FGF21.

Experimental Procedures

Reagents. Puromycin dihydrochloride was purchased from SIGMA (Cat #P9620-10 mL; St. Louis, Mo., USA). FGF21 was purchased from R&D Systems (Minneapolis, Minn., USA). Melatonin, T0901317, and SRT1720 were purchased from Tocris (Bristol, UK). AZD1080 was purchased from Cayman Chemical (Ann Arbor, Mich., USA). Primary antibodies: Anti-RBM3 was purchased from Proteintech Group and used at 1:1000 (Cat #14363-1-AP; Chicago, Ill., USA). Anti-CIRBP, anti-α-Tubulin, anti-pAKT(Ser473), anti-AKT total, anti-pERK, anti-ERK total, anti-eIF2α(Ser51), anti-eIF2α total were purchased from Cell Signaling Technology(Danvers, Mass., USA). Anti-puromycin (12D10) was purchased from EMD Millipore and used at 1:15,000 (Cat #MABE343; Billerica, Mass., USA). Goat anti-rabbit secondary antibodies were purchased from Life Technologies (Grand Island, N.Y., USA).

Animals. Animal studies were approved by the Institutional Animal Care and Use Committee of the University of Pittsburgh. Euthanasia protocols follow recommendations established by the American Medical Veterinary Association Guideline for Euthanasia. Female timed pregnant Sprague Dawley rats were purchased from Charles River (Wilmington, Mass., USA) and granted ab libitum accesses to food and water, and maintained on a 12 h light/dark cycle prior to euthanasia to harvest embryos.

Primary Cortical Neuron Culture. Embryos (mixed gender) were isolated from timed pregnant (E16-17) Sprague Dawley rats. Neuron cultures were performed as previously described (Jackson TC, et al. (2013) Pharmacological inhibition of pleckstrin homology domain leucine-rich repeat protein phosphatase is neuroprotective: differential effects on astrocytes. *J Pharmacol Exp Ther* 347:516-528). Cortices were dissected in ice-cold Hanks balanced salt solution (HBSS; Life Technologies, Grand Island, N.Y., USA) containing sodium bicarbonate (SIGMA), penicillin-streptomycin (Life Technologies), and 4-(2-hydroxyethyl)-1-piperazineethanesulfonic acid (HEPES; Life Technologies). Brain tissues were dissected under a Leica M651 light microscope (Buffalo Grove, Ill., USA), and placed in a 1.5 mL tube containing ~1 mL prepared HBSS. Tissues were minced and transferred to a 15 mL conical tube. Cells were spun 5 min/200 g/4° C. Supernatant was aspirated, cells resuspended in 2 mL trypsin solution, and incubated 8 min at 37° C. with gentle mixing. Trypsin activity was quenched in 10 mL Neurobasal/B27 (Life Technologies) containing 10% fetal bovine serum (FBS; Thermo Fisher Scientific, Pittsburgh, Pa., USA). Cells were transferred into a new 15 mL conical tube and spun 5 min/200 g/4° C. Supernatant was replaced with 1.5 mL trituration media. Cells were dissociated by 10 passages through a fire-polished glass Pasteur pipette. The cell pellet was resuspended in plating media warmed to 37° C. (Neurobasal Media/B27 supplement prepared+25 μM L-Glutamic Acid+Pen-Strep). Cell number was quantified by automatic counting on a Cellometer (Nexcelom Bioscience, Lawrence, Mass., USA). Cells were seeded onto 6-well culture plates coated with poly-D-lysine (density ~1.2-1.5×10$^6$/well). Cultures were maintained by half media replacement every ~3-4 days in vitro (DIV). The mitotic inhibitor cytosine β-D-arabinofuranoside hydrochloride (ARA-C; 4 μM final concentration) was added in study 1 experiment (e.g. DIV10-11 cultures) to ensure purity of neuronal biochemistry for initial assessment of temperature treatments. Mitotic inhibitors at low levels are non-toxic but still potentially represent a mild stressor (though necessary to guarantee neuron purity) (Ahlemeyer B, et al., (2003) Cytosine arabinofuranoside-induced activation of astrocytes increases the susceptibility of neurons to glutamate due to the release of soluble factors. *Neurochem Int* 42:567-581). Results of temperature treatments were confirmed in younger DIV6 neurons in the absence of ARA-C (neuron enriched cultures; >90% neurons). Astrocytes were allowed to proliferate in aged cultures, which were not treated with ARA-C. It was observed that astrocytes are necessary for long-term survival of neuron cultures (i.e. DIV26 mature neuron cultures).

Primary Astrocyte Culture: Pure rat astrocyte cultures were prepared as previously reported (Jackson TC, et al. (2013) *J Pharmacol Exp Ther* 347:516-528). In brief, brains were collected from postnatal day 2 SD rat pups. Mixed brain cells were seeded onto T75 culture flasks and maintained in DMEM/F12/10% FBS/Pen-Strep culture media. Astrocytes were repeatedly split and propagated in new T75 flasks until pure. At propagation #5, astrocytes were seeded onto poly-D-lysine coated 6-well plates ($7.5 \times 10^4$/well) and maintained for an additional ~3 d. At ~60-70% confluency in 6-well plates, astrocytes were given fresh media exchange then temperature treatments were initiated for 24 h and 48 h.

Hypothermia Protocols: Neurons were maintained in a 37° C. (normothermic) incubator. Before start of hypothermia, two identical incubators of the same make/model with humidity of ~95% (all in the same room) were programmed to 36° C. and 33° C. Incubators were allowed a minimum of 48 h equilibration time prior to starting hypothermic experiments. In some experiments, as an additional control, a thermometer was placed inside hypothermic incubators as a secondary gauge of temperature. Temperature as assessed by that approach was independently confirmed to never be under target temperature and fluctuate by no more than ~0.5° C. On DIV of interest, culture plates were assigned to one of the three experimental temperatures for 24 or 48 h.

Drug Treatments: Drugs were prepared in DMSO or PBS (i.e. for FGF21). All drugs were diluted in conditioned culture media and applied for 24 h. Controls received equal amounts of DMSO/PBS without drugs. Primary neurons were harvested for biochemistry at key time points. RBM3 and CIRBP levels were measured by Western blot. Investigators were not blinded to temperature treatment groups.

Analysis of de novo protein synthesis. Surface sensing of translation (SUnSET) is a recently developed non-radioactive method using puromycin incorporation to accurately measure rate of new protein synthesis in cells (Schmidt EK, et al., (2009) SUnSET, a nonradioactive method to monitor protein synthesis. *Nat Methods* 6:275-277). That protocol was adapted with slight modification. Briefly, at the end of temperature treatments (on DIV6), conditioned media was collected by removing 1 mL from each well of 6 well plate, for all plates, and set aside. Conditioned media was pooled but separated by temperature group to control for potential secreted proteins during 48 h treatment. Pooled conditioned media (separated by temperature group) and fresh neurobasal/B27 media (stored at 4° C.) were pre-warmed to 37° C. Remaining culture media from 6 well plates were then aspirated off and replaced with either 1 mL of conditioned media (specific for each temperature) or 1 mL fresh media; fresh neurobasal/B27 media was applied in some neurons to stimulate global protein synthesis. Neurons were incubated for 1 h, media aspirated off, and replaced with ~1.5 mL 37° C. warmed PBS containing 10 ng/mL puromycin. Neurons were incubated for ~30 mins, washed once with ice cold PBS (without puromycin), and harvested for biochemistry. Investigators were not blinded to temperature treatment groups.

Western Blot. Cells were quickly washed with ice cold PBS and harvested in RIPA buffer containing EDTA, protease inhibitors, and phosphatase inhibitors (Thermo Scientific-PIERCE). Samples were sonicated ~20 s in 0.6 mL conical tubes. Homogenized material was spun 10 min/16,000 g/4° C., and supernatant was used for downstream SDS-PAGE (whole cell extracts). Protein concentration was determined using the BCA assay (Thermo Scientific-PIERCE). 15-30 µg of protein was mixed with Laemmli loading buffer (BioRad, Hercules, Calif., USA). Samples were heated 95° C./5 min, and loaded on pre-cast TGX 4-15% gradient gels (BioRad). Gels were run at 150V and proteins were transferred onto polyvinylidene fluoride (PVDF) membrane (GE Healthcare Bio-Sciences, Pittsburgh, Pa., USA). Transfers were run at 100V for ~1 h 15 min. During course of investigations GE Healthcare discontinued our preferred PVDF membrane Hybond-P (Cat #RPN2020F). While testing alternative PVDFs, prior to consuming current stock, we inadvertently discovered that RBM3 is difficult to detect using some brands of membrane (FIG. 1). This suggests PVDF selection may be an important variable to study RBM3. All RBM3/CIRBP Western blots in this report used (now discontinued) Hybond-P membrane, which displays optimal RBM3 binding/detection characteristics. However, results suggest new Hybond P 0.2 membrane is also a good alternative to detect RBM3 with lower non-specific background. Precision Plus Kaleidoscope protein standards (BioRad) were used for MW estimation. Membranes were washed using 1X Tris-Buffered-Saline (TBS; BioRad) and blocked in TBS-Tween-20 (TBST) containing 7.5% blotting grade milk (TBS-T/milk) for 1 h. Primary antibodies were prepared in TBS-T/7.5% milk and incubated overnight in a 4° C. cooler. Blots were washed with TBS and incubated with secondary antibodies for 2 h. Blots were given final TBS washes, incubated with ECL-2 HRP-detection reagent (Thermo Fisher-PIERCE), and imaged in a dark room. Films were scanned and compiled in Photoshop. Densitometry analyzed by UN-SCAN-IT software (Silk Scientific, Orem, Utah).

Figure 4A:
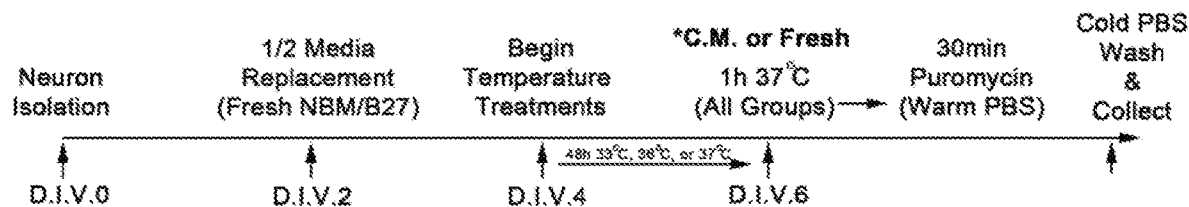
FIGS. 4A-4J: Mild Hypothermia Increases RBM3 in DIV6 Neurons and Increases Protein Synthesis.
Figure 4B:
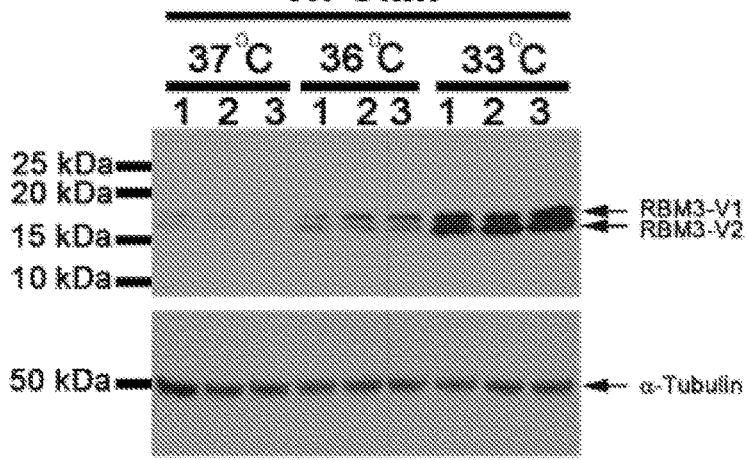
Figure 4C:
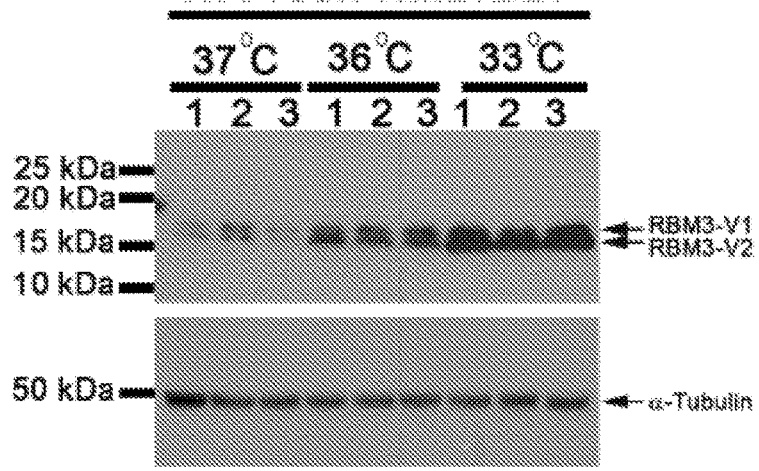
Figure 4D:
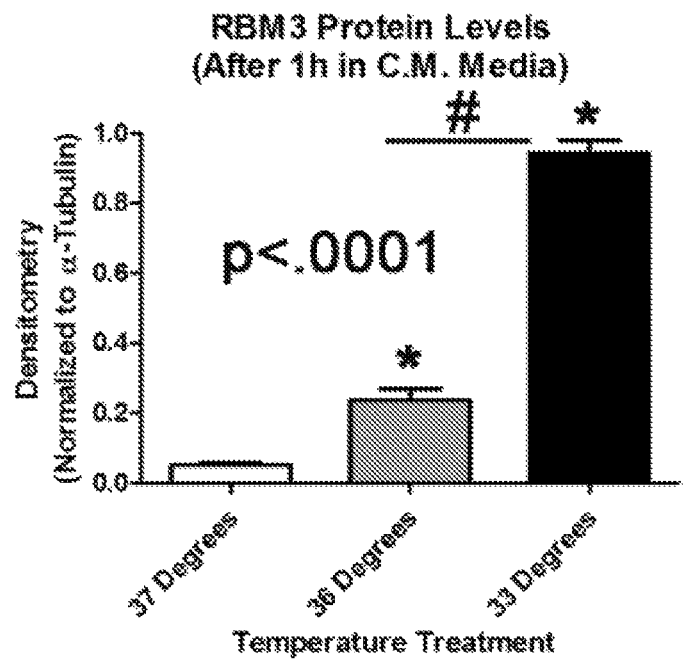

Statistical Analysis. Data were analyzed and graphed using GraphPad PRISM software (GraphPad Software Inc., La Jolla, Calif., USA). Multiple comparisons were analyzed by ANOVA and Newman-Keuls Multiple Comparison post-hoc analysis. Data were considered significant at $p<.05$ using two-tailed tests. All graphs show mean+SEM. Intra-blot group comparisons of densitometry, collected as relative pixel intensity, were standardized for graphing by expressing group differences as values between 0 and 1 on the y axis. In FIG. 4D, α-tubulin normalized densitometry values were transformed to give log(Y) values and used for statistical analysis to correct for non-normality in distribution.

Results

Figure 3F:
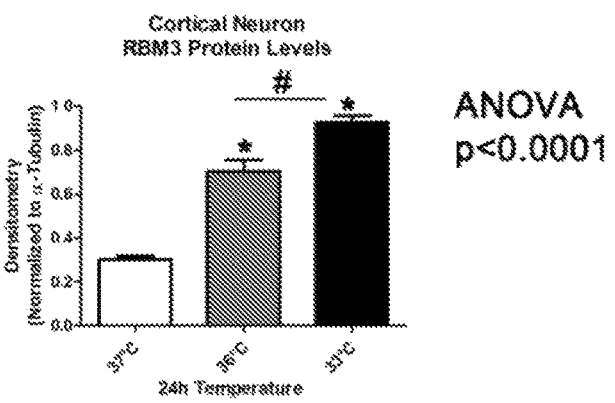
Figure 3G:
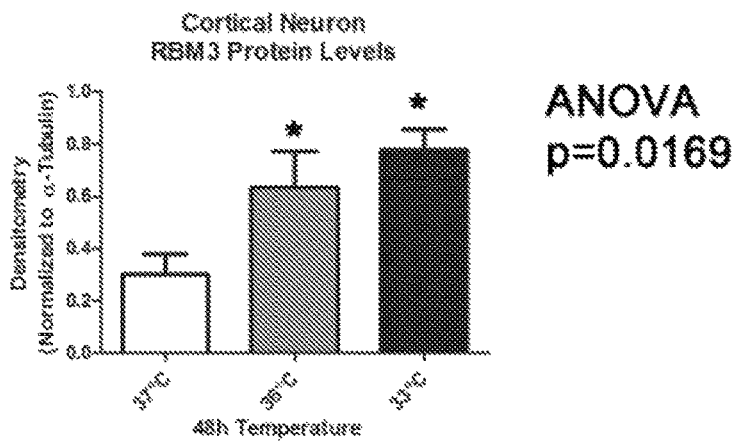

Experimental hypothermic temperatures were tested in pure neuron cultures as outlined (FIG. 3A). The predicted molecular weight of RBM3 and CIRBP is ~17 kDa and ~18 kDa, respectively. Antibodies detected RBM3 and CIRBP proteins in DIV11 neurons cooled to 33° C. for 48 h. Western blots show a dominant ~17 kDa RBM3 band, and a fainter ~18 kDa CIRBP band (FIGS. 3B and 3C). 24 h exposures were compared to either 36° C. or conventional mild hypothermia (33° C.) to induce RBM3/CIRBP in neurons (FIG. 3D). Neuronal RBM3 protein levels were ~2-fold higher after 24 h 36° C., compared to 37° C. normothermic controls (FIG. 3F; n=5/group; ANOVA, $p<0.0001$). RBM3 levels were highest in the 33° C. group at 24 h (n=5)—although statistically significant this represented only a minor increase above 36° C. RBM3 levels at 24 h (FIG. 3F). By 48 h RBM3 levels in 36° C. and 33° C. groups were ~2-fold higher than 37° C. normothermic controls (FIGS. 3E and 3G; n=5/group; ANOVA, p=0.0169). RBM3 levels were not significantly different comparing 36° C. versus conventional 33° C. groups at 48 h (FIG. 3G). CIRBP was barely detectable in primary rat neurons and did not increase with cooling which is consistent with prior studies by others (FIG. 3D and FIG. 3E).

Figure 4E:
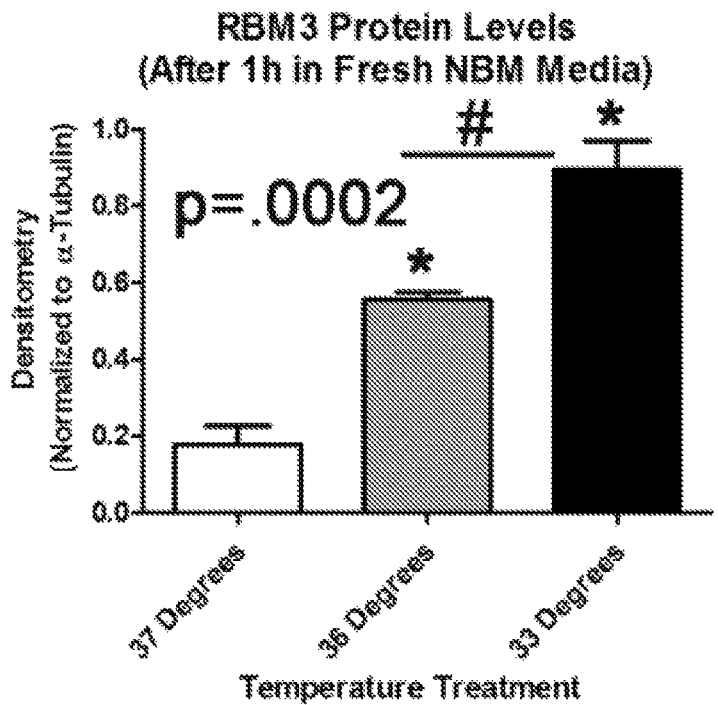
Figure 4F:
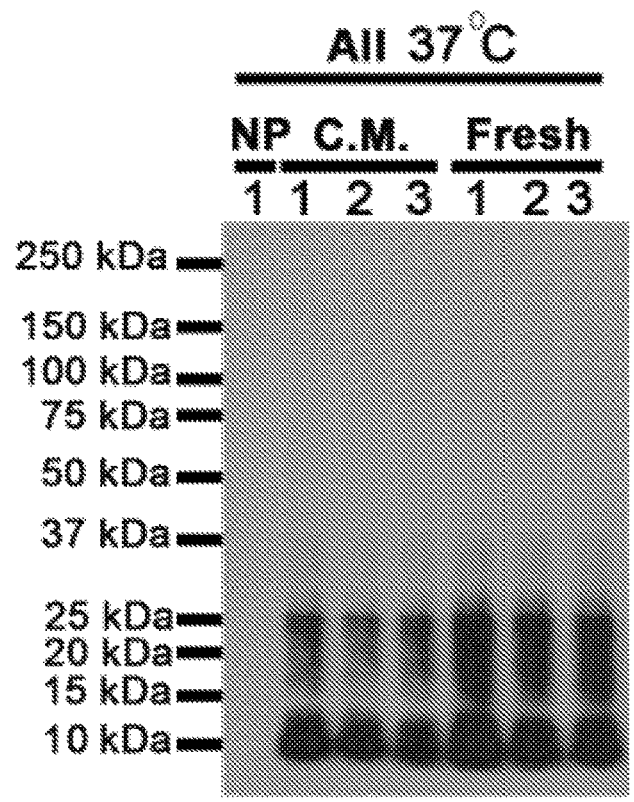
Figure 4G:
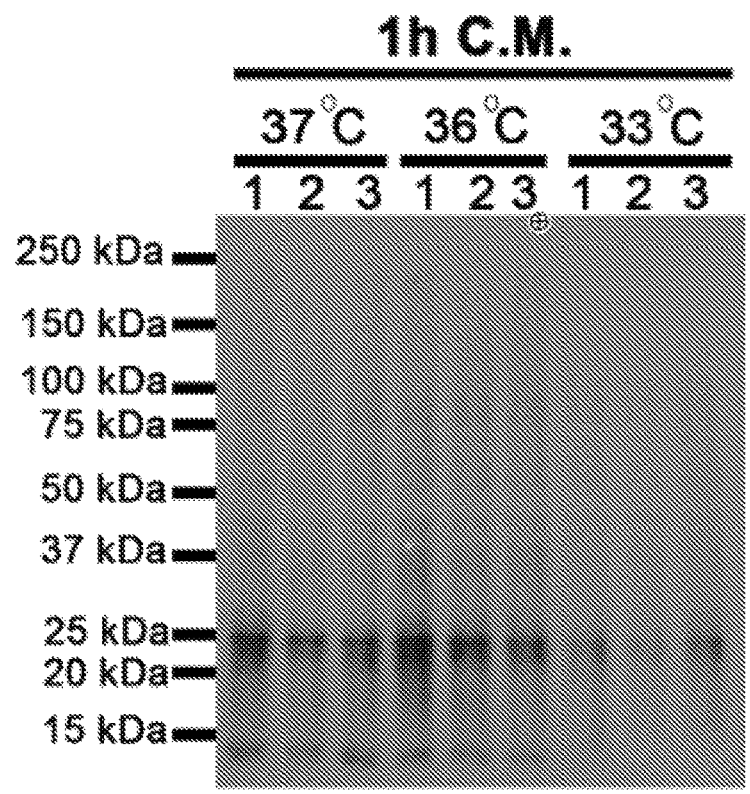
Figure 4H:
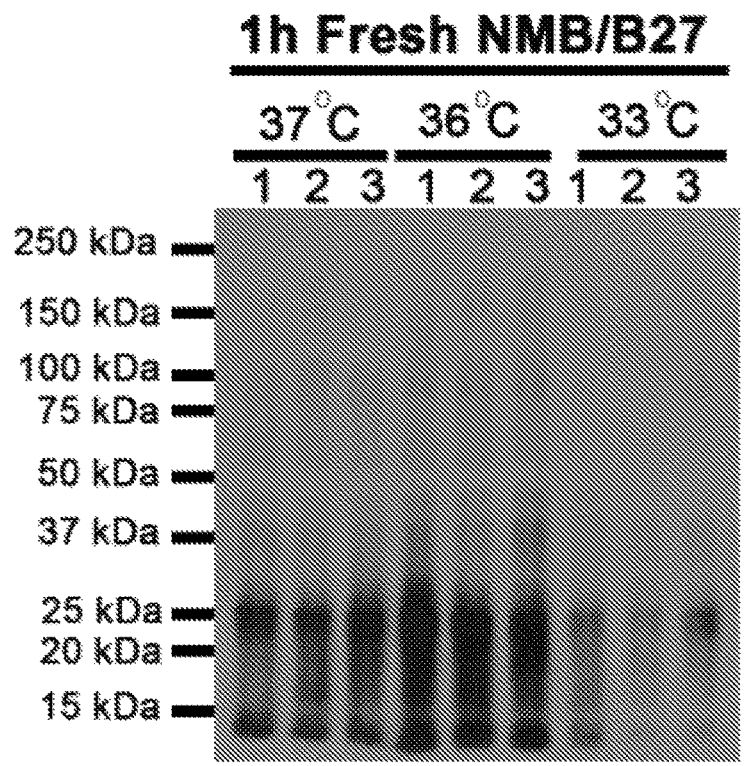
Figure 4I:
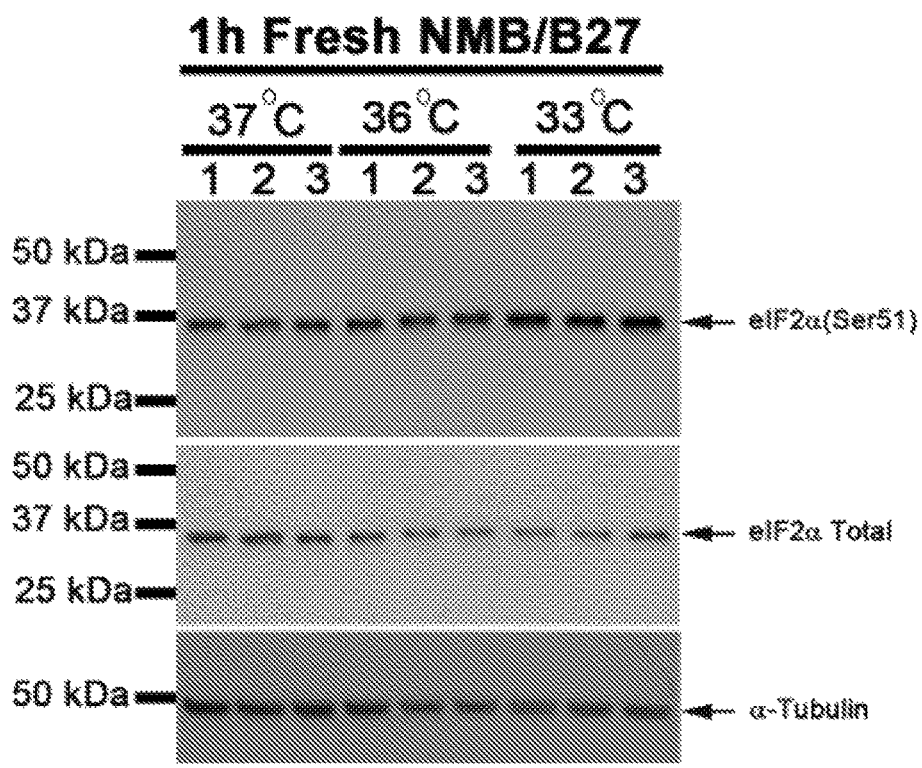
Figure 4J:
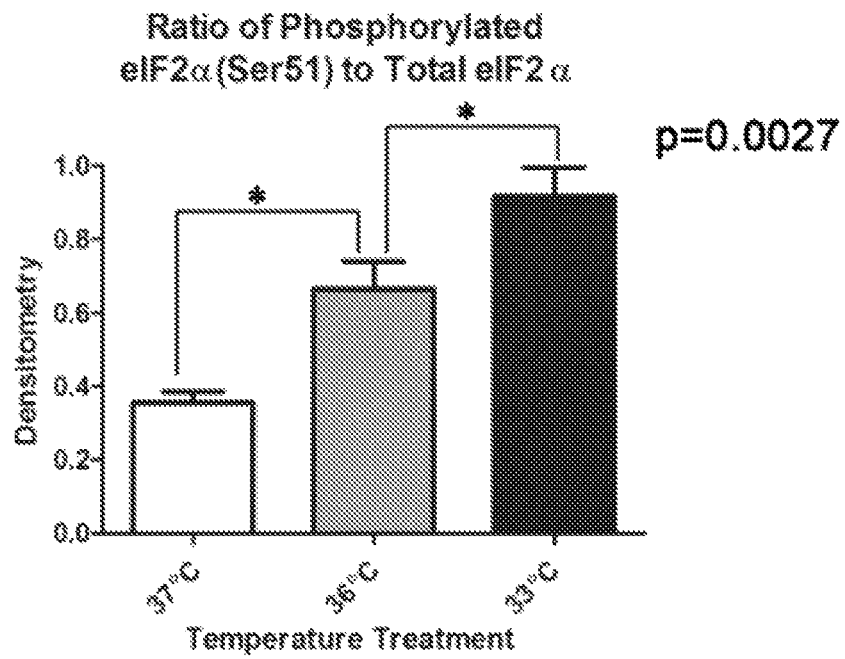

Next, it was determined if temperature treatments alter global protein translation in young DIV6 neurons. Experiments were performed as outlined (FIG. 4A). RBM3 levels increased with 48 h cooling in both 36° C. and 33° C. groups (FIG. 4B-E). In the 36° C. group, RBM3 levels were augmented more if re-warmed for 1 h in fresh neurobasal/B27 media compared to neurons re-warmed in conditioned media (FIGS. 4D and 4E). In young DIV6 neurons, RBM3 levels were highest in the 33° C. group—regardless of 1 h treatment with fresh or conditioned media. Fresh media exchange on cells is assumed to stimulate protein translation by providing renewed nutrients and growth factors but other factors such as altered pH may also be involved. To validate that assumption, de novo GPS was measured by SUnSET in 37° C. treated control neurons given conditioned or 1 h fresh media. As expected, neurons given fresh media had higher levels of puromycin incorporation (i.e. higher GPS). Also, anti-puromycin antibody failed to detect signal in DIV6 neurons that were not treated with puromycin (FIG. 4F). Next we compared if conditioned media vs. fresh media affected or unmasked, respectively, the ability of hypothermia treatments to alter protein translation. 36° C. increased protein synthesis in neurons given fresh media but not to the same extent in those given conditioned media (FIGS. 4G and 4H). GPS was reduced in neurons given 33° C. for 48 h. Consistent with that observation, eIF2α (a master regulator of global cap-dependent protein translation) was inhibited most in 33° C. cooled neurons compared to 36° C. or 37° C. groups (i.e. increased Ser51 phosphorylation; FIGS. 4I and 4J).

Figure 5A:
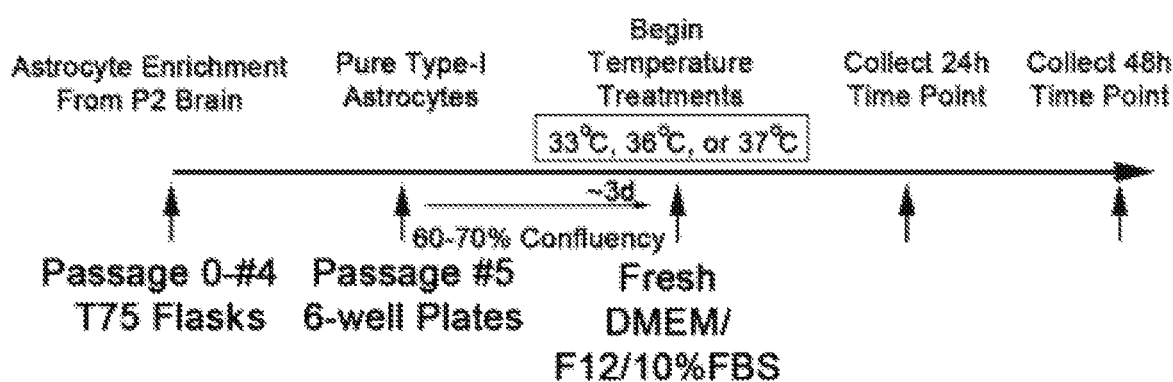
Figure 5B:
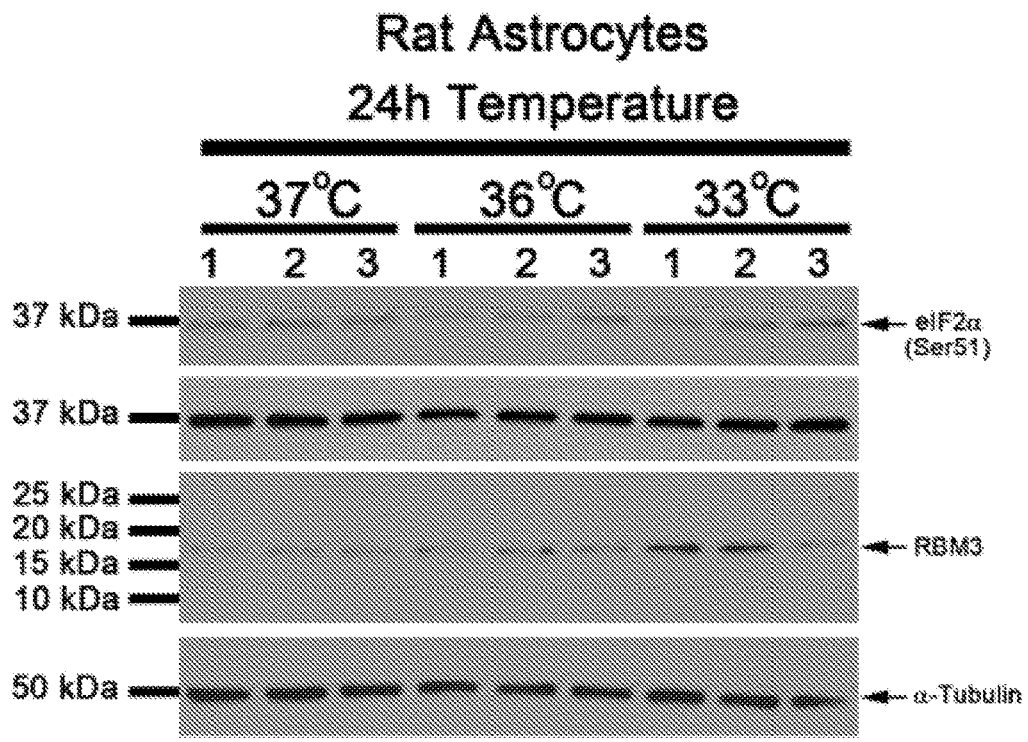
Figure 5C:
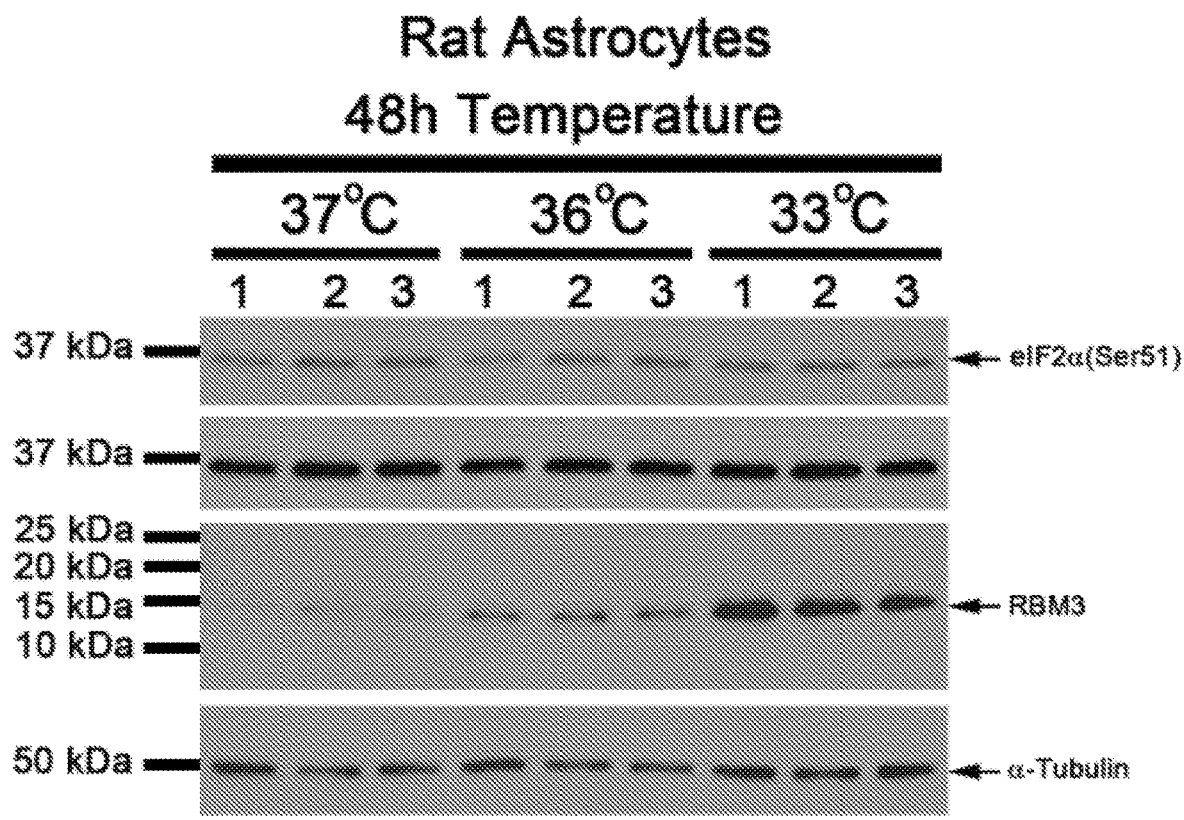

It was then determined if 36° C. and/or 33° C. induces RBM3 in rat brain astrocytes. Astrocytes were propagated to purity. Approximately 3 d after seeding onto 6-well plates, astrocytes were given fresh media exchange and temperature treatments immediately initiated (FIG. 5A). 24 h exposure to hypothermia temperatures did not appear to alter RBM3 levels compared to 37° C. controls (FIG. 5B). RBM3 was significantly increased after 48 h exposure to 36° C. (FIGS. 5C and 5D). However, 33° C. induced much higher levels of RBM3 compared to 36° C. (FIGS. 5C and 5D). Phosphorylation of eIF2α in astrocytes was unaffected by temperature treatments at either time point (FIGS. 5B and 5C).

Figure 6B:
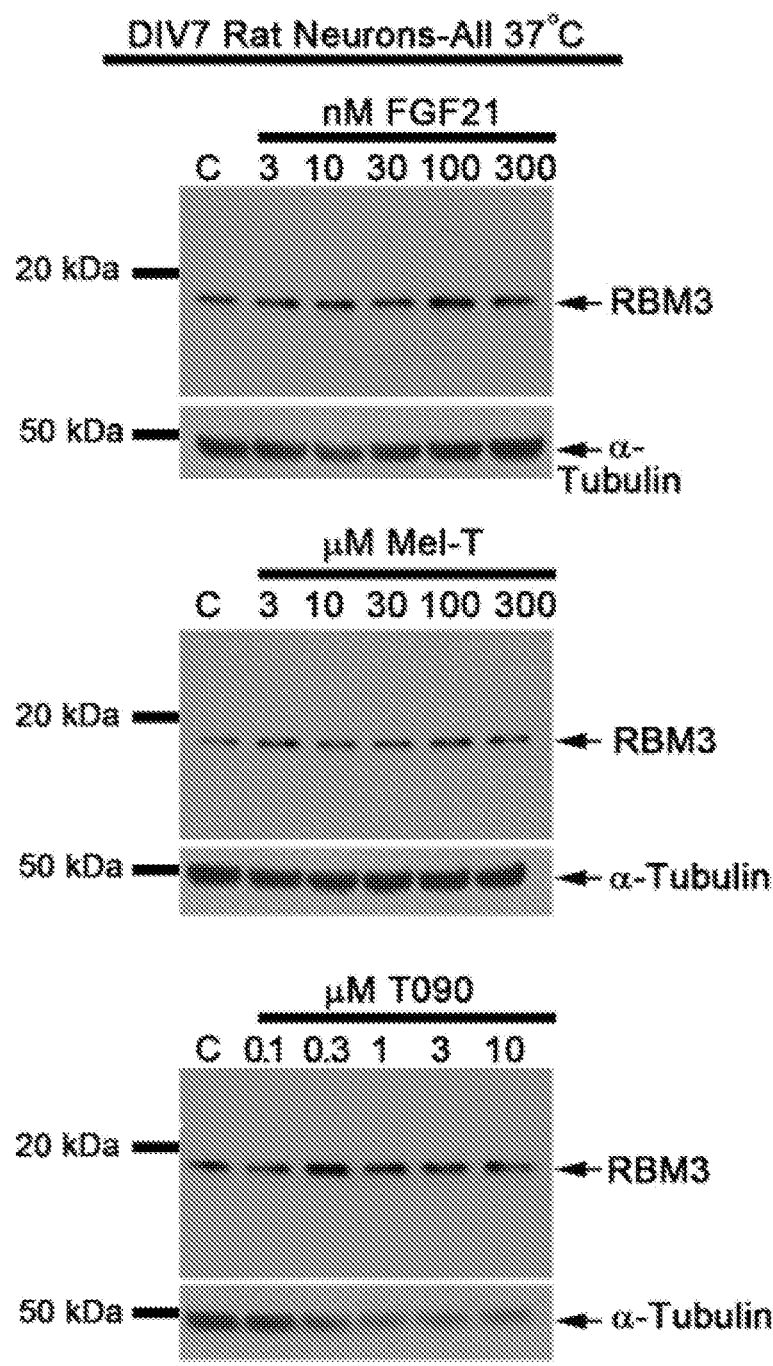
Figure 6C:
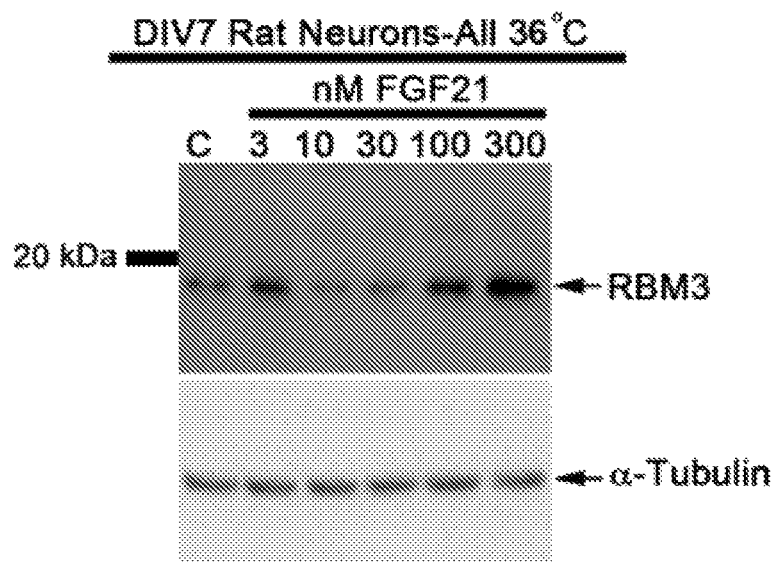
Figure 6D:
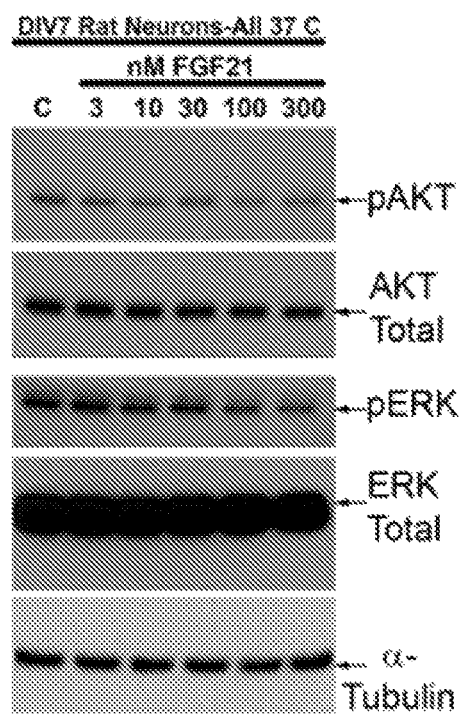
Figure 6E:
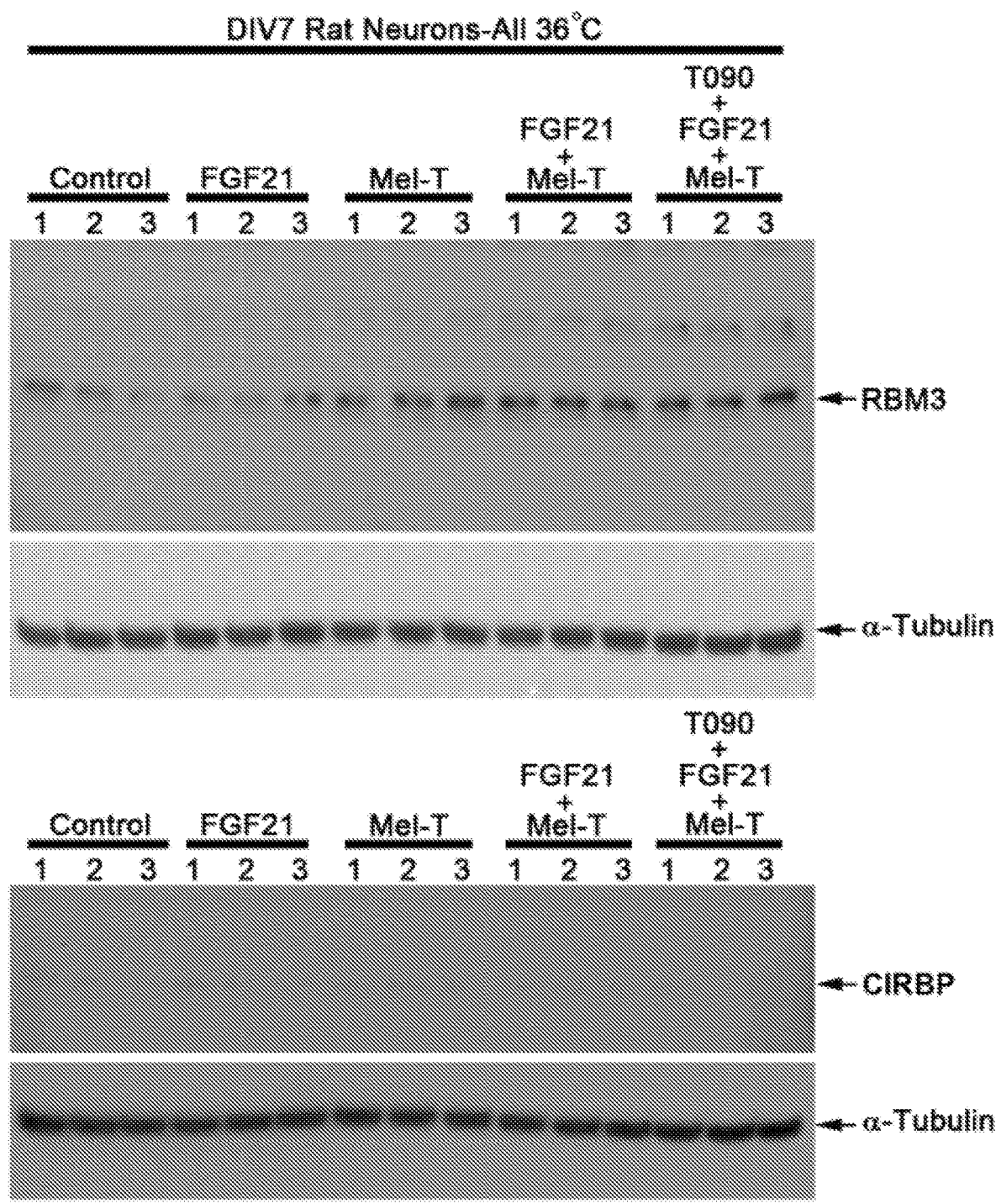
Figure 6F:
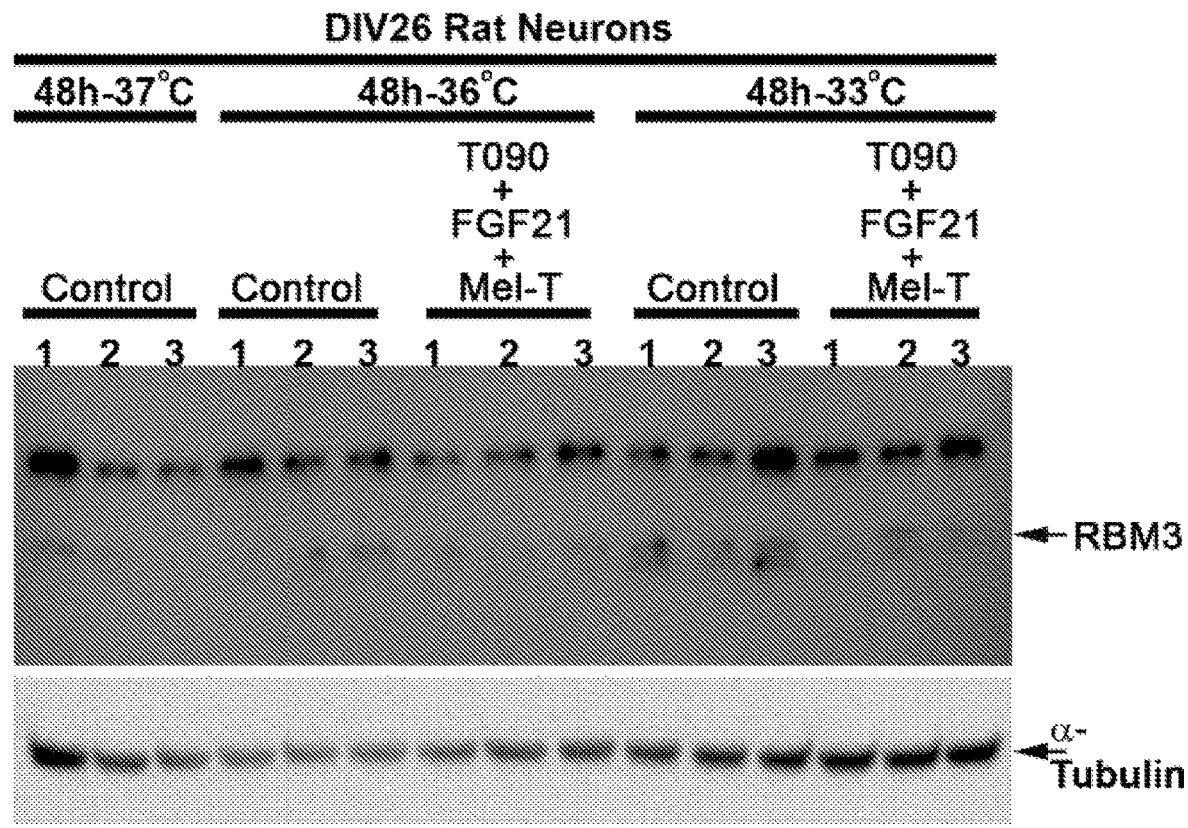

Several agents were then screened for potential RBM3 augmenting effects in young neurons. DMSO (drug dissolving vehicle) did not alter baseline RBM3 levels (data not shown). In young DIV6 neurons, cooling to 36° C. for 24 h was insufficient duration to induce RBM3 (FIG. 6A) (i.e. in contrast RBM3 was mildly increased in DIV6 neurons by 36° C. for 48 h; FIG. 6B). However, addition of fibroblast growth factor 21 (FGF21) or melatonin (Mel-T) during the shorter 24 h cooling period augmented RBM3 levels at 36° C. (FIG. 6A). The LXR agonist T090 mildly increased RBM3 levels at both 37° C. and 36° C. Neither SRT1720 (Sirtuin antagonist) nor AZD1080 (GSK-3β antagonist) increased RBM3 levels at 37° C. and 36° C. Similarly, 24 h treatment with increasing dose of FGF21, Mel-T, and T090 had minor effects on RBM3 protein expression in DIV7 neurons cultured at 37° C. (FIG. 6B). In contrast, FGF21 increased RBM3 above baseline in a bi-phasic manner when cultured at 36° C. (FIG. 6C). As a positive control we also tested if FGF21 activated AKT/ERK survival signaling at 37° C. as previously reported in neurons (Leng Y, et al. (2015) FGF-21, a novel metabolic regulator, has a robust neuroprotective role and is markedly elevated in neurons by mood stabilizers. Mol Psychiatr 20:215-223). Paradoxically, AKT/ERK phosphorylation was decreased 24 h later potentially suggesting feedback inhibition (FIG. 6D). Combination therapy of drugs increased RBM3 levels above baseline in DIV7 neurons cooled to 36° C. CIRBP levels were unaffected by treatments (FIG. 6E). Finally, 48 h to 36° C. alone or with drug combinations failed in induce RBM3 in mature DIV26 neurons. RBM3 was marginally increased in control neurons cooled to 33° C. for 48 h (FIG. 6F).

A single study has tested if extremely mild hypothermia (a temperature reduction of only 2° C.) upregulates cold-stress proteins. In that study, long-term maintenance of embryonic stem cells to 35° C. did not increase mRNA levels of RBM3/CIRBP (Belinsky G S, et al. (2013) Mild hypothermia inhibits differentiation of human embryonic and induced pluripotent stem cells. Biotechniques 55:79-82). Here we report in pure primary cortical neurons and astrocytes that either ultra-mild hypothermia (UMH) to 36° C. or traditional clinically used mild hypothermia levels to 33° C. increase protein levels of RBM3. Notably, potentially harmful CIRBP did not increase in neurons.

RBM3 is developmentally regulated. It is abundant in postnatal brain but low in adults (Pilotte J, et al. (2011) Widespread Regulation of miRNA Biogenesis at the Dicer Step by the Cold-Inducible RNA-Binding Protein, RBM3. Plos One PLoS ONE 6(12): e28446. Doi:10.1371/journal.pone.0028446). It was anticipated that cold stress would induce RBM3 with greater amplitude in young neurons. Consistent with that prediction 36° C. robustly increased RBM3 in young DIV6-DIV11 neurons but not in mature DIV26 cultures. The mechanism(s) regulating inhibition of RBM3 during CNS development are unclear. Neurons in culture spontaneously fire excitatory potentials beginning around DIV7-10 followed by other progressive biochemical changes including alterations in expression of glutamatergic AMPA vs. NMDA receptors DIV14-21 (Zona C, et al. (1994) Age-dependent appearance of synaptic currents in rat neocortical neurons in culture. Synapse 18:1-6 and Lin Y C, et al. (2002) Development of excitatory synapses in cultured neurons dissociated from the cortices of rat embryos and rat pups at birth. J Neurosci Res 67:484-493). Neurons adopt a more stable adult phenotype by DIV25 (Lesuisse C, et al. (2002) Long-term culture of mouse cortical neurons as a model for neuronal development, aging, and death. J Neurobiol 51:9-23). We speculate that synaptic activity and other coordinated developmental processes regulate epigenetic changes suppressing protective RBM3 in adult brain.

Clinically conventional levels of mild TH have greater efficacy in newborns than adults with hypoxic-ischemic brain injury (Shankaran S, et al. (2005) Whole-body hypothermia for neonates with hypoxic-ischemic encephalopathy. *N Engl J Med* 353:1574-1584 and Nielsen N, et al. (2013) Targeted temperature management at 33 degrees C. versus 36 degrees C. after cardiac arrest. *N Engl J Med* 369:2197-2206). RBM3 is more easily induced by hypothermia in developing neurons and thus may be an underappreciated component of endogenous neuroprotective responses activated by TH in the young. The American Academy of Pediatrics recently published 2014 recommendations to enhance/extend TH in community hospitals for treatment of neurological injury in neonates. It will be important to understand if RBM3 has a role in brain recovery in that population.

Pharmacological Strategies to Augment RBM3 Upregulation in Young and Mature Neurons.

RBM3 signaling is downregulated in adult brain. One study demonstrated methodology to upregulate RBM3 in adult brain of non-hibernating animals. In that report, deep hypothermia to 16° C. was used in combination with 5-AMP injection to induce a hypometabolic state which mimics conditions in hibernating animals (Peretti D, et al. (2015) RBM3 mediates structural plasticity and protective effects of cooling in neurodegeneration. Nature 518, 236-239). Induction of RBM3 by deep cooling/5-AMP injection is ill-advised in the setting of acute brain injury. 5-AMP is well known to chemically induce hypothermia. Unfortunately, its benefits as an easy strategy to lower core body temperature are eclipsed by serious side effects including profound hypotension and hyperglycemia, which together aggravate ischemic brain injury (Zhang F, et al. (2009) When hypothermia meets hypotension and hyperglycemia: the diverse effects of adenosine 5'-monophosphate on cerebral ischemia in rats. J Cerebr Blood F Met 29:1022-1034). Furthermore, it is well known that deep hypothermia can exacerbate ischemic brain damage whereas mild cooling is protective (Weinrauch V, et al. (1992) Beneficial effect of mild hypothermia and detrimental effect of deep hypothermia after cardiac arrest in dogs. Stroke 23:1454-1462). In an attempt to identify drugs which might safely augment RBM3 signaling under mild hypothermic conditions, several agents were tested, including the hormones FGF21 and melatonin. Both molecules cause slight body temperature reduction in mammals. The LXR agonist T0901317 is a potential caloric restriction (CR) mimetic known to upregulate RBM3 mRNA in mouse liver as measured by microarray (Corton J C, et al. (2004) Mimetics of caloric restriction include agonists of lipid-activated nuclear receptors. J Biol Chem 279:46204-46212). We also tested Sirtuin agonist SRT1720—which belongs to a different class of potential CR mimetic drugs (Smith J J, et al. (2009) Small molecule activators of SIRT1 replicate signaling pathways triggered by calorie restriction in vivo. Bmc Syst Biol 3:31). Finally, we tested the GSK-3β inhibitor AZD1080 (Georgievska B, et al. (2013) AZD1080, a novel GSK3 inhibitor, rescues synaptic plasticity deficits in rodent brain and exhibits peripheral target engagement in humans. J Neurochem 125: 446-456). GSK-3β inhibitors activate the developmentally essential Wnt/β-catenin pathway (Castelo-Branco G, et al. (2004) GSK-3beta inhibition/beta-catenin stabilization in ventral midbrain precursors increases differentiation into dopamine neurons. J Cell Sci 117:5731-5737).

FGF21 and melatonin increased hypothermia-induced RBM3 in young neurons cooled to 36° C. but failed to do so in mature neurons or young neurons incubated at 37° C. T0901317 mildly induced RBM3 in young neurons at both temperatures but failed to do so in mature neurons. SRT1720 and AZD1080 did not affect RBM3 levels in young neurons. Our results suggest that FGF21 and/or melatonin merit pre-clinical evaluation in vivo as promoters of RBM3 in the immature injured brain. Of note, melatonin reportedly augments hypothermia (33.5° C.) induced neuroprotection in a piglet model of perinatal ischemic brain injury (Robertson N J, et al. (2013) Melatonin augments hypothermic neuroprotection in a perinatal asphyxia model. Brain 136:90-105). It remains to be determined if RBM3 could have contributed to improved outcomes in that study. More work is needed to investigate the mechanism(s) underlying RBM3 induction by those compounds in pre-clinical models of developmental brain injury.

Results herein suggest that RBM3 is neuroprotective in acute brain injury such as in stroke, cardiac arrest, or traumatic brain injury. A major function of RBM3 is to stimulate GPS (Dresios J, et al. (2005) Cold stress-induced protein Rbm3 binds 60S ribosomal subunits, alters microRNA levels, and enhances global protein synthesis. Proc Natl Acad Sci USA 102:1865-1870; Liu Y, et al. (2013) Cold-induced RNA-binding proteins regulate circadian gene expression by controlling alternative polyadenylation. Sci Rep 3:2054; and Smart F, et al. (2007) Two isoforms of the cold-inducible mRNA-binding protein RBM3 localize to dendrites and promote translation. J Neurochem 101:1367-1379). Loss of GPS persists in vulnerable CA1 neurons after brain ischemia, for example, and coincides with delayed cell death (Vosler P S, et al. (2012) Ischemia-induced calpain activation causes eukaryotic (translation) initiation factor 4G1 (eIF4GI) degradation, protein synthesis inhibition, and neuronal death (vol 108, pg 18102, 2011). Proc Natl Acad Sci USA 109:4021-4021). Interestingly, TH has been shown to reverse aberrant GPS in injured CA1 neurons, although the underlying mechanism(s) have not been elucidated (Yamashita K, et al. (1991) Mild hypothermia ameliorates ubiquitin synthesis and prevents delayed neuronal death in the gerbil hippocampus. Stroke 22:1574-1581 and Widmann R, et al. (1993) Protective Effect of Hypothermia on Hippocampal Injury after 30 Minutes of Forebrain Ischemia in Rats Is Mediated by Postischemic Recovery of Protein-Synthesis. J Neurochem 61:200-209). As RBM3 is a cold shock-induced protein, logic suggests that it is in some way involved in TH-mediated alterations in GPS. Furthermore, increasing RBM3 in diseased hippocampus is thought to augment GPS which improves synaptic plasticity/sparing in vivo (Peretti D, et al. (2015) Nature 518, 236-239). Here we show for the first time that cooling neurons to 36° C. is sufficient to increase RBM3 and is associated with enhanced GPS.

Unexpectedly, GPS was not increased by exposure to 33° C.—despite higher RBM3 levels. That observation can be explained by overall greater inhibition of GPS in the 33° C. group. Hypothermia is well known to temporally decrease rates of GPS but at the same time upregulate cold stress proteins prior to rewarming. In this example, before harvesting neurons, all groups received a 1 h re-warming period to 37° C. in media following 48 h of experimental temperature exposure. The duration of time necessary for GPS to return to normal after cooling in primary neurons has not been reported to the best of our knowledge. It might be that 1 h rewarming was insufficient to allow return of normal translational mechanisms in the 33° C. group, delaying RBM3 from maximally augmenting GPS. In contrast 36° C., being closer to normothermia, might not alter baseline GPS to the same extent thus facilitate the ability of RBM3 to augment protein translation at that temperature. This interpretation is supported by results on eIF2α. eIF2α is a master regulation of cap-dependent protein synthesis. Phosphorylation at Ser51 is a potent mechanism cells use to shutdown global protein translation (Clemens MJ (2001) Initiation factor eIF2 alpha phosphorylation in stress responses and apoptosis. Prog Mol Subcell Biol 27:57-89). We found eIF2α phosphorylation was greatest in the 33° C. group.

Phosphorylation of eIF2α did not increase in astrocytes cooled to 36° C. or 33° C. for 48 h. Thus, in vitro, astrocytes appear more resistant than neurons to translational shutdown by eIF2α inhibition after mild hypothermia. The cause of that resistance is unclear but may relate to differences in biochemical mechanisms regulating energy and metabolism; for instance access to glycogen stores in astrocytes may alter protein translation homeostasis. Alternatively, differences might relate to relative cell culture conditions. Astrocytes were maintained, and temperature treatments initiated, under high serum conditions (i.e. 10% FBS). In contrast, neurons were maintained, and temperature treatments initiated, with serum free neurobasal/B27 supplement. High growth factor support in astrocytes might make them resistant to mild translational inhibition by hypothermia. Nevertheless, RBM3 was potently induced by 33° C. and mildly increased by 36° C. in astrocytes after 48 h. Thus this work confirms 36° C. can increase RBM3 in multiple CNS cell types. Future studies might test if RBM3 is differentially induced by cooling in type-1 versus type-2 astrocytes—the former being the majority of cells in monolayer cultures in this study.

Besides its effect on GPS, RBM3 has other beneficial actions which have been noted. RBM3 knockdown blocks mild TH-induced neuroprotection in vitro (Chip S, et al. (2011) The RNA-binding protein RBM3 is involved in hypothermia induced neuroprotection. Neurobiol Dis 43:388-396). In contrast, RBM3 overexpression prevents death in serum starved cells (Wellmann S, et al. (2010) The RNA-Binding Protein RBM3 Is Required for Cell Proliferation and Protects Against Serum Deprivation-Induced Cell Death. Pediatr Res 67:35-41).

Tiny temperature shifts are increasingly being recognized to influence outcomes in critically ill patients. Recent trials suggest that targeted temperature management (TTM) to 36° C. is equally effective on neurologic outcome and mortality in brain injured patients compared to conventional TH (Nielsen N, et al. (2013) N Engl J Med 369:2197-2206 and Moler F W, et al. (2015) Therapeutic hypothermia after out-of-hospital cardiac arrest in children. N Engl J Med 372:1898-1908). Hyperthermia (such as by fever) exacerbates neuronal death after brain ischemia (Noor R, et al. (2003) Effects of hyperthermia on infarct volume in focal embolic model of cerebral ischemia in rats. Neurosci Lett 349:130-132). Clinically, it has been shown that increases in 1° C. body temperature in the initial 72 h post hypoxic ischemic period is associated with an over 3-fold increase in the odds of poor outcome in newborns (Laptook A, et al. (2008) Elevated temperature after hypoxic-ischemic encephalopathy: risk factor for adverse outcomes. Pediatrics 122:491-499). Prevention of fever is likely a key mechanism of benefit with TTM. Nevertheless it is tempting to speculate that temperatures representing UMH might also increase protective cold shock proteins.

Ironically, 36° C. has been used as the temperature in the control group in many studies testing traditional levels of TH but our data suggest it may not represent a normothermic control—at least in young (Onesti S T, et al. (1991) Transient hypothermia reduces focal ischemic brain injury in the rat. Neurosurgery 29:369-373 and Clark R S, et al. (1996) Mild posttraumatic hypothermia reduces mortality after severe controlled cortical impact in rats. J Cereb Blood Flow Metab 16:253-261). Contrary to concern, classic studies by Busto et al. in adult rodents show that mild hypothermia to 33° C. or 34° C. dramatically improves histological outcomes after global forebrain ischemia compared to 36° C. controls (Busto R, et al. (1987) Small differences in intraischemic brain temperature critically determine the extent of ischemic neuronal injury. J Cereb Blood Flow Metab 7:729-738). Results herein suggest that it may be important to recognize that extremely mild levels of hypothermia may have biological effects in some circumstances. Temperatures slightly below normothermia may activate molecular cold shock mechanisms, especially in the very young—until now thought to be only induced by traditional levels of TH. We believe it is appropriate to consider these extremely mild temperature reductions to represent UMH (>35.5° C. to 36° C. or >35.5° C. to 36.5° C.). UMH may have important distinctions from "mild hypothermia" which technically includes 36° C. but more colloquially implies temperatures proven to induce neuroprotection (35.5-33° C.). Notwithstanding the latter definition, UMH might still be neuroprotective over and above benefits gained by preventing fever after brain injury—depending on the myriad circumstances of the model (such as in neonates) or clinical condition. In summary, here we show for the first time that UMH at 36° C. induces a bonafide cold-stress response in young neurons and astrocytes in vitro.

Example 2—Age is a Factor in RBM3 Expression

Figure 7:
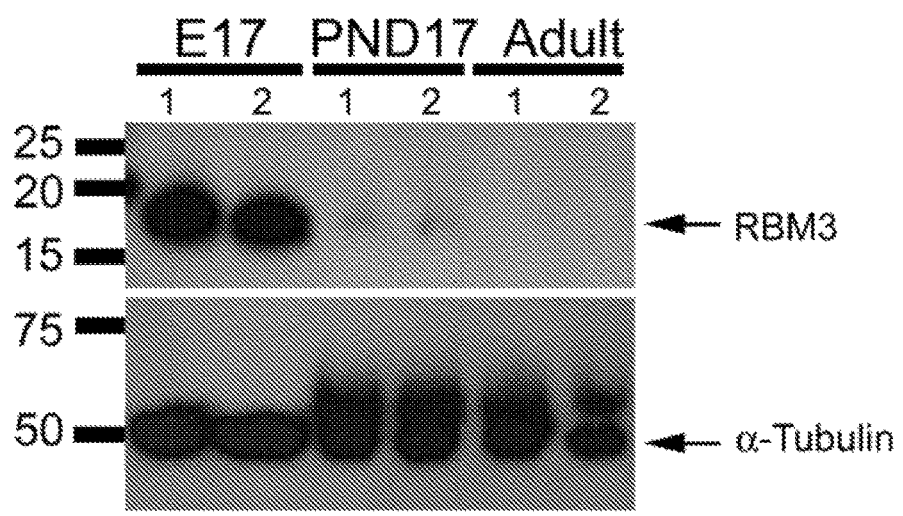
FIG. 7 is a Western blot comparing RBM3 expression in embryonic (E17), neonatal postnatal day 17 (PND17).

RBM3 is present in brain postnatally but expression declines with age. Here it is reproducibly confirmed it is detectable using authenticated reagents at baseline in naïve PND17 rat cortex and absent in adults (FIG. 7). Levels are highest in embryonic (E17) brain.

Figure 8A:
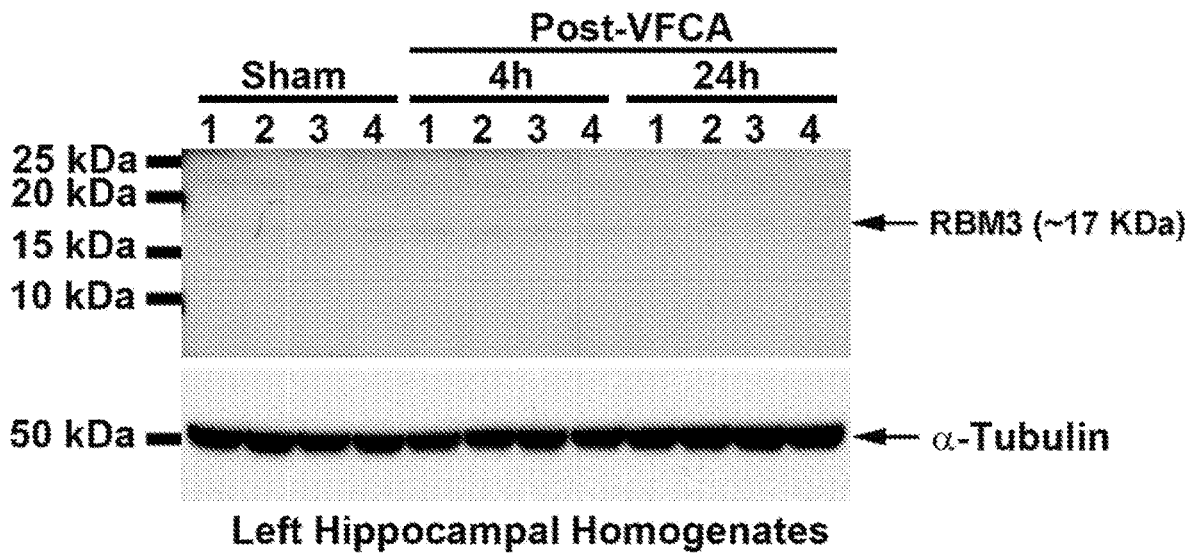
FIG. 8A is a Western Blot showing post-VFCA (ventricular fibrillation (VF) cardiac arrest) expression of RBM3 in adult rats.
Figure 8B:
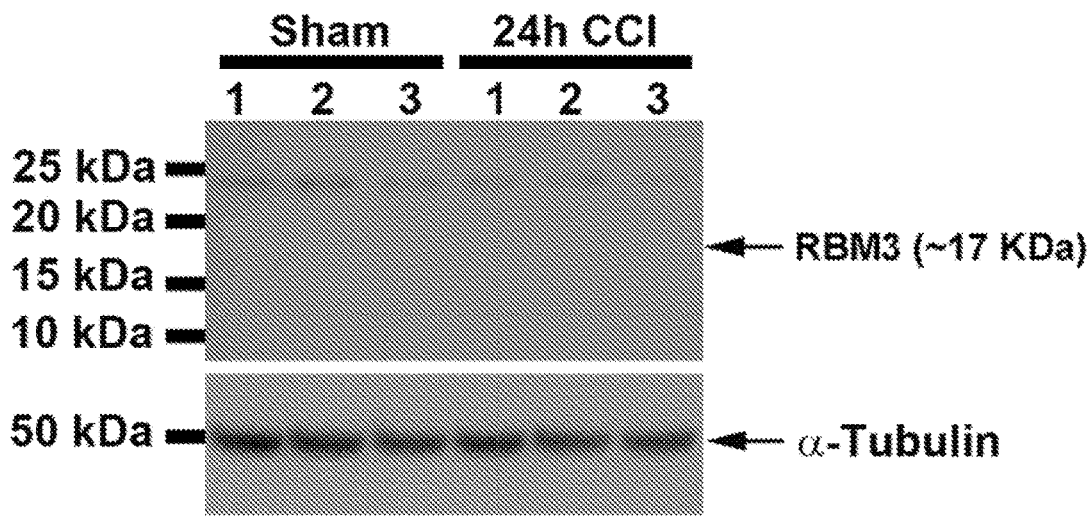
FIGS. 8B and 8C are Western Blots showing RBM3 expression in cortical (FIG. 8B) and hippocampal (FIG. 8C) homogenates of controlled cortical impact-traumatic brain injury (CCI-TBI) rats.
Figure 8C:
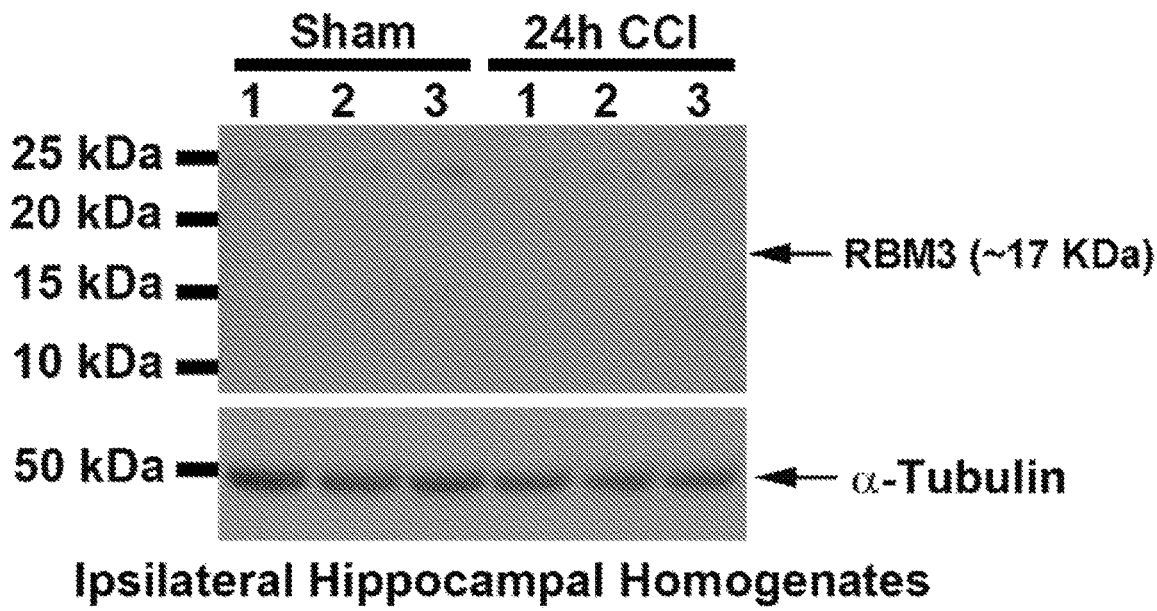
Figure 8D:
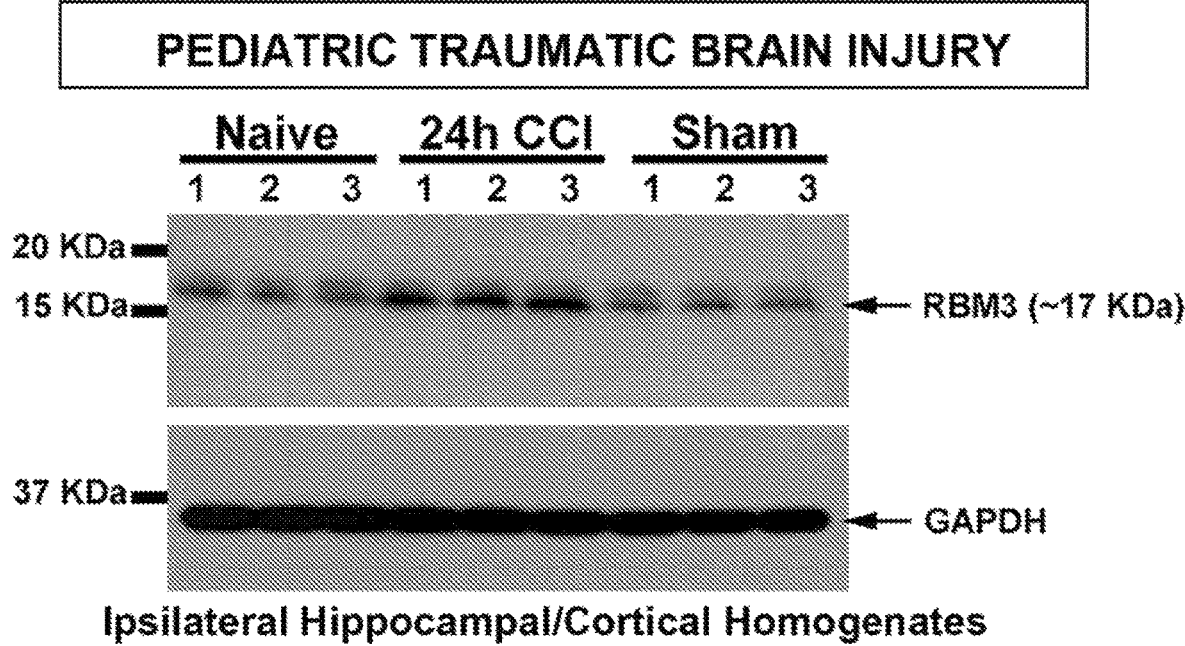
FIG. 8D is a Western Blot showing RMB3 expression in PND17 rats.
Figure 8E:
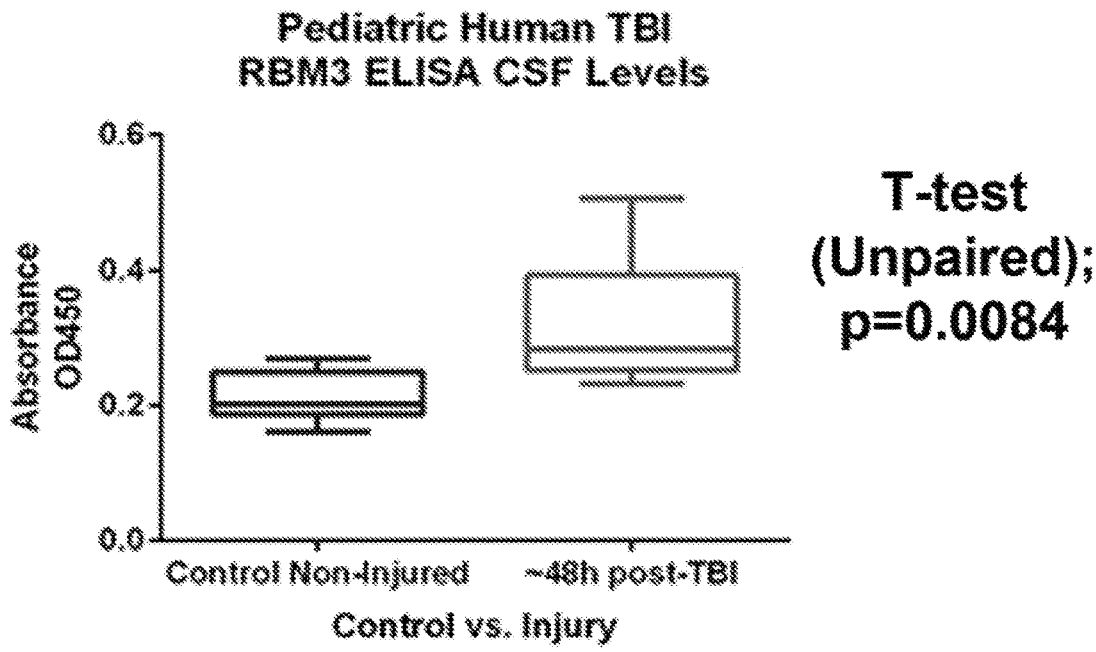
FIG. 8E is a graph showing RMB3 expression, as determined by ELISA in cerebrospinal fluid (CSF) of human pediatric TBI patients.

Adult rats given ventricular fibrillation (VF) cardiac arrest (VFCA) have very low levels of RBM3 at baseline and post-injury (FIG. 8A). Adult rats given CCI-TBI also have nearly undetectable levels of RBM3 before and after injury (FIGS. 8B and 8C). (3) In contrast, baseline RBM3 is detectable in PND17 rats and mildly increases after TBI-CCI (FIG. 8D). Finally, we found that pediatric patients have elevated RBM3 in CSF after a TBI (FIG. 8E, the control group is n=10, and the ~48 h post-TBI group is n=5.).

Example 3—β-klotho and RBM3 Expression

Figure 9:
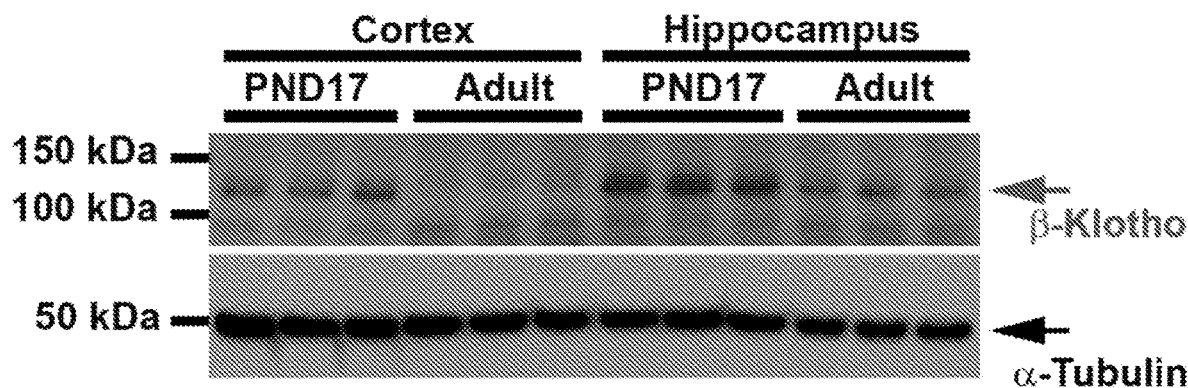
FIG. 9 is a Western Blot showing cortical and hippocampal β-klotho expression in PND17 and adult rats.

Endocrine FGFs uniquely depend on adaptor proteins (α-klotho or β-klotho) to activate target FGF receptors. Thus, an effect of endocrine FGFs on tissues depends on expression of klotho proteins (β-klotho is required for FGF21 activity). The brain has very low levels of β-klotho (in contrast FGFRs are ubiquitous). In adults, β-klotho is expressed in a few brain regions including suprachiasmatic nucleus, area postrema, nucleus tractus solitarii, and vagal nodose ganglia. FGF21 activity is restricted to these regions in adults. It has not been reported if β-klotho levels differ in young vs. adult brain. Here, it is found that β-klotho (~120 kDa) is present in PND17 cortex whereas it is absent in adult cortex (FIG. 9). Similarly, levels are much higher in PND17 hippocampus vs. adult (FIG. 9).

Figure 10A:
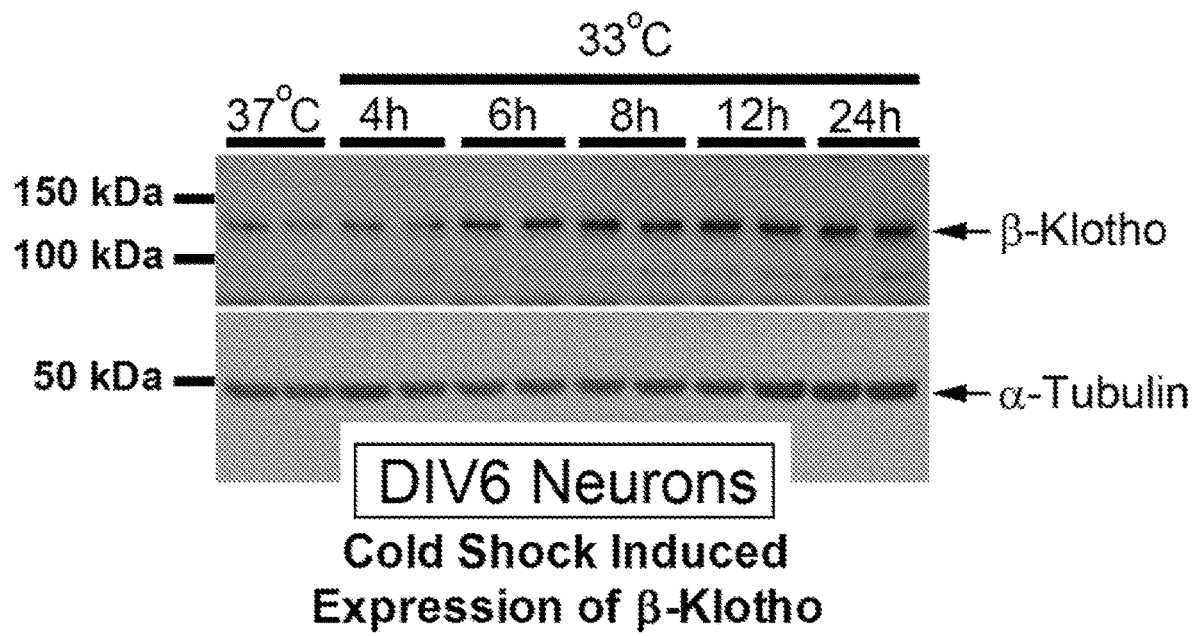
FIG. 10A is a Western Blot showing induction of β-klothos during hypothermia in DIV6 neurons.
Figure 10B:
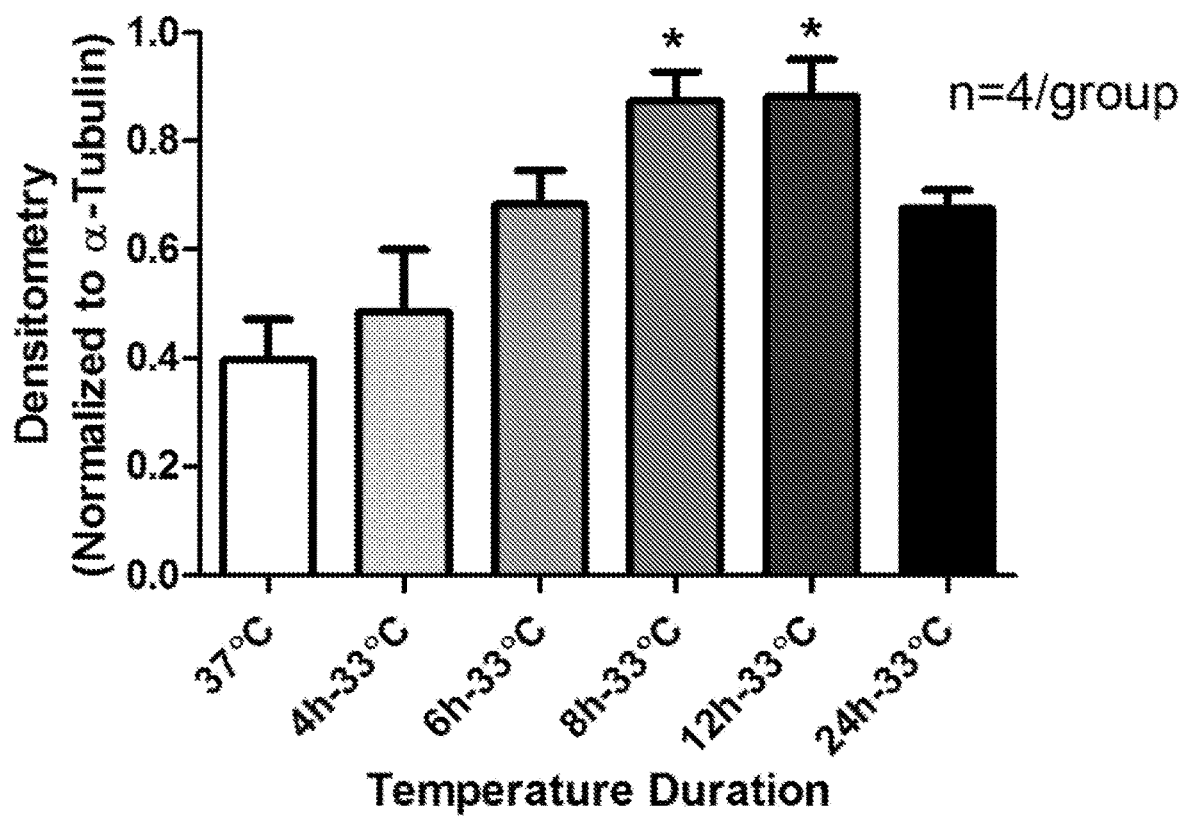
FIG. 10B is a graph of α-tubulin-normalized densitometry values for the Western Blot of FIG. 10A.

An elegant evolutionary design would be for the brain to capitalize on FGF21 biology only during cold stress (e.g., during hibernation) by upregulating β-klotho. Such a signaling arrangement would perfectly link the timing of hibernation with FGF21 metabolic changes in brain (i.e. a novel hypothermia coincidence detection system in brain) activating only when cognition is not needed. This would mean that β-klotho is a novel cold induced protein. Few such proteins have been discovered in mammals to date (there are ~8, with RBM3 being the best known) Unlike most genes, cold shock proteins express their mRNA and/or protein even during hypothermia. The mechanisms they employ to translate proteins can bypass the 5' Cap-dependent process. FIG. 6A shows Western blot data from neurons subjected to 33° C. hypothermia. β-klotho increases linearly with longer durations of cold-exposure. This shows that β-klotho is induced by cold stress, and therefore must be a cold shock protein. Data showing that β-klotho rapidly and robustly increases in primary neurons cooled to 33° C. (FIGS. 10A and 10B) suggests that it is a new member of the cold shock protein family.

Example 4—RBM3 is Induced by TH/TTM in Young/Adult Rats and FGF21 Augments RBM3 and CNS Protection by TH/TTM TTM and TH. PND17 and 12 wk adult Sprague Dawley rats receive external cooling. Endogenous RBM3/β-Klotho levels is compared in male and female rats. The TTM group is cooled to 36° C. within ~5 min then maintained to target temperature for 7 h: 25 min. The TH group is cooled to 33° C. over ~1 h then to target temperature for 3 h: 15 min then rewarmed at a rate of 1° C./hr. Time spent<37° C. is equal in all groups (8 h: 30 mins). FIGS. 11A, 11B, 12A, and 12B illustrate exemplary protocols for these groups.

PND17 CCI. Rats are given CCI in Aim 271, 72. Isoflurane anesthetized ~35 g PND17 rats are craniotomized at the left parietal cortex and injured by pneumatic impactor (velocity, 4 m/s; depth, 2.5 mm). Randomization is by (A) temperature (37° C., 36° C., 33° C.), and (B)±CCI±1 mg/kg FGF21 or PBS vehicle. Two bolus IV injections of drug will be given—at the start and end of TH/TTM. Technicians are blind to treatments.

MWM Behavior. Rats are given MWM testing 73, 74. Our MM consists of a pool (180 cm diameter, 60 cm deep) filled to 28 cm and goal platform (10 cm diameter) positioned 1 cm below the water surface from the southwest wall. Extra-maze cues remain constant. Water is ~24° C. A video camera records swim movement (PC-based tracking). MM testing will be performed on d14-20 post-injury ensuring motor recovery and sufficient age to perform the task. Motor skill is assessed measuring swim speed proving cognitive performance is not confounded by motor deficits.

Cell Death. Histology is done as we reported 74, 75. Surviving CA1/CA3 cells are counted in H & E stained brain sections 7 d post-injury by unbiased stereology. 21 d contusion volume is measured after MWM in separate rats Experimental Procedures and Endpoints: Blood (100-500 uL) is collected to assay endogenous/exogenous FGF21 (ELISA), glucose, blood gases/chemistry, and estrogen/progesterone (adult females). Blood is collected at baseline and hypothermia: 5 min, 30 min 1 h, 2 h, 4 h, 6 h, 8.5 h. Rats are sacrificed by decapitation after 8.5 h hypothermia for protein/mRNA. Brain (cortex, hippocampus, and cerebellum), heart, muscle liver, lung, and kidney are flash frozen. A subgroup is sacrificed by perfusion fixation for unbiased stereology. A cohort of rats is tested on the MWM then sacrificed for 21 d contusion analysis (techs blind to treatment).

Figure 12B:
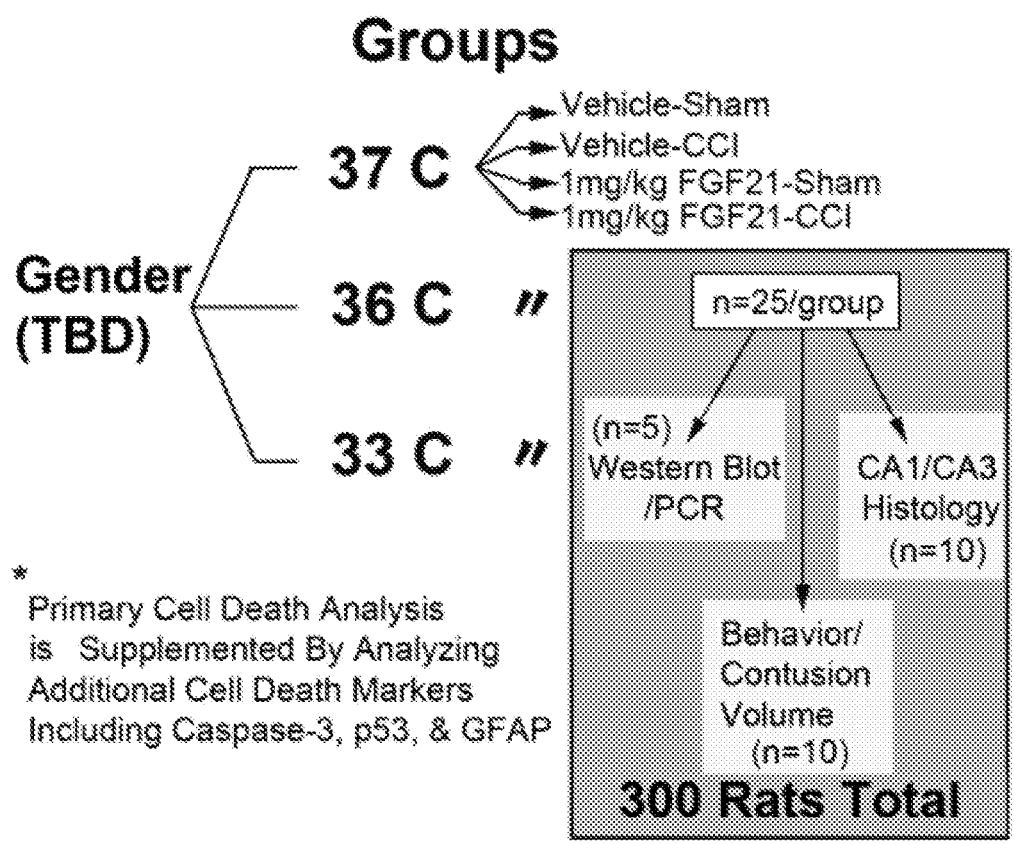

Based on the injury effect and variance observed in this model, a sample size of n=10 rats/group is sufficient to detect a 40% reduction in MWM latency; n=10 is also sufficient for lesion volume 77. Power calculations (90% power for a 25% change) using standard deviations from previous studies indicate n=10 is required for CCI-histology. N=5 rats/group is used for protein/mRNA statistics 78, 79. Aim 1 requires 30 PND17 and 30 adult rats (n=5/group; FIG. 11B). Aim 2 requires 300 PND17 rats (FIG. 12B).

It is predicted that TH/TTM increases RBM3 in PND17 brain; TH increases RBM3 in adult brain; and FGF21 augments TH/TTM induced neuroprotection after a CCI at PND17.

Example 5—β-Klotho Mediates FGF21 Induced RBM3 Upregulation and Neuroprotection

The following tests the hypothesis that β-klotho mediates FGF21 induced RBM3 upregulation in cooled neurons and if RNAi of β-klotho or RBM3 blocks FGF21 neuroprotection.

The independent relevant biological variables are temperature (37° C., 36° C., 33° C.), RNAi, and injury (Glutamate, STS, $H_2O_2$). The dependent variables are β-klotho/RBM3 protein levels, LDH release, CellTiter Blue (viability), and caspase-3/7 activity.

Cell culture. Day in vitro 6 (DIV6) mixed gender rat neurons are cultured using reported methods (Jackson T C, et al. Cold Stress Protein RBM3 Responds to Temperature Change in an Ultra-Sensitive Manner in Young Neurons. *Neuroscience.* 2015 Oct. 1; 305:268-78 and Jackson T C, et al. PHLPP1 splice variants differentially regulate AKT and PKCalpha signaling in hippocampal neurons: characterization of PHLPP proteins in the adult hippocampus. *J Neurochem.* November 2010; 115(4):941-955). Neurons are given TTM/TH as above, using rigorous tightly monitored/controlled conditions (Jackson T C, et al. *Neuroscience.* 2015 Oct. 1; 305:268-78).

Cell Death and Injury Measures. Cells are injured with glutamate, staurosporine, or $H_2O_2$ as reported (Jackson T C, et al. Pharmacological inhibition of pleckstrin homology domain leucine-rich repeat protein phosphatase is neuroprotective: differential effects on astrocytes. *J Pharmacol Exp Ther.* November 2013; 347(2):516-528 and Jackson T C, et al. Anthraquinone-2-sulfonic acid (AQ2S) is a novel neurotherapeutic agent. *Cell Death Dis.* 2013; 4:e451). Post-injury, neurons are given ±5 nM FGF21 (validated to augment RBM3 (Jackson T C, et al. *Neuroscience.* 2015 Oct. 1; 305:268-78)) ±hypothermia treatments for 24 h. Cell death is assayed 24 h later (DIV7) by LDH release, CellTiter Blue, and caspase-3/7 activity as in reported (Jackson T C, et al. *Cell Death Dis.* 2013; 4:e451).

High-Titer Lentivirus. Virus is made as reported (Jackson T C, et al. *J Neurochem.* November 2010; 115(4):941-955 and Jackson T C, et al. Pharmacological Inhibition of Pleckstrin Homology Domain Leucine-Rich Repeat Protein Phosphatase (PHLPP) is Neuroprotective: Differential Effects on Astrocytes. *Journal of Pharmacology and Experimental Therapeutics.* 2013 November; 347(2):516-528). β-klotho/RBM3 siRNA targeting plasmids are purchased from Origene and maxi prepped to obtain high quality transfection-ready DNA. Expression and packaging plasmids are mixed in HEK293Ta cells in T225 flasks. ~100 mL of virus containing media is ultra-centrifuged and suspended in 200 uL Opti-MEM (Average titer is ~$1 \times 10^{9-11}$/uL).

Protein Detection of β-klotho/RBM3. RBM3/β-Klotho protein levels are measured by Western as indicated above.

Experimental Procedures and Endpoints: At DIV0 (time of seeding) neurons are plated and transduced in 6- or 96-well plates. Neurons are transduced (Multiplicity of Infection; MOI 30) with control vector (non-targeting siRNA with GFP), β-klotho targeting, or RBM3 targeting. Neurons are injured, given 24 h FGF21±hypothermia, and cell death measured. Cells for Westerns are harvested in RIPA buffer for SDS-PAGE. 24 h cell death protocols are done as described above.

~30 pregnant rats are used in order to obtain sufficient embryonic brain tissue for primary rat neurons. Each transduction study is done in triplicate (6-well format) and n=10 replicates (96-well format). Three independent experiments (i.e. 3 different isolations) are pooled for statistical analysis.

It is predicted that RNAi of β-klotho would prevent FGF21 from increasing RBM3 and that FGF21 would fail to augment hypothermia-neuroprotection if β-klotho or RBM3 is inhibited by RNAi.

The following clauses describe various aspects of the invention.

1. A method of improving brain function in a hypothermic patient, comprising administering to the patient an amount of a fibroblast growth factor 21 (FGF21) protein effective to increase RNA binding motif 3 (RBM3) production in nerve cells of the patient.
2. The method of clause 1, further comprising inducing hypothermia in the patient prior to, during or after administration of the FGF21 protein to the patient, and optionally the FGF21 protein is administered up to 48 h before hypothermia is induced, at the induction of hypothermia, or up to 48 h after hypothermia is concluded.
3. The method of either clause 1 or clause 2, wherein the FGF21 protein is human FGF21 or a functional FGF21 mutant protein.
4. The method of any one of clauses 1-3, wherein the FGF21 protein is human FGF21, LY2405319, or PF-05231023.
5. The method of any one of clauses 1-4, wherein the FGF21 protein is a functional FGF21 mutant protein.
6. The method of clause 5, wherein the functional FGF21 mutant protein is an FGF21 protein conjugated to an antibody or a fragment thereof, and optionally wherein the antibody or fragment thereof lacks an antigen-binding site or it lacks an antigen binding site that binds a native human epitope.
7. The method any one of clauses 1-6, wherein the patient is a neonate (within 28 days of birth) or a pediatric patient (less than 18 years of age).
8. The method of any one of clauses 1-7, wherein the patient suffers from mild/moderate/severe traumatic brain injury (TBI), ventricular fibrillation cardiac arrest (VFCA), subarachnoid hemorrhage (SAH), subdural hematoma (SH), cerebral vasospasm, neonatal abusive head trauma (a.k.a. shaken baby syndrome), neonatal hypoxic ischemic encephalopathy (HIE), asphyxia cardiac arrest (ACA), treatment of spinal injury, prophylaxis in spinal surgery, stroke, and drug overdose.
9. The method of any one of clauses 1-7, wherein the patient is or will be undergoing cardiac surgery, spinal surgery, deep hypothermia circulatory arrest (DHCA), transplantation, or is subject to an emergency preservation and resuscitation (EPR) method.
10. The method of any one of clauses 1-9, wherein the patient's body temperature is maintained at a temperature ranging from 5° C. to 36.5° C., from above 33° C. and below 37° C., from 34° C. to 36.5° C., from 35.5° C. to 36.5° C., or 36° C.
11. The method of any one of clauses 1-9, wherein patient's body temperature is maintained at a temperature ranging from 33° C. to 35.5° C.
12. The method of any one of clauses 1-9, wherein patient's body temperature is maintained at a temperature ranging from 28° C. to 32° C.
13. The method of any one of clauses 1-9, wherein patient's body temperature is maintained at a temperature ranging from 11° C. to 29° C.
14. The method of any one of clauses 1-9, wherein patient's body temperature is maintained at a temperature ranging from 5° C. to 10° C.
15. The method of any one of clauses 1-14, wherein the patient's body temperature is reduced and/or maintained at least in part by one or more mechanical cooling devices, such as an ice pack, a fan, a circulating water blanket, a circulating cold air blanket, hydrogel-coated pads, a cooling helmet, a heat-exchange catheter, an extracorporeal heat exchange, intravenous/intravascular infusion of cooled normal saline or lactated Ringers solution, and heat-exchange by percutaneous indwelling lines.
16. The method of any one of clauses 1-14, wherein the patient's body temperature is initiated or maintained at least in part by administering a pharmacologic agent effective to lower a patient's body temperature, such as but not limited to anesthetics like isoflurane, sevoflurane, desflurane, halothane, propofol, fentanyl, morphine, opioids, and adenosine monophosphate, such as 5-AMP, 3-AMP, or 2-AMP, N-(2-aminoethyl)-N-(4-(benzyloxy)-3-methoxybenzyl)thiophene-2-carboxamide hydrochloride (M8-B), or melatonin.
17. The method of any one of clauses 1-16, wherein the FGF21 protein is delivered by intravenous, oral, intranasal, inhalation, intrathecal, or intracerebroventricular route.
18. The method of any one of clauses 1-17, wherein the amount of FGF21 protein effective to increase RNA binding motif 3 (RBM3) production in nerve cells of the patient ranges from 1 pg/kg to 500 mg/kg, and/or wherein the FGF21 protein is maintained in the hypothermic patient in an effective amount to increase RNA binding motif 3 (RBM3) production in nerve cells of the patient for at least 0.5, at least 1, at least 12, or at least 24 hours.
19. The method of any one of clauses 1-18, wherein the FGF21 protein is administered as a bolus, at multiple time points, or as a continuous infusion/release.
20. The method of any one of clauses 1-19, wherein the FGF21 protein is provided in a composition used to infuse a patient to establish and/or maintain hypothermia.
21. A method of inducing RBM3 in a nerve cell, comprising, contacting the nerve cell with an amount of an FGF21 protein effective to increase RNA binding motif 3 (RBM3) production in a nerve cell under hypothermic conditions.
22. The method of clause 21, further comprising inducing the hypothermic conditions prior to, during, or after contacting the nerve cells with the FGF21 protein, and optionally the FGF21 protein is administered up to 48 h before hypothermic conditions are induced, at the induction of hypothermic conditions, or up to 48 h after hypothermic conditions are concluded.
23. The method of either of clauses 21 or 22, wherein the hypothermic conditions are maintaining the nerve cells at a temperature ranging from 5° C. to 36.5° C., from above 33° C. and below 37° C., from 34° C. to 36.5° C., from 35.5° C. to 36.5° C., or 36° C.
24. The method of either of clauses 21 or 22, wherein the hypothermic conditions are maintaining the nerve cells at a temperature ranging from 33° C. to 35.5° C.
25. The method of either of clauses 21 or 22, wherein the hypothermic conditions are maintaining the nerve cells at a temperature ranging from 28° C. to 32° C.
26. The method of either of clauses 21 or 22, wherein the hypothermic conditions are maintaining the nerve cells at a temperature ranging from 11° C. to 29° C.

27. The method of either of clauses 21 or 22, wherein the hypothermic conditions are maintaining the nerve cells at a temperature ranging from 5° C. to 10° C.
28. The method of any one of clauses 19-27, wherein the FGF21 protein is human FGF21 or a functional FGF21 mutant protein.
29. The method of any one of clauses 19-28, wherein the amount of FGF21 protein effective to increase RNA binding motif 3 (RBM3) production in nerve cells of the patient ranges from 1 pg/kg to 500 mg/kg.
30. The method of any one of clauses 19-29, wherein which the FGF21 protein is maintained in an effective amount to increase RNA binding motif 3 (RBM3) production in nerve cells for at least 0.5, at least 1, at least 12, or at least 24 hours during the hypothermic conditions.
31. An FGF21 protein for use in treatment of mild/moderate/severe traumatic brain injury (TBI), ventricular fibrillation cardiac arrest (VFCA), subarachnoid hemorrhage (SAH), subdural hematoma (SH), cerebral vasospasm, neonatal abusive head trauma (a.k.a. shaken baby syndrome), neonatal hypoxic ischemic encephalopathy (HIE), asphyxia cardiac arrest (ACA), treatment of spinal injury, prophylaxis in spinal surgery, stroke, and drug overdose, or where a patient is or will be undergoing cardiac surgery, spinal surgery, deep hypothermia circulatory arrest (DHCA), transplantation, or is subject to an emergency preservation and resuscitation (EPR) method, wherein the patient is hypothermic.
32. The FGF21 protein of clause 31, wherein the hypothermic patient is human.
33. The FGF21 protein of either clause 31 or 32, wherein the patient is a neonate (within 28 days of birth) or a pediatric patient (less than 18 years of age).
34. The FGF21 protein of any one of clauses 31-33, wherein the patient's body temperature is maintained at a temperature ranging from 5° C. to 36.5° C., from above 33° C. and below 37° C., from 34° C. to 36.5° C., from 35.5° C. to 36.5° C., or 36° C.
35. The FGF21 protein of any one of clauses 31-34, wherein the FGF protein is human FGF21, LY2405319, or PF-05231023.
36. The FGF21 protein of any one of clauses 31-34, wherein the FGF21 protein is a functional FGF21 mutant protein.
37. The FGF21 protein of clause 36, wherein the functional FGF21 mutant protein is an FGF21 protein conjugated to an antibody or a fragment thereof, and optionally wherein the antibody or fragment thereof lacks an antigen-binding site or it lacks an antigen binding site that binds a native human epitope.
38. The FGF21 protein of any one of clauses 31-37, wherein the FGF21 is provided in a composition used to infuse a patient to establish and/or maintain hypothermia.
39. The FGF21 protein of any one of clauses 31-38, wherein the FGF21 is administered as a bolus, at multiple time points, or as a continuous infusion/release.
40. A method of preparing a kidney for transplantation in a donor patient, comprising prior to removal of the kidney from the donor patient, inducing hypothermia in the donor patient and administering an amount of an FGF21 protein to the donor patient effective to reduce the prevalence of delayed graft function in a recipient patient of a kidney.

Although the present invention has been described with references to specific details of certain embodiments thereof, it is not intended that such details should be regarded as limitations upon the scope of the invention except in so far as they are included in the following outline and claims.

We claim:

1. A method of treating acute brain injury in a patient, comprising administering to the patient an amount of a fibroblast growth factor 21 (FGF21) protein effective to increase cognition and/or motor function in the patient, wherein the amount of FGF21 protein is effective to increase RNA binding motif 3 (RBM3) production in the patient, wherein the acute brain injury is neonatal hypoxic ischemic encephalopathy (HIE), and wherein the patient is a neonatal patient.

2. The method of claim 1, further comprising inducing hypothermia in the patient prior to, during or after administration of the FGF21 protein to the patient.

3. The method of claim 1, wherein the FGF21 protein is:
   a. human FGF21 protein, or
   b. a functional FGF21 mutant protein.

4. The method of claim 3, wherein the FGF21 protein is selected from:
   a. LY2405319;
   b. PF-05231023, and
   c. an FGF21 protein conjugated to an antibody or a fragment thereof.

5. The method of claim 1, wherein the patient's body temperature is maintained at a temperature ranging from 5° C. to 36.5° C.

6. The method of claim 1, wherein the patient's body temperature is reduced and/or maintained at least in part by one or more mechanical cooling devices selected from the group consisting of an ice pack, a fan, a circulating water blanket, a circulating cold air blanket, hydrogel-coated pads, a cooling helmet, a heat-exchange catheter, an extracorporeal heat exchange, intravenous/intravascular infusion of cooled normal saline or lactated Ringers solution, and heat-exchange by percutaneous indwelling lines.

7. The method of claim 1, wherein the patient's body temperature is initiated or maintained at least in part by administering a pharmacologic agent effective to lower a patient's body temperature.

8. The method of claim 1, wherein the FGF21 protein is delivered by intravenous, oral, intranasal, inhalation, intrathecal, or intracerebroventricular route.

9. The method of claim 1, wherein the FGF21 protein is administered as a bolus, at multiple time points, or as a continuous infusion/release.

10. The method of claim 1, wherein the FGF21 protein is provided in a composition used to infuse a patient to establish and/or maintain hypothermia.

11. The method of claim 1, wherein the FGF21 protein is maintained in the patient in an effective amount to increase RNA binding motif 3 (RBM3) production in nerve cells of the patient for at least 0.5 hours.

12. A method of treating neonatal hypoxic ischemic encephalopathy (HIE) in a patient, comprising administering to the patient an amount of an FGF21 protein effective to decrease nerve cell injury in the patient, wherein the patient is a pediatric patient.

13. The method of claim 12, further comprising inducing a hypothermic condition prior to, during, or after administering the FGF21 protein to the patient.

14. The method of claim 13, wherein the hypothermic condition maintains the nerve cells at a temperature ranging from 5° C. to 36.5° C.

15. The method of claim 12, wherein the FGF21 protein is human FGF21 protein or a functional FGF21 mutant protein.

16. The method of claim 12, wherein which the FGF21 protein is maintained to increase RNA binding motif 3 (RBM3) production in nerve cells for at least 0.5 hours during the hypothermic conditions.

17. The method of claim 12, wherein the amount of FGF21 protein effective to decrease nerve cell injury in the patient is effective to increase cognition and/or motor function in the patient.

18. A method of preparing a kidney for transplantation in a donor patient, comprising prior to removal of the kidney from the donor patient, inducing hypothermia in the donor patient and administering an amount of an FGF21 protein to the donor patient effective to reduce the prevalence of delayed graft function in a recipient patient of a kidney.

* * * * *

UNITED STATES PATENT AND TRADEMARK OFFICE
CERTIFICATE OF CORRECTION

PATENT NO. : 11,638,745 B2
APPLICATION NO. : 15/573006
DATED : May 2, 2023
INVENTOR(S) : Travis C. Jackson et al.

It is certified that error appears in the above-identified patent and that said Letters Patent is hereby corrected as shown below:

On the Title Page

Item (73), Assignee, Line 2, delete "Cvctom of Hierher" and insert -- System of Higher --

Signed and Sealed this
Fourth Day of July, 2023

Katherine Kelly Vidal
Director of the United States Patent and Trademark Office

SEQUENCE LISTING

```
<160> NUMBER OF SEQ ID NOS: 6

<210> SEQ ID NO 1
<211> LENGTH: 157
<212> TYPE: PRT
<213> ORGANISM: Homo sapiens

<400> SEQUENCE: 1

Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Lys Asp Arg Glu Thr Gln Arg Ser Arg Gly
        35                  40                  45

Phe Gly Phe Ile Thr Phe Thr Asn Pro Glu His Ala Ser Val Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Gly Phe Gly Ala
                85                  90                  95

His Gly Arg Gly Arg Ser Tyr Ser Arg Gly Gly Gly Asp Gln Gly Tyr
            100                 105                 110

Gly Ser Gly Arg Tyr Tyr Asp Ser Arg Pro Gly Gly Tyr Gly Tyr Gly
        115                 120                 125
```

Tyr Gly Arg Ser Arg Asp Tyr Asn Gly Arg Asn Gln Gly Gly Tyr Asp
            130                 135                 140

Arg Tyr Ser Gly Gly Asn Tyr Arg Asp Asn Tyr Asp Asn
145                 150                 155

<210> SEQ ID NO 2
<211> LENGTH: 4432
<212> TYPE: DNA
<213> ORGANISM: Homo sapiens

<400> SEQUENCE: 2

| | | | | | |
|---|---|---|---|---|---|
| gaacactgct | cccttcgctt | tgctgtccct | tcctctcccc | accactccgc | tcctgctggc | 60 |
| ctcagccaat | cagcacgcac | gccgggacgc | gcaaggggaa | cgttccggga | cgttctcgct | 120 |
| acgtactctt | tatcaatcgt | cttccggcgc | agccccgtcc | ctgttttttg | tgctcctccg | 180 |
| agctcgctgt | tcgtccgggt | ttttacgtt | ttaatttcca | ggacttgaac | tgccatgtcc | 240 |
| tctgaagaag | gaaagctctt | cgtgggaggg | ctcaacttta | acaccgacga | gcaggcactg | 300 |
| gaagaccact | tcagcagttt | cggacctatc | tctgaggtgg | tcgttgtcaa | ggaccgggag | 360 |
| actcagcggt | ccaggggttt | tggtttcatc | accttcacca | acccagagca | tgcttcagtt | 420 |
| gccatgagag | ccatgaacgg | agagtctctg | gatggtcgtc | agatccgtgt | ggatcatgca | 480 |
| ggcaagtctg | ctcggggaac | cagaggaggt | ggctttgggg | cccatgggcg | tggtcgcagc | 540 |
| tactctagag | gtggtgggga | ccagggctat | gggagtggca | ggtattatga | cagtcgacct | 600 |
| ggagggtatg | gatatggata | tgacgttcc | agagactata | atggcagaaa | ccagggtggt | 660 |
| tatgaccgct | actcaggagg | aaattacaga | gacaattatg | acaactgaaa | tgagacatgc | 720 |
| acataatata | gatacacaag | gaataatttc | tgatccagga | tcgtccttcc | aaatggctgt | 780 |
| atttataaag | gttttggag | ctgcaccgaa | gcatcttatt | ttatagtata | tcaaccttt | 840 |
| gtttttaaat | tgacctgcca | aggtagctga | agacctttta | gacagttcca | tctttttttt | 900 |
| taaatttttt | ctgcctattt | aaagacaaat | tatgggacgt | ttgtagaacc | tgagtatttt | 960 |
| tcttttacc | agtttttag | tttgagctct | taggtttatt | ggagctagca | ataattggtt | 1020 |
| ctggcaagtt | tggccagact | gacttcaaaa | aattaatgtg | tatccaggga | cattttaaaa | 1080 |
| acctgtacac | agtgtttatt | gtggttagga | agcaatttcc | caatgtacct | ataagaaatg | 1140 |
| tgcatcaagc | cagcctgacc | aacatggtga | accccatct | gtactaaaca | taaaaaaatt | 1200 |
| agcctggcat | ggtggtgtac | gcctgtaatc | ccagtgactt | gggaggctga | ggcaggagaa | 1260 |
| tcgcttgaac | ccgggaggcg | gaggttgcag | tgagctaaga | tcgcgccact | gtactccagc | 1320 |
| ctgggcaaca | gcgagactcc | atctcaaaaa | aaaggaaat | gtgtatcaag | aacatgatta | 1380 |
| tccagcggta | ttttctaatt | cagatcatca | aactgattat | atagaagagt | tggctttaaa | 1440 |
| atgtttgcaa | atgtctttt | ttttttaata | ctggaagaaa | aaatattctg | ttgtgtctca | 1500 |
| tacagtgctt | aggatgtctt | tcacagagct | tattaaaaag | atgaaacctg | agaacaaact | 1560 |
| gctttattct | tactcagccc | atttgcaaa | ttaaaagtgg | gggcagaggt | gggcggatca | 1620 |
| cctgaggtca | ggagttcgag | accagcctgg | ccaacagggc | aaaacccat | ctctactaaa | 1680 |
| aatacaaaag | ttagcgggc | gtggtggcgg | gtgcatgtaa | tcccagctac | tcgggaggct | 1740 |
| gaggcaggag | aattgcttga | acccaggagg | cggaagttgc | agtgagctga | gattgtgcca | 1800 |
| ctgcactcca | gcctaggtga | cagcaagact | ctgtctcaaa | aaaaaaaaa | tggcacatca | 1860 |
| acgagaggga | ggcttggaga | atatttggtt | ggtgggtggg | cagggactgc | cagagggtta | 1920 |

```
ggtgtacatt gaggcctgag gcctgctgga attgggtttc cttaactggt ctcttatctt   1980
agtcccattg ttctgagaac ataagcacct aatctcatgg cgtgagctaa tccctatcat   2040
aaatagtggt accagttcat tccttcccct gaaatgatgg gggttgggca gagatgcact   2100
gaactcatct ttgtgtatga gggccatgag agaggcctgg tttgaaaaca atgctaagag   2160
ctcagattcc aggatttatg tagggctct tctacttccc aggtatttga cctcaggtga    2220
gtcatttaat ttcagcctta tgccatttta cattttctgt ggagggttag gttaattggc   2280
atataaagcc actgagaaga gttggcaaag ctctcagtca cggggatttg atcttttttg   2340
gtgtgtgtgt gtcttgggtg gtaaagtggt aattttgtaa ttctagctgg tcttagttcc   2400
tcagttctgc tcccttagt catggttctt tctagtggct gtattgaggc cccatggtg     2460
ttatccctcc attggttcta gtttggaaca gaaaaatctg ttgtattcat ggctttcacc   2520
tggctaatac tgagctaagt taccaccagg ttgcaaactc caggacatta ttgtcctgag   2580
ctgcctattc ccttgctggt gcgttgtgga accctgtatt attagttcca gtcctggagg   2640
cctgcctcct gagtttccca gctagttggg acaggcccca atatcccttc ttcctgtaac   2700
ccaaacagtc atgaatttgc tttggcaggt ggatggagac ttgggaactt ccacctcacc   2760
cactaagcca ggcccaggct atggggcatt gtggctaacc ccaccaggtg gatacttggt   2820
ctgaggacgc atcttattct gggcctttag ggagctaagg cagtgagaat tggcaggagg   2880
actgctgtga atgccttgta ggtcggggga ttggagggg tcctctgctc cctgtctctc    2940
aggatggcaa tgtacctctc accccagtg tcagctgagg taggatccat aatcagtaat    3000
attcctgcaa caaaatgttc ctaagtggaa tcaatgaaga ccaaaattta tttgtataac   3060
aactctaaac ctgctctgct ctgctgtgtt tacaatgtgc tttgtgatca tccagcccag   3120
ggagtcccag tctctggctg tctatctgct ctaaggaaga gagcccacag ttctctatag   3180
tgccatagtc tgtgatgaat aaagttccag atttgaggtc aaccccgac caccccttaaa   3240
gtgcttgttg gtctcctact ttggtttgtc ttcagcatcc aactgatgca catttgtcaa   3300
gaacccactg aggctagaaa cccccccaaac actcaaggta ccttgagaac atgtatccca  3360
agacctgcaa agaccaaaca catggcctgt aactactttt cactttcaag ccctggaact   3420
tgtctgtacc aaaaatcttt ctgaaccatt caccaaatct cttgtcaagg gccagaataa   3480
attaagagat tggcttttgg ttttcaatta ggctttcaag tcctaagccc aaccctcct    3540
atcccaccta ggcagaaatc acttcagatc cttgcttcct agtttaattt cttctctgcc   3600
tcagttataa catccataaa atggaaataa taatacccac ctcacacagg ggttaggagt   3660
gttttttgt tggttttttt ccagacaggg tctcactctg tctcccaggc tggagtgcag    3720
tggcacaatc tcggctcact gtaccctccg cctcccaggt tcaagcagtt tcatgcctc    3780
agcctcccaa gtagctggga ttacaggtgc ctgccaccac gcccggctaa ttttgtatt    3840
aatagagaca gggtttcacc gtgttgggca ggctggtcct gaactcctga cctcaagtga   3900
tccacccgcc tcggcctccc aaagtgctgg gattacaggc gtgagccacc acacctggcc   3960
taggagttaa gagtattaaa tgttaagaac agaccaagtc catcaaacag ctccacaccc   4020
ttgttccatg ttctggattg gggagttgtg ggggtggagg tgtagaactt ttaaaaagct   4080
tcttaaaata agttgctgtg aatacttcag gtatataaaa aaacattggt tgacaataag   4140
ccagtgttct gccattctta cctgcttatc aagacaaaac ctgctcaagt ccctgcccag   4200
ctgcattcca agtgttttca gtttggtgg taagacctga cctgaggctt cttataacct    4260
ttactcagtg ggaatatgca tacagttcac tacagaaata tttgtattta cttagaggaa   4320
```

```
gtgccctgga tctgggggcg ggggggggcg gggggaatgg gtcttttcta aattgttaaa      4380
agcagttcat gccattattc ttaataaaca tttctaatat gctgtgaaag ag             4432
```

<210> SEQ ID NO 3
<211> LENGTH: 181
<212> TYPE: PRT
<213> ORGANISM: Homo sapiens

<400> SEQUENCE: 3

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 4
<211> LENGTH: 181
<212> TYPE: PRT
<213> ORGANISM: Homo sapiens

<400> SEQUENCE: 4

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110
```

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 5
<211> LENGTH: 209
<212> TYPE: PRT
<213> ORGANISM: Homo sapiens

<400> SEQUENCE: 5

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 6
<211> LENGTH: 177
<212> TYPE: PRT
<213> ORGANISM: Homo sapiens

<400> SEQUENCE: 6

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

```
-continued

Glu Asp Gly Thr Val Gly Gly Ala Ala Asp Gln Ser Pro Glu Ser Leu
        35              40                  45

Leu Gln Leu Lys Ala Leu Lys Pro Gly Val Ile Gln Ile Leu Gly Val
 50              55                  60

Lys Thr Ser Arg Phe Leu Cys Gln Arg Pro Asp Gly Ala Leu Tyr Gly
 65              70                  75                      80

Ser Leu His Phe Asp Pro Glu Ala Cys Ser Phe Arg Glu Leu Leu Leu
                 85              90                      95

Glu Asp Gly Tyr Asn Val Tyr Gln Ser Glu Ala His Gly Leu Pro Leu
            100             105             110

His Cys Pro Gly Asn Lys Ser Pro His Arg Asp Pro Ala Pro Arg Gly
        115             120             125

Pro Cys Arg Phe Leu Pro Leu Pro Gly Leu Pro Pro Ala Pro Pro Glu
    130             135             140

Pro Pro Gly Ile Leu Ala Pro Gln Pro Pro Asp Val Gly Ser Ser Asp
145             150             155             160

Pro Leu Ala Met Val Gly Pro Ser Gln Gly Arg Ser Pro Ser Tyr Ala
                165             170             175

Ser
```